US009839697B2

(12) United States Patent
Thess et al.

(10) Patent No.: US 9,839,697 B2
**(45) Date of Patent: *Dec. 12, 2017**

(54) NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED PROTEIN

(71) Applicant: CureVac AG, Tuebingen (DE)

(72) Inventors: Andreas Thess, Kusterdingen (DE); Thomas Schlake, Gundelfingen (DE); Jochen Probst, Wolfschlugen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/945,349

(22) Filed: Nov. 18, 2015

(65) Prior Publication Data

US 2016/0206756 A1 Jul. 21, 2016

Related U.S. Application Data

(63) Continuation of application No. 13/321,474, filed as application No. PCT/EP2011/004077 on Aug. 12, 2011, now Pat. No. 9,234,013.

(30) Foreign Application Priority Data

Aug. 13, 2010 (WO) ................ PCT/EP2010/004998

(51) Int. Cl.

| | |
|---|---|
| ***A61K 48/00*** | (2006.01) |
| ***C12N 15/67*** | (2006.01) |
| ***C07K 14/435*** | (2006.01) |
| ***A61K 39/00*** | (2006.01) |
| *A61K 38/02* | (2006.01) |
| *A61K 38/03* | (2006.01) |
| *A61K 38/04* | (2006.01) |
| *A61K 38/10* | (2006.01) |
| *A61K 38/16* | (2006.01) |
| *C07H 21/04* | (2006.01) |

(52) U.S. Cl.

CPC ...... *A61K 48/0066* (2013.01); *A61K 39/0011* (2013.01); *C07K 14/435* (2013.01); *C12N 15/67* (2013.01); *A61K 2039/53* (2013.01); *A61K 2039/575* (2013.01)

(58) Field of Classification Search

None

See application file for complete search history.

(56) References Cited

U.S. PATENT DOCUMENTS

| | | | |
|---|---|---|---|
| 8,217,016 | B2 | 7/2012 | Hoerr et al. |
| 8,383,340 | B2 | 2/2013 | Ketterer et al. |
| 8,703,906 | B2 | 4/2014 | Baumhof et al. |
| 8,968,746 | B2 | 3/2015 | Baumhof et al. |
| 9,155,788 | B2 | 10/2015 | Hoerr et al. |
| 9,447,431 | B2 | 9/2016 | Thess et al. |
| 2005/0009028 | A1 | 1/2005 | Heintz et al. |
| 2005/0032730 | A1 | 2/2005 | Von Der Mülbe et al. |
| 2005/0048549 | A1 | 3/2005 | Cao et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2007/0111203 | A1 | 5/2007 | Cao et al. |
| 2007/0172949 | A9 | 7/2007 | Liu et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0120152 | A1 | 5/2010 | Wooddell et al. |
| 2010/0129392 | A1 | 5/2010 | Shi et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mülbe et al. |
| 2010/0291156 | A1 | 11/2010 | Barner et al. |

(Continued)

FOREIGN PATENT DOCUMENTS

| | | |
|---|---|---|
| WO | WO 95/15394 | 6/1995 |
| WO | WO 98/42856 | 10/1998 |

(Continued)

OTHER PUBLICATIONS

Avni et al., "The 5' terminal oligopyrimidine tract confers translational control on TOP mRNAs in a cell type-and sequence context-dependent manner," *Nucleic Acids Research*, 25(5):995-1001, 1997.

Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.

Battle and Doudna, "The stem-loop binding protein forms a highly stable and specific complex with the 3' stem-loop of histone mRNAs," *RNA*, 7:123-132, 2001.

(Continued)

*Primary Examiner* — Nancy J Leith

(74) *Attorney, Agent, or Firm* — Parker Highlander PLLC

(57) ABSTRACT

The present application describes a coding nucleic acid sequence, particularly a messenger RNA (mRNA), comprising or coding for a histone stem-loop and a poly(A) sequence or a polyadenylation signal and the use thereof for increasing the expression of an encoded protein. It also discloses its use for the preparation of a pharmaceutical composition, especially a vaccine e.g. for the use in the treatment of tumors and cancer diseases, cardiovascular diseases, infectious diseases, autoimmune diseases or genetic diseases, or in gene therapy. The present invention further describes an in vitro transcription method, in vitro methods for increasing the expression of a protein using the nucleic acid comprising or coding for a histone stem-loop and a poly(A) sequence or a polyadenylation signal and an ex vivo and in vivo method.

20 Claims, 23 Drawing Sheets

(56) References Cited

U.S. PATENT DOCUMENTS

| | | | |
|---|---|---|---|
| 2010/0303851 | A1 | 12/2010 | Hoerr et al. |
| 2010/0305196 | A1 | 12/2010 | Probst et al. |
| 2011/0053829 | A1 | 3/2011 | Baumhof et al. |
| 2011/0077287 | A1 | 3/2011 | Von Der Mülbe et al. |
| 2011/0250225 | A1 | 10/2011 | Fotin-Mleczek et al. |
| 2011/0269950 | A1 | 11/2011 | Von Der Mulbe et al. |
| 2011/0311472 | A1 | 12/2011 | Hoerr et al. |
| 2012/0009221 | A1 | 1/2012 | Hoerr et al. |
| 2012/0021043 | A1 | 1/2012 | Kramps et al. |
| 2012/0213818 | A1 | 8/2012 | Hoerr et al. |
| 2012/0258046 | A1 | 10/2012 | Mutzke |
| 2013/0121988 | A1 | 5/2013 | Hoerr et al. |
| 2013/0129754 | A1 | 5/2013 | Thess et al. |
| 2013/0195867 | A1 | 8/2013 | Hoerr et al. |
| 2013/0202645 | A1 | 8/2013 | Barner et al. |
| 2013/0251742 | A1 | 9/2013 | Probst et al. |
| 2013/0259879 | A1 | 10/2013 | Baumhof et al. |
| 2013/0273001 | A1 | 10/2013 | Hoerr et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2014/0037660 | A1 | 2/2014 | Fotin-Mleczek et al. |
| 2014/0147454 | A1 | 5/2014 | Chakraborty et al. |
| 2014/0294877 | A1 | 10/2014 | Baumhof et al. |
| 2015/0050302 | A1 | 2/2015 | Thess |
| 2015/0057340 | A1 | 2/2015 | Thess et al. |
| 2015/0093413 | A1 | 4/2015 | Thess |
| 2015/0104476 | A1 | 4/2015 | Von Der Mülbe et al. |
| 2015/0118183 | A1 | 4/2015 | Baumhof |
| 2015/0118264 | A1 | 4/2015 | Baumhof et al. |
| 2015/0141498 | A1 | 5/2015 | Mutzke |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0258214 | A1 | 9/2015 | Baumhof et al. |
| 2015/0306249 | A1 | 10/2015 | Baumhof et al. |
| 2015/0320847 | A1 | 11/2015 | Thess et al. |

FOREIGN PATENT DOCUMENTS

| | | |
|---|---|---|
| WO | WO 01/12824 | 2/2001 |
| WO | WO 02/098443 | 12/2002 |
| WO | WO 2006/008154 | 1/2006 |
| WO | WO 2006/024518 | 3/2006 |
| WO | WO 2007/024708 | 3/2007 |
| WO | WO 2009/030481 | 3/2009 |
| WO | WO 2009/095226 | 8/2009 |
| WO | WO 2010/023260 | 3/2010 |
| WO | WO 2010/132867 | 11/2010 |
| WO | WO 2011/069529 | 6/2011 |
| WO | WO 2012/013326 | 2/2012 |
| WO | WO 2012/019630 | 2/2012 |
| WO | WO 2012/116714 | 9/2012 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2015/024665 | 2/2015 |
| WO | WO 2015/024668 | 2/2015 |

OTHER PUBLICATIONS

Caldarola et al., "Translational regulation of terminal oligopyrimidine mRNAs induced by serum and amino acids involves distinct signaling events," *The Journal of Biological Chemistry*, 279(14):13522-135531, 2004.

Cameron et al., "Recent advances in transgenic technology," *Molecular Biotechnology*, 7:253-265, 1997.

Chakrabarti et al., "The mammalian target of rapamycin complex 1 regulates leptin biosynthesis in adipocytes at the level of translation: role of the 5'-untranslated region in the expression of leptin messenger ribonucleic acid," *Molecular Endocrinology*, 22(10):2260-2267, 2008.

Collart et al., "A human histone H2B.1 variant gene, located on chromosome 1, utilizes alternative 3' end processing," *Journal of Cellular Biochemistry*, 50:374-385, 1992.

Damgaard and Lykke-Andersen, "Translational coregulation of 5'TOP mRNAs by TIA-1 and TIAR," *Genes Dev.*, 25:2057-2068, 2011.

Database EMBL Accession No. EM_STD:AB063609, "*Homo sapiens* RPL36AL mRNA for ribosomal protein L36a-like, complete cds," 2002.

Database Geneseq Accession No. ATN08647, "Human transcriptional regulatory element SEQ ID No. 6587," 2008.

Davuluri et al., "CART classification of human 5' UTR sequences," *Genome Research*, 10(11):1807-1816, 2000.

Eckner et al., "Mature mRNA 3' end formation stimulates RNA export from the nucleus," *The EMBO Journal*, 10(11):3513-3522, 1991.

Gallie et al., "The histone 3'-terminal stem-loop is necessary for translation in Chinese hamster ovary cells," *Nucleic Acids Res.*, 24(10):1954-1962, 1996.

Gerwitz et al., "Nucleic acid therapeutics: state of the art and future prospects," *Blood*, 92(3):712-736, 1998.

Ginn et al., "Gene therapy clinical trails worldwide to 2012—an update," *Journal of Gene Medicine*, 15:65-77, 2013.

Gorgoni al., "The stem-loop binding protein stimulates histone translation at an early step in the initiation pathway," *RNA*, 11:1030-1042, 2005.

Holtkamp et al., "Modification of antigen-encoding RNA increases stability, translational efficacy, and T-cell stimulatory capacity of dendritic cells," *Blood*, 108(13):4009-17, 2006.

Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.

Kato et al., "Histone H2B as an antigen recognized by lung cancer-specific human monoclonal antibody HB4C5," *Human Antibodies and Hybridomas*, 2(2):94-101, 1991.

Knapinska et al., "Molecular mechanisms regulation mRNA stability: physiological and pathological significance," *Current Genomics*, 6(6):1-16, 2005.

Ledda et al., "Effect of 3' UTR length on the translational regulation of 5'-terminal oligopyrimidine mRNAs," *Gene*, 344:213-220, 2005.

Levy et al., "Oligopyrimidine tract at the 5' end of mammalian ribosomal protein mRNAs is required for their translational control," *Proc. Natl. Acad. Sci. USA*, 88:3319-3323, 1991.

Levy et al., "Sequence and functional characterization of the terminal exon of the human insulin receptor gene," *Biochim Biophys Acta.*, 1263(3):253-257, 1995.

Ling et al., "The histone 3'-terminal stem-loop-binding protein enhances translation through a functional and physical interaction with eukaryotic initiation factor 4G (elF4G) and elF3," *Mol Cell Biol.*, 22:7853-7867, 2002.

Lopez and Samuelsson, "Early evolution of histone mRNA 3' end processing," *Bioinformatics*, 14(1):1-10, 2008.

Meyuhas, "Synthesis of the translational apparatus is regulated at the translational level," *Eur. J. Biochem.*, 267:6321-6330, 2000.

Montoliu, "Gene transfer strategies in animal transgenesis," *Cloning and Stem Cells*, 4(1):39-46, 2002.

Narita et al., "NELF interacts with CDC and participates in 3' end processing of replication-dependent histone mRNAs," *Molecular Cell*, 26(3):349-365, 2007.

Niemann, "Transgenic farm animals get off the ground," *Transgenic Research*, 7:73-75, 1998.

Office Action issued in U.S. Appl. No. 13/321,474, dated Apr. 6, 2015.

Office Action issued in U.S. Appl. No. 13/321,474, dated May 20, 2014.

Office Action issued in U.S. Appl. No. 14/378,538, dated Jun. 21, 2016.

Office Action issued in U.S. Appl. No. 14/378,538, dated Nov. 12, 2015.

Office Action issued in U.S. Appl. No. 14/378,572, dated Aug. 12, 2016.

Office Action issued in U.S. Appl. No. 14/378,572, dated Mar. 3, 2016.

(56) References Cited

OTHER PUBLICATIONS

Office Action issued in U.S. Appl. No. 14/378,591, dated Aug. 22, 2016.
Office Action issued in U.S. Appl. No. 14/378,606, dated May 27, 2015.
Office Action issued in U.S. Appl. No. 14/378,606, dated Nov. 3, 2015.
Office Action issued in U.S. Appl. No. 14/388,224, dated Apr. 21, 2016.
Office Action issued in U.S. Appl. No. 14/388,226, dated Jun. 21, 2016.
Office Action issued in U.S. Appl. No. 14/388,226, dated Nov. 6, 2015.
Orom et al., "MicroRNA-10a binds the 5'UTR of ribosomal protein mRNAs and enhances their translation," *Molecular Cell*, 30:460-471, 2008.
Pandey et al., "Introns in histone genes alter the distribution of 3' ends," *Nucleic Acids Res.*, 18(11):3161-3170, 1990.
PCT International Search Report and Written Opinion issued in International Application No. PCT/EP2013/000938, dated Nov. 13, 2013.
PCT International Search Report and Written Opinion issued in International Application No. PCT/EP2013/000461, dated Apr. 16, 2013.
PCT International Search Report and Written Opinion issued in International Application No. PCT/EP2013/000458, dated Apr. 24, 2013.
PCT International Search Report and Written Opinion issued in International Application No. PCT/EP2013/000459, dated Apr. 23, 2013.
PCT International Search Report and Written Opinion issued in International Application No. PCT/EP2013/000460, dated Apr. 22, 2013.
PCT International Search Report and Written Opinion issued in International Application No. PCT/EP2011/004077, dated Nov. 10, 2011.
PCT International Search Report and Written Opinion issued in International Application No. PCT/EP2013/000937, dated Aug. 30, 2013.
Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear —safety-optimized mRNA vaccination with a panel of 29 allergens," *Journal of Allergy and Clinical Immunology*, 124(5):1070-1077, 2009.
Russell et al., "The stability of human beta-globin mRNA is dependent on structural determinants positioned within its 3' untranslated region," *Blood*, 87:5314-5323, 1996.
Sanchez et al., "Increased levels of polyadenylated histone H2B mRNA accumulate during *Entamoeba invadens* cyst formation," *Molecular and Biochemical Parasitology*, 67(1):137-146, 1994.
Sanchez et al., "The oligo(A) tail on histone mRNA plays an active role in translational silencing of histone mRNA during Xenopus oogenesis," *Mol Cell Biol.*, 24(6):2513-2525, 2004.
Shen et al., "Structures required for poly(A) tail-independent translation overlap with, but ar distinct from, cap-independent translation and RNA replication signals at the 3' end of *Tobacco necrosis* virus RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Smith, "Gene transfer in higher animals: theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment," *EMBO J.*, 5(12):3297-3303, 1986.
Svoboda et al., "Hairpin RNA; a secondary structure of primary importance," *Cell Mol Life Sci.*, 63(7-8):901-908, 2006.
Thess et al., "Sequence-engineered mRNA without chemical nucleoside modifications enables an effective protein therapy in large animals," *Molecular Therapy*, pp. 1-9 and Supplementary Material, 2015.
Wagner et al., "A genome-wide RNA interference screen reveals that variant histones are necessary for replication-dependent histone pre-mRNA processing", *Molecular Cell*, 28(4):692-699, 2007.
Weiss et al., "Prophylactic mRNA vaccination against allergy," *Current Opinion in Allergy and Clinical Immunology*, 10(6):567-574, 2010.
Williams et al., "A simple, highly efficient method for heterologous expression in mammalian primary neurons using cationic lipid-mediated mRNA transfection," *Frontiers in Neuroscience*, 4:1-20, 2010.
Wooddell et al., "Sustained liver-specific transgene expression from the albumin promoter in mice following hydrodynamic plasmid DNA delivery," *The Journal of Gene Medicine*, 10:551-563, 2008.
Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.
Zhong et al., "A double-stranded RNA binding protein required for activation of repressed messages in mammalian germ cells," *Nat Genet.*, 22(2):171-174, 1999.
Zhe et al., "Binding of the La autoantigen to the 5' untranslated region of a chimeric human translation elongation factor 1A reporter mRNA inhibits translation in vitro," *Biochimica et Biophysica Acta*, 1521:19-29, 2001.
Dominski et al., "Stem-loop binding protein facilitates 3'-end formation by stabilizing U7 snRNP binding to histone pre-mRNA," *Mol Cell Biol.*, 19(5):3561-3570, 1999.
Attwood, "The babel of bioinformatics," *Science*, 290(5491):471-473, 2000.
Blumenthal et al., "Definition of an allergen (immunobiology)," *Allergens and Allergen Immunotherapy*, Ed. R. Lockey, S. Bukantz and J. Bousquet, pp. 37-50, 2004.
Cheung et al., "Specific interaction of HeLa cell proteins with coxsackievirus B3 3'UTR: La autoantigen binds the 3' and 5' UTR independently of the poly(A) tail," *Cell Microbiol.*, 9(7):1705-1715, 2007.
Deml et al., "Multiple effects of codon usage optimization on expression and immunogenicity of DNA candidate vaccines encoding the human immunodeficiency virus type 1 Gag protein," Journal of Virology, 75(22):10991-11001, 2001.
Dollé et al., "Nerve growth factor overexpression and autocrine loop in breast cancer cells," *Oncogene*, 22(36):5592-5601, 2003.
Haines et al., "CL22—a novel cationic peptide for efficient transfection of mammalian cells," *Gene Ther.*, 8:99-110, 2001.
Henke et al., "Coxsackievirus B3 vaccines: use as an expression vector for prevention of myocarditis," *Expert Rev. Vaccines*, 7(10):1557-1567, 2008.
Kim et al., "Coxsackievirus B3 used as a gene therapy vector to express functional FGF2," *Gene Ther.*, 19(12):1159-1165, 2012.
Kim et al., "Systematic analysis of attenuated *Coxsackievirus* expressing a foreign gene as a viral vaccine vector," *Vaccine*, 28(5):1234-1240, 2010.
Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.
Kudla et al., "High guanine and cytosine content increases mRNA levels in mammalian cells," *PLoS Biology*, 4:0933-0942, 2006.
Lorenzi et al., "Intranasal vaccination with messenger RNA as a new approach in gene therapy: use against tuberculosis," *BMC Biotechnology*, 10:77, 2010.
Meier et al., "Fibroblast growth factor-2 but not Mel-CAM and/or β3 integrin promotes progression of melanocytes to melanoma," *Exp. Dermatol.*, 12(31:296-306, 2003.

(56) References Cited

OTHER PUBLICATIONS

Ngo et al., "Computational complexity, protein structure prediction, and the levinthal paradox," *The Protein Folding Problem and Tertiary Structure Prediction*, Ed. K. Merz and S. Le Grand, pp. 491-495, 1994.
Office Action issued in U.S. Appl. No. 14/378,538, dated Oct. 11, 2016.
Office Action issued in U.S. Appl. No. 14/378,572, dated Mar. 14, 2017.
Office Action issued in U.S. Appl. No. 14/378,591, dated Jan. 27, 2017.
Office Action issued in U.S. Appl. No. 14/388,224, dated Oct. 17, 2016.
Oliveira et al., "Inhibition of translational initiation in *Saccharomyces cerevisiae* by secondary structure: the roles of the stability and position of stem-loops in the mRNA leader,"*Mol. Microbiol.*, 9(3):521-532, 1993.
Palmowski et al., "Intravenous injection of a lentiviral vector encoding NY-ESO-1 induces an effective CTL response," *J. Immunol.*, 172(3):1582-1587, 2004.
Sharma et al., "Functional role of the 5' terminal cloverleaf in Coxsackievirus RNA replication," *Virology*, 393(2):238-249, 2009.
Skolnick et al., "From genes to protein structure and function: novel applications of computational approaches in the genomic era," *Trends in Biotech.*, 18:34-39, 2000.
van Ooij et al., "Polyadenylation of genomic RNA and initiation of antigenomic RNA in a positive-strand RNA virus are controlled by the same *cis*-element," *Nucleic Acids Res.*, 34(10):2953-2965, 2006.
Kubler et al., "Self-adjuvanted mRNA vaccination in advanced prostate cancer patients: a first-in-man phase I/IIa study," *Journal for ImmunoTherapy of Cancer*, 3:26, 2015.

| #A | #T | #C | #G | Cons | 99% | 95% | 90% | | |
|---|---|---|---|---|---|---|---|---|---|
| 2224 | 172 | 1557 | 25 | N* | H* | M* | M* | | |
| 1586 | 188 | 2211 | 16 | N* | H* | H* | M* | | |
| 3075 | 47 | 875 | 4 | N | H | M | M | | |
| 2872 | 205 | 918 | 6 | N | H | H | M | | |
| 1284 | 19 | 2675 | 23 | N | V | M | M | | |
| 184 | 6 | 270 | 3541 | N | V | S | S | ^ | ⎫ |
| 0 | 0 | 0 | 4001 | G | G | G | G | ^ | ⎪ |
| 13 | 569 | 3394 | 25 | N | Y | Y | Y | ^ | ⎬ Stem 1 |
| 12 | 1620 | 2342 | 27 | N | Y | Y | Y | ^ | ⎪ |
| 9 | 199 | 3783 | 10 | N | Y | Y | C | ^ | ⎪ |
| 1 | 3947 | 51 | 2 | N | Y | T | T | ^ | ⎭ |
| 47 | 3830 | 119 | 5 | N | H | T | T | • | ⎫ |
| 59 | 3704 | 227 | 11 | N | H | Y | T | • | ⎬ Loop |
| 0 | 4001 | 0 | 0 | T | T | T | T | • | ⎪ |
| 675 | 182 | 3140 | 4 | N | H | M | M | • | ⎭ |
| 3818 | 1 | 7 | 175 | N | R | A | A | v | ⎫ |
| 195 | 21 | 50 | 3735 | N | V | R | G | v | ⎪ |
| 1596 | 15 | 31 | 2359 | N | V | R | R | v | ⎬ Stem 2 |
| 523 | 11 | 16 | 3451 | N | R | R | R | v | ⎪ |
| 0 | 0 | 4001 | 0 | C | C | C | C | v | ⎪ |
| 14 | 179 | 3543 | 265 | N | B | S | S | v | ⎭ |
| 3727 | 8 | 154 | 112 | N | V | M | A | | |
| 61 | 64 | 3870 | 4 | N | H | C | C | | |
| 771 | 557 | 2636 | 37 | N* | H* | H* | H* | | |
| 2012 | 201 | 1744 | 43 | N* | N* | H* | M* | | |
| 2499 | 690 | 674 | 138 | N* | N* | H* | H* | | |

Figure 1

| | | | | | | Stem 1 | | | | | | Loop | | | | Stem 2 | | | | | | | | | | |
|---|---|---|---|---|---|---|---|---|---|---|---|---|---|---|---|---|---|---|---|---|---|---|---|---|---|---|
| | | | | | | < | < | < | < | < | < | • | • | • | • | > | > | > | > | > | > | | | | | |
| # A | 52 | 32 | 71 | 82 | 76 | 13 | 0 | 12 | 12 | 9 | 1 | 46 | 3 | 0 | 75 | 82 | 53 | 79 | 20 | 0 | 4 | 94 | 17 | 35 | 74 | 56 |
| # T | 20 | 32 | 37 | 21 | 8 | 3 | 0 | 21 | 85 | 58 | 86 | 70 | 65 | 131 | 28 | 1 | 17 | 13 | 10 | 0 | 15 | 7 | 31 | 32 | 20 | 28 |
| # C | 45 | 59 | 20 | 25 | 38 | 0 | 0 | 86 | 8 | 54 | 42 | 13 | 58 | 0 | 27 | 2 | 6 | 31 | 10 | 131 | 112 | 5 | 82 | 58 | 30 | 40 |
| # G | 14 | 8 | 3 | 3 | 9 | 115 | 131 | 12 | 26 | 10 | 2 | 2 | 5 | 0 | 1 | 46 | 55 | 8 | 91 | 0 | 0 | 25 | 1 | 6 | 7 | 7 |
| Cons | N* | N* | N | N | N | D | G | N | N | N | N | N | N | T | N | N | N | N | N | C | H | N | N | N* | N* | N* |
| 99% | N* | N* | N | N | N | D | G | N | N | N | B | N | N | T | H | V | N | N | N | C | H | N | H | N* | N* | N* |
| 95% | N* | N* | H | H | N | R | G | N | N | N | Y | H | B | T | H | R | D | N | N | C | Y | D | H | H* | N* | N* |
| 90% | N* | H* | H | H | V | R | G | N | D | B | Y | H | Y | T | H | R | D | H | N | C | Y | R | H | H* | H* | H* |

Figure 2

| | | | | | | Stem 1 | | | | | | Loop | | | | Stem 2 | | | | | | | | | | |
|---|---|---|---|---|---|---|---|---|---|---|---|---|---|---|---|---|---|---|---|---|---|---|---|---|---|
| | | | | | | < | < | < | < | < | < | • | • | • | • | > | > | > | > | > | > | | | | | |
| # A | 2172 | 1554 | 3004 | 2790 | 1208 | 171 | 0 | 1 | 0 | 0 | 0 | 1 | 56 | 0 | 600 | 3736 | 142 | 1517 | 503 | 0 | 10 | 3633 | 44 | 736 | 1938 | 2443 |
| # T | 152 | 156 | 10 | 184 | 11 | 3 | 0 | 548 | 1535 | 141 | 3861 | 3760 | 3639 | 3870 | 154 | 0 | 4 | 2 | 1 | 0 | 164 | 1 | 33 | 525 | 181 | 662 |
| # C | 1512 | 2152 | 855 | 893 | 2637 | 270 | 0 | 3308 | 2334 | 3729 | 9 | 106 | 169 | 0 | 3113 | 5 | 44 | 0 | 6 | 3870 | 3431 | 149 | 3788 | 2578 | 1714 | 634 |
| # G | 11 | 8 | 1 | 3 | 14 | 3426 | 3870 | 13 | 1 | 0 | 0 | 3 | 6 | 0 | 3 | 129 | 3680 | 2351 | 3360 | 0 | 265 | 87 | 3 | 31 | 36 | 131 |
| Cons | N* | N* | N | N | N | N | G | N | B | Y | Y | N | N | T | N | V | N | D | N | C | N | N | N | N* | N* | N* |
| 99% | H* | H* | M | H | M | V | G | Y | Y | Y | T | Y | H | T | H | R | V | R | R | C | B | V | M | H* | H* | N* |
| 95% | M* | M* | M | M | M | S | G | Y | Y | C | T | T | Y | T | M | A | G | R | R | C | S | M | C | H* | H* | H* |
| 90% | M* | M* | M | M | M | S | G | Y | Y | C | T | T | T | T | M | A | G | R | R | C | S | A | C | H* | M* | H* |

Figure 3

| | | | | | | | | | | | | | | | | | | | | | | | | | | |
|---|---|---|---|---|---|---|---|---|---|---|---|---|---|---|---|---|---|---|---|---|---|---|---|---|---|---|
| | | | | | | < | < | < | < | < | < | • | • | • | • | > | > | > | > | > | > | | | | | |
| #A | 661 | 146 | 1315 | 1323 | 920 | 8 | 0 | 1 | 0 | 0 | 0 | 1 | 4 | 0 | 441 | 1333 | 0 | 1199 | 21 | 0 | 1 | 1126 | 26 | 81 | 380 | 960 |
| #T | 63 | 121 | 2 | 2 | 6 | 2 | 0 | 39 | 1217 | 2 | 1331 | 1329 | 1207 | 1333 | 30 | 0 | 1 | 0 | 1 | 0 | 2 | 1 | 22 | 91 | 91 | 12 |
| #C | 601 | 1062 | 16 | 6 | 403 | 1 | 0 | 1293 | 116 | 1331 | 2 | 0 | 121 | 0 | 862 | 0 | 2 | 0 | 0 | 1333 | 1328 | 128 | 1284 | 1143 | 834 | 361 |
| #G | 8 | 4 | 0 | 2 | 4 | 1322 | 1333 | 0 | 0 | 0 | 0 | 3 | 1 | 0 | 0 | 0 | 1330 | 134 | 1311 | 0 | 2 | 78 | 1 | 18 | 28 | 0 |
| Cons | N* | N* | H | N | N | N | G | H | Y | Y | Y | D | N | T | H | A | B | R | D | C | N | N | N | N* | N* | H* |
| 99% | H* | H* | M | A | M | G | G | Y | Y | C | T | T | Y | T | H | A | G | R | R | C | C | V | H | N* | N* | M* |
| 95% | H* | H* | A | A | M | G | G | C | Y | C | T | T | Y | T | M | A | G | R | G | C | C | V | C | H* | H* | M* |
| 90% | M* | M* | A | A | M | G | G | C | T | C | T | T | T | T | M | A | G | R | G | C | C | M | C | Y* | M* | M* |

Stem 1

Loop

Stem 2

Figure 4

| 90% | 95% | 99% | Cons | #G | #C | #T | #A | | |
|---|---|---|---|---|---|---|---|---|---|
| H* | H* | N* | N* | 4 | 62 | 8 | 10 | | |
| M* | H* | H* | H* | 0 | 61 | 6 | 17 | | |
| A | A | A | A | 0 | 0 | 0 | 84 | | |
| A | A | A | A | 0 | 0 | 0 | 84 | | |
| A | M | H | H | 0 | 6 | 2 | 76 | | |
| G | G | D | D | 81 | 0 | 2 | 1 | < | Stem 1 |
| G | G | G | G | 84 | 0 | 0 | 0 | < | |
| C | C | H | H | 0 | 82 | 1 | 1 | < | |
| Y | Y | Y | Y | 0 | 17 | 67 | 0 | < | |
| C | C | C | C | 0 | 84 | 0 | 0 | < | |
| T | T | T | T | 0 | 0 | 84 | 0 | < | |
| T | T | D | D | 3 | 0 | 80 | 1 | • | Loop |
| T | T | Y | Y | 0 | 3 | 81 | 0 | • | |
| T | T | T | T | 0 | 0 | 84 | 0 | • | |
| M | H | H | H | 0 | 67 | 5 | 12 | • | |
| A | A | A | A | 0 | 0 | 0 | 84 | > | Stem 2 |
| G | G | S | S | 83 | 1 | 0 | 0 | > | |
| R | R | R | R | 19 | 0 | 0 | 65 | > | |
| G | G | R | R | 81 | 0 | 0 | 3 | > | |
| C | C | C | C | 0 | 84 | 0 | 0 | > | |
| C | C | C | C | 0 | 84 | 0 | 0 | > | |
| R | V | V | V | 10 | 5 | 0 | 69 | | |
| M | M | H | H | 0 | 75 | 4 | 5 | | |
| Y* | Y* | B* | B* | 2 | 57 | 25 | 0 | | |
| H* | N* | N* | N* | 6 | 44 | 24 | 10 | | |
| M* | M* | H* | H* | 0 | 17 | 3 | 64 | | |

Figure 5 ppLuc(GC) – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagauc-3’

Figure 6 ppLuc(GC) – ag – A64 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAA-3′

Figure 7 ppLuc(GC) – ag – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuCAAAGGCUCUUUUCAGAGCCACCA-3′

Figure 8 ppLuc(GC) – ag – A64 – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCAAAGGCUCUUUCAGAGCCACCA-3′

Figure 9 ppLuc(GC) – ag – A120 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAAA-3'

Figure 10 ppLuc(GC) – ag – A64 – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAA
AAAAAugcauCCUGCCCGAUGGGCCUCCCAACGGGCCCUCCUCCCCUCCUUGCACCG3′

Figure 11 ppLuc(GC) – ag – A64 – aCPSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAugcau*CAAUUCCUACACGUGAGGCGCUGUGAUUCCCUAUCCCCCUUCAUUCCCU*
*AUACAUUAGCACAGCGCCAUUGCAUGUAGGAAUU*-3'

Figure 12 ppLuc(GC) – ag – A64 – PolioCL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*CAAUUCUAAAACAGCUCUGGGGUUGUACCCACCCCAGAGGCCCACGUGG*
*CGGCUAGUACUCCGGUAUUGCGGUACCCUUGUACGCCUGUUUUAGAAUU-3'*

Figure 13 ppLuc(GC) – ag – A64 – G30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*GGGGGGGGGGGGGGGGGGGGGGGGGGGGGG*-3'

Figure 14 ppLuc(GC) – ag – A64 – U30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugca*UUUUUUUUUUUUUUUUUUUUUUUUUUUUUU*-3'

Figure 15 ppLuc(GC) – ag – A64 – SL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*UAUGGCGGCCGUGUCCACCACGGAUAUCACCGUGGUGGACGCGGCC*-3′

Figure 16 ppLuc(GC) – ag – A64 – N32 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAA
AAAAAugcau*CCCCCUCUAGACAAUUGGAAUUCCAUA*-3′

Figure 17

SEQUENCE LISTING

<160> NUMBER OF SEQ ID NOS: 95

<210> SEQ ID NO 1
<211> LENGTH: 16
<212> TYPE: DNA
<213> ORGANISM: Artificial Sequence
<220> FEATURE:
<223> OTHER INFORMATION: stem loop structure according to formula (Ic)
<220> FEATURE:
<221> NAME/KEY: variation
<222> LOCATION: (1)..(1)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (3)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: variation
<222> LOCATION: (10)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (10)..(14)
<223> OTHER INFORMATION: n is a, c, g, t or u
<220> FEATURE:
<221> NAME/KEY: variation
<222> LOCATION: (16)..(16)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (16)..(16)
<223> OTHER INFORMATION: n is a, c, g, t or u

<400> SEQUENCE: 1
ngnnnnnnun nnnncn 16

<210> SEQ ID NO 2
<211> LENGTH: 26
<212> TYPE: DNA
<213> ORGANISM: Artificial Sequence
<220> FEATURE:
<223> OTHER INFORMATION: stem loop structure according to formula (IIc)
<220> FEATURE:
<221> NAME/KEY: variation
<222> LOCATION: (1)..(6)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: variation
<222> LOCATION: (8)..(13)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(13)
<223> OTHER INFORMATION: n is a, c, g, t or u
<220> FEATURE:
<221> NAME/KEY: variation
<222> LOCATION: (15)..(19)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (15)..(19)
<223> OTHER INFORMATION: n is a, c, g, t or u
<220> FEATURE:
<221> NAME/KEY: variation
<222> LOCATION: (21)..(26)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (21)..(26)
<223> OTHER INFORMATION: n is a, c, g, t or u

<400> SEQUENCE: 2
nnnnnngnnn nnnunnnnnc nnnnnn 26

<210> SEQ ID NO 3
<211> LENGTH: 16
<212> TYPE: DNA
<213> ORGANISM: Artificial Sequence
<220> FEATURE:
<223> OTHER INFORMATION: stem loop structure according to formula (Id)
<220> FEATURE:
<221> NAME/KEY: variation
<222> LOCATION: (1)..(1)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (3)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: variation
<222> LOCATION: (10)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (10)..(14)
<223> OTHER INFORMATION: n is a, c, g, t or u
<220> FEATURE:
<221> NAME/KEY: variation
<222> LOCATION: (16)..(16)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (16)..(16)
<223> OTHER INFORMATION: n is a, c, g, t or u

<400> SEQUENCE: 3
ncnnnnnnun nnnngn 16

-continued

<210> SEQ ID NO 4
<211> LENGTH: 26
<212> TYPE: DNA
<213> ORGANISM: Artificial Sequence
<220> FEATURE:
<223> OTHER INFORMATION: stem loop structure according to formula (IId)
<220> FEATURE:
<221> NAME/KEY: variation
<222> LOCATION: (1)..(6)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: variation
<222> LOCATION: (8)..(13)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(13)
<223> OTHER INFORMATION: n is a, c, g, t or u
<220> FEATURE:
<221> NAME/KEY: variation
<222> LOCATION: (15)..(19)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (15)..(19)
<223> OTHER INFORMATION: n is a, c, g, t or u
<220> FEATURE:
<221> NAME/KEY: variation
<222> LOCATION: (21)..(26)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (21)..(26)
<223> OTHER INFORMATION: n is a, c, g, t or u

<400> SEQUENCE: 4
nnnnnncnnn nnnunnnnng nnnnnn 26

<210> SEQ ID NO 5
<211> LENGTH: 16
<212> TYPE: DNA
<213> ORGANISM: Artificial Sequence
<220> FEATURE:
<223> OTHER INFORMATION: stem loop structure according to formula (Ie)
<220> FEATURE:
<221> NAME/KEY: variation
<222> LOCATION: (3)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: variation
<222> LOCATION: (10)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (10)..(14)
<223> OTHER INFORMATION: n is a, c, g, t or u

<400> SEQUENCE: 5
dgnnnnnnun nnnnch 16

<210> SEQ ID NO 6
<211> LENGTH: 26
<212> TYPE: DNA
<213> ORGANISM: Artificial Sequence
<220> FEATURE:
<223> OTHER INFORMATION: stem loop structure according to formula (IIe)
<220> FEATURE:
<221> NAME/KEY: variation
<222> LOCATION: (1)..(5)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: variation
<222> LOCATION: (8)..(13)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (8)..(13)
<223> OTHER INFORMATION: n is a, c, g, t or u
<220> FEATURE:
<221> NAME/KEY: variation
<222> LOCATION: (15)..(19)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (15)..(19)
<223> OTHER INFORMATION: n is a, c, g, t or u
<220> FEATURE:
<221> NAME/KEY: variation
<222> LOCATION: (22)..(26)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (22)..(26)
<223> OTHER INFORMATION: n is a, c, g, t or u

<400> SEQUENCE: 6
nnnnndgnnn nnnunnnnnc hnnnnn 26

<210> SEQ ID NO 7
<211> LENGTH: 16
<212> TYPE: DNA
<213> ORGANISM: Artificial Sequence
<220> FEATURE:
<223> OTHER INFORMATION: stem loop structure according to formula (If)
<220> FEATURE:
<221> NAME/KEY: variation
<222> LOCATION: (1)..(1)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (3)..(3)
<223> OTHER INFORMATION: /replace="guanine" /replace="adenine" /replace="thymine" /replace="uracile" /replace="cytosine"

/replace=""
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: variation
<222> LOCATION: (7)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (7)..(8)
<223> OTHER INFORMATION: n is a, c, g, t or u
<220> FEATURE:
<221> NAME/KEY: variation
<222> LOCATION: (10)..(10)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: variation
<222> LOCATION: (12)..(12)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: variation
<222> LOCATION: (14)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: variation
<222> LOCATION: (16)..(16)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (16)..(16)
<223> OTHER INFORMATION: n is a, c, g, t or u

<400> SEQUENCE: 7
ngnbyynnun rndncn 16

<210> SEQ ID NO 8
<211> LENGTH: 26
<212> TYPE: DNA
<213> ORGANISM: Artificial Sequence
<220> FEATURE:
<223> OTHER INFORMATION: stem loop structure according to formula (IIf)
<220> FEATURE:
<221> NAME/KEY: variation
<222> LOCATION: (1)..(6)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: variation -continued
<222> LOCATION: (8)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: variation
<222> LOCATION: (12)..(13)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (12)..(13)
<223> OTHER INFORMATION: n is a, c, g, t or u
<220> FEATURE:
<221> NAME/KEY: variation
<222> LOCATION: (15)..(15)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: variation
<222> LOCATION: (17)..(17)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: variation
<222> LOCATION: (19)..(19)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: variation
<222> LOCATION: (21)..(26)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (21)..(26)
<223> OTHER INFORMATION: n is a, c, g, t or u

<400> SEQUENCE: 8
nnnnnngnby ynnunrndnc nnnnnn 26

<210> SEQ ID NO 9
<211> LENGTH: 16
<212> TYPE: DNA
<213> ORGANISM: Artificial Sequence
<220> FEATURE:
<223> OTHER INFORMATION: stem loop structure according to formula (Ig)
<220> FEATURE:
<221> NAME/KEY: variation
<222> LOCATION: (1)..(1)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(1)

<223> OTHER INFORMATION: n is a, c, g, t or u
<220> FEATURE:
<221> NAME/KEY: variation
<222> LOCATION: (8)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: variation
<222> LOCATION: (16)..(16)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (16)..(16)
<223> OTHER INFORMATION: n is a, c, g, t or u

<400> SEQUENCE: 9
nghyyydnth abrdcn 16

<210> SEQ ID NO 10
<211> LENGTH: 26
<212> TYPE: DNA
<213> ORGANISM: Artificial Sequence
<220> FEATURE:
<223> OTHER INFORMATION: stem loop structure according to formula (IIg)
<220> FEATURE:
<221> NAME/KEY: variation
<222> LOCATION: (1)..(2)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: variation
<222> LOCATION: (4)..(6)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (4)..(6)
<223> OTHER INFORMATION: n is a, c, g, t or u
<220> FEATURE:
<221> NAME/KEY: variation
<222> LOCATION: (13)..(13)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: variation
<222> LOCATION: (21)..(25)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (21)..(25)
<223> OTHER INFORMATION: n is a, c, g, t or u

<400> SEQUENCE: 10
nnhnnnghyy ydnthabrdc nnnnnh 26

```
<210> SEQ ID NO 11
<211> LENGTH: 16
<212> TYPE: DNA
<213> ORGANISM: Artificial Sequence
<220> FEATURE:
<223> OTHER INFORMATION: stem loop structure according to formula (Ih)

<400> SEQUENCE: 11

dghyctdyuh asrrcc                                                         16

<210> SEQ ID NO 12
<211> LENGTH: 26
<212> TYPE: DNA
<213> ORGANISM: Artificial Sequence
<220> FEATURE:
<223> OTHER INFORMATION: stem loop structure according to formula (IIh)
<220> FEATURE:
<221> NAME/KEY: variation
<222> LOCATION: (1)..(1)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (25)..(25)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (25)..(25)
<223> OTHER INFORMATION: n is a, c, g, t or u

<400> SEQUENCE: 12

nhaahdghyc tdyuhasrrc cvhbnh                                              26

<210> SEQ ID NO 13
<211> LENGTH: 16
<212> TYPE: DNA
<213> ORGANISM: Artificial Sequence
<220> FEATURE:
<223> OTHER INFORMATION: histon stem loop sequence according to formula
      (Ic)
<220> FEATURE:
<221> NAME/KEY: variation
<222> LOCATION: (4)..(4)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: variation
<222> LOCATION: (13)..(13)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (13)..(13)
<223> OTHER INFORMATION: n is a, c, g, t or u

<400> SEQUENCE: 13

ggcncttttc agngcc                                                         16

<210> SEQ ID NO 14
<211> LENGTH: 16
```

```
<212> TYPE: DNA
<213> ORGANISM: Artificial Sequence
<220> FEATURE:
<223> OTHER INFORMATION: histon stem loop sequence according to formula
      (Ie)
<220> FEATURE:
<221> NAME/KEY: variation
<222> LOCATION: (5)..(5)
<223> OTHER INFORMATION: n = g or c or t/u or a (any base or not present)
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: variation
<222> LOCATION: (7)..(8)
<223> OTHER INFORMATION: n = g or c or t/u or a (any base or not present)
<220> FEATURE:
<221> NAME/KEY: misc_feature
<222> LOCATION: (7)..(8)
<223> OTHER INFORMATION: n is a, c, g, t or u
<220> FEATURE:
<221> NAME/KEY: variation
<222> LOCATION: (10)..(10)
<223> OTHER INFORMATION: n = g or c or t/u or a (any base or not present)
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: variation
<222> LOCATION: (12)..(13)
<223> OTHER INFORMATION: n = g or c or t/u or a (any base or not present)
<220> FEATURE:
<221> NAME/KEY: misc_feature
<222> LOCATION: (12)..(13)
<223> OTHER INFORMATION: n is a, c, g, t or u

<400> SEQUENCE: 14

ggctntnntn anngcc                                                          16

<210> SEQ ID NO 15
<211> LENGTH: 16
<212> TYPE: DNA
<213> ORGANISM: Artificial Sequence
<220> FEATURE:
<223> OTHER INFORMATION: histon stem loop sequence according to formula
      (If)

<400> SEQUENCE: 15

ggcbcttttc agdgcc                                                          16

<210> SEQ ID NO 16
<211> LENGTH: 16
<212> TYPE: DNA
<213> ORGANISM: Artificial Sequence
<220> FEATURE:
<223> OTHER INFORMATION: histon stem loop sequence according to formula
      (Ig)

<400> SEQUENCE: 16

ggctctttth agagcc                                                          16

<210> SEQ ID NO 17
<211> LENGTH: 16
<212> TYPE: DNA
<213> ORGANISM: Artificial Sequence
<220> FEATURE:
<223> OTHER INFORMATION: histon stem loop sequence according to formula
      (Ih)

<400> SEQUENCE: 17
```

ggcyctttth agrgcc 16

<210> SEQ ID NO 18
<211> LENGTH: 26
<212> TYPE: DNA
<213> ORGANISM: Artificial Sequence
<220> FEATURE:
<223> OTHER INFORMATION: histon stem loop sequence according to formula (IIc)
<220> FEATURE:
<221> NAME/KEY: variation
<222> LOCATION: (1)..(2)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: variation
<222> LOCATION: (4)..(5)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (4)..(5)
<223> OTHER INFORMATION: n is a, c, g, t or u
<220> FEATURE:
<221> NAME/KEY: variation
<222> LOCATION: (9)..(9)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: variation
<222> LOCATION: (18)..(18)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: variation
<222> LOCATION: (24)..(26)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (24)..(26)
<223> OTHER INFORMATION: n is a, c, g, t or u

<400> SEQUENCE: 18 nnanngcnc ttttcagngc cacnnn 26

<210> SEQ ID NO 19
<211> LENGTH: 26
<212> TYPE: DNA
<213> ORGANISM: Artificial Sequence
<220> FEATURE:
<223> OTHER INFORMATION: histon stem loop sequence according to formula (IIe)
<220> FEATURE:
<221> NAME/KEY: variation
<222> LOCATION: (1)..(3)
<223> OTHER INFORMATION: /replace="guanine" /replace="adenine" /replace="thymine" /replace="uracile" /replace="cytosine" /replace=""

<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: variation
<222> LOCATION: (5)..(5)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: variation
<222> LOCATION: (10)..(10)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: variation
<222> LOCATION: (12)..(13)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (12)..(13)
<223> OTHER INFORMATION: n is a, c, g, t or u
<220> FEATURE:
<221> NAME/KEY: variation
<222> LOCATION: (15)..(15)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: variation
<222> LOCATION: (17)..(18)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (17)..(18)
<223> OTHER INFORMATION: n is a, c, g, t or u
<220> FEATURE:
<221> NAME/KEY: variation
<222> LOCATION: (24)..(26)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (24)..(26)
<223> OTHER INFORMATION: n is a, c, g, t or u

<400> SEQUENCE: 19
nnnanggctn tnntnanngc cacnnn 26

<210> SEQ ID NO 20
<211> LENGTH: 26
<212> TYPE: DNA
<213> ORGANISM: Artificial Sequence
<220> FEATURE:
<223> OTHER INFORMATION: histon stem loop sequence according to formula
(IIf)
<220> FEATURE:
<221> NAME/KEY: variation

```
<222> LOCATION: (1)..(2)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: variation
<222> LOCATION: (4)..(5)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (4)..(5)
<223> OTHER INFORMATION: n is a, c, g, t or u
<220> FEATURE:
<221> NAME/KEY: variation
<222> LOCATION: (24)..(26)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (24)..(26)
<223> OTHER INFORMATION: n is a, c, g, t or u

<400> SEQUENCE: 20

nnannggcbc ttttcagdgc cacnnn                                              26

<210> SEQ ID NO 21
<211> LENGTH: 26
<212> TYPE: DNA
<213> ORGANISM: Artificial Sequence
<220> FEATURE:
<223> OTHER INFORMATION: histon stem loop sequence according to formula
      (IIg)
<220> FEATURE:
<221> NAME/KEY: variation
<222> LOCATION: (1)..(1)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (5)..(5)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: variation
<222> LOCATION: (25)..(25)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (25)..(25)
<223> OTHER INFORMATION: n is a, c, g, t or u

<400> SEQUENCE: 21

ncaanggctc tttthagagc caccnh                                              26

<210> SEQ ID NO 22
<211> LENGTH: 26
```

```
<212> TYPE: DNA
<213> ORGANISM: Artificial Sequence
<220> FEATURE:
<223> OTHER INFORMATION: histon stem loop sequence according to formula
      (IIh)
<220> FEATURE:
<221> NAME/KEY: variation
<222> LOCATION: (1)..(1)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (25)..(25)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (25)..(25)
<223> OTHER INFORMATION: n is a, c, g, t or u

<400> SEQUENCE: 22

nhaahggcyc tttthagrgc cvgbnh                                            26


<210> SEQ ID NO 23
<211> LENGTH: 16
<212> TYPE: DNA
<213> ORGANISM: Artificial Sequence
<220> FEATURE:
<223> OTHER INFORMATION: histon stem loop sequence according to formula
      (Ic)

<400> SEQUENCE: 23

vgyyyyhhth rvvrcb                                                       16


<210> SEQ ID NO 24
<211> LENGTH: 16
<212> TYPE: DNA
<213> ORGANISM: Artificial Sequence
<220> FEATURE:
<223> OTHER INFORMATION: histon stem loop sequence according to formula
      (Ic)

<400> SEQUENCE: 24

rgyyyttttm agrrcs                                                       16


<210> SEQ ID NO 25
<211> LENGTH: 16
<212> TYPE: DNA
<213> ORGANISM: Artificial Sequence
<220> FEATURE:
<223> OTHER INFORMATION: histon stem loop sequence according to formula
      (Ic)

<400> SEQUENCE: 25

rgyyyttttm agrrcs                                                       16


<210> SEQ ID NO 26
<211> LENGTH: 16
<212> TYPE: DNA
<213> ORGANISM: Artificial Sequence
<220> FEATURE:
<223> OTHER INFORMATION: histon stem loop sequence according to formula
      (Ic)

<400> SEQUENCE: 26
```

rgyyyyyytm rrrrcs 16

<210> SEQ ID NO 27
<211> LENGTH: 16
<212> TYPE: DNA
<213> ORGANISM: Artificial Sequence
<220> FEATURE:
<223> OTHER INFORMATION: histon stem loop sequence according to formula (Ic)

<400> SEQUENCE: 27 ggcyctttc agrgcc 16

<210> SEQ ID NO 28
<211> LENGTH: 16
<212> TYPE: DNA
<213> ORGANISM: Artificial Sequence
<220> FEATURE:
<223> OTHER INFORMATION: histon stem loop sequence according to formula (Ic)

<400> SEQUENCE: 28
ggcccttttc agggcc 16

<210> SEQ ID NO 29
<211> LENGTH: 16
<212> TYPE: DNA
<213> ORGANISM: Artificial Sequence
<220> FEATURE:
<223> OTHER INFORMATION: histon stem loop sequence according to formula (Ie)
<220> FEATURE:
<221> NAME/KEY: variation
<222> LOCATION: (3)..(5)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (3)..(5)
<223> OTHER INFORMATION: n is a, c, g, t or u
<220> FEATURE:
<221> NAME/KEY: variation
<222> LOCATION: (7)..(8)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (7)..(8)
<223> OTHER INFORMATION: n is a, c, g, t or u
<220> FEATURE:
<221> NAME/KEY: variation
<222> LOCATION: (12)..(14)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (12)..(14)
<223> OTHER INFORMATION: n is a, c, g, t or u

<400> SEQUENCE: 29
dgnnnbnnth vnnnch 16

<210> SEQ ID NO 30
<211> LENGTH: 16
<212> TYPE: DNA
<213> ORGANISM: Artificial Sequence
<220> FEATURE:
<223> OTHER INFORMATION: histon stem loop sequence according to formula (Ie)
<220> FEATURE:
<221> NAME/KEY: variation
<222> LOCATION: (3)..(5)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (3)..(5)
<223> OTHER INFORMATION: n is a, c, g, t or u
<220> FEATURE:
<221> NAME/KEY: variation
<222> LOCATION: (13)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (13)..(14)
<223> OTHER INFORMATION: n is a, c, g, t or u

<400> SEQUENCE: 30
rgnnnyhbth rdnncy 16

<210> SEQ ID NO 31
<211> LENGTH: 16
<212> TYPE: DNA
<213> ORGANISM: Artificial Sequence
<220> FEATURE:
<223> OTHER INFORMATION: histon stem loop sequence according to formula
(Ie)
<220> FEATURE:
<221> NAME/KEY: variation
<222> LOCATION: (3)..(3)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: variation
<222> LOCATION: (14)..(14)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (14)..(14)
<223> OTHER INFORMATION: n is a, c, g, t or u

<400> SEQUENCE: 31
rgndbyhyth rdhncy 16

<210> SEQ ID NO 32
<211> LENGTH: 16
<212> TYPE: DNA
<213> ORGANISM: Artificial Sequence
<220> FEATURE:
<223> OTHER INFORMATION: histon stem loop sequence according to formula
(Ie)

<400> SEQUENCE: 32
rgykyywytw rrmrcy 16

<210> SEQ ID NO 33
<211> LENGTH: 16
<212> TYPE: DNA
<213> ORGANISM: Artificial Sequence
<220> FEATURE:
<223> OTHER INFORMATION: histon stem loop sequence according to formula (Ie)

<400> SEQUENCE: 33
ggctytwytw armgcc 16

<210> SEQ ID NO 34
<211> LENGTH: 16
<212> TYPE: DNA
<213> ORGANISM: Artificial Sequence
<220> FEATURE:
<223> OTHER INFORMATION: histon stem loop sequence according to formula (Ie)

<400> SEQUENCE: 34
ggctttttta agagcc 16

<210> SEQ ID NO 35
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 35
vgyyytyhth ryrrcb 16

<210> SEQ ID NO 36
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 36
sgyycttytm agrrcs 16

<210> SEQ ID NO 37
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 37 sgyyctttm agrrcs 16

<210> SEQ ID NO 38
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 38
sgyyyyyytm rrrrcs 16

<210> SEQ ID NO 39
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 39 ggcyctttc agrgcc 16

<210> SEQ ID NO 40
<211> LENGTH: 16
<212> TYPE: DNA
<213> ORGANISM: Artificial Sequence
<220> FEATURE:
<223> OTHER INFORMATION: histon stem loop sequence according to formula (If)

<400> SEQUENCE: 40
ggcccttttc agggcc 16

<210> SEQ ID NO 41
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 41
ggyycttyth agrrcc 16

<210> SEQ ID NO 42
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 42
ggcycttytm agrgcc 16

<210> SEQ ID NO 43
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 43
ggctcttttm agrgcc 16

<210> SEQ ID NO 44
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 44
rgyyyykytm asrrcb 16

<210> SEQ ID NO 45
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 45
ggctcttttm agagcc 16

<210> SEQ ID NO 46
<211> LENGTH: 16
<212> TYPE: DNA
<213> ORGANISM: Artificial Sequence
<220> FEATURE:
<223> OTHER INFORMATION: histon stem loop sequence according to formula (Ig)

<400> SEQUENCE: 46
ggctcttttc agagcc 16

<210> SEQ ID NO 47
<211> LENGTH: 16
<212> TYPE: DNA
<213> ORGANISM: Artificial Sequence
<220> FEATURE:
<223> OTHER INFORMATION: histon stem loop sequence according to formula (Ih)

<400> SEQUENCE: 47
kgcyctryth agrrcc 16

<210> SEQ ID NO 48
<211> LENGTH: 16
<212> TYPE: DNA
<213> ORGANISM: Artificial Sequence
<220> FEATURE:
<223> OTHER INFORMATION: histon stem loop sequence according to formula (Ih)

<400> SEQUENCE: 48
ggcyctttth agrgcc 16

<210> SEQ ID NO 49
<211> LENGTH: 16
<212> TYPE: DNA
<213> ORGANISM: Artificial Sequence
<220> FEATURE:
<223> OTHER INFORMATION: histon stem loop sequence according to formula (Ih)

<400> SEQUENCE: 49
ggcyctttth agrgcc 16

<210> SEQ ID NO 50
<211> LENGTH: 16
<212> TYPE: DNA
<213> ORGANISM: Artificial Sequence
<220> FEATURE:
<223> OTHER INFORMATION: histon stem loop sequence according to formula (Ih)

<400> SEQUENCE: 50
kghyctkytm asrrcc 16

<210> SEQ ID NO 51
<211> LENGTH: 16
<212> TYPE: DNA
<213> ORGANISM: Artificial Sequence
<220> FEATURE:
<223> OTHER INFORMATION: histon stem loop sequence according to formula (Ih)

<400> SEQUENCE: 51 ggcyctttm agrgcc     16

<210> SEQ ID NO 52
<211> LENGTH: 16
<212> TYPE: DNA
<213> ORGANISM: Artificial Sequence
<220> FEATURE:
<223> OTHER INFORMATION: histon stem loop sequence according to formula
      (Ih)

<400> SEQUENCE: 52
ggctcttttc agagcc     16

<210> SEQ ID NO 53
<211> LENGTH: 26
<212> TYPE: DNA
<213> ORGANISM: Artificial Sequence
<220> FEATURE:
<223> OTHER INFORMATION: histon stem loop sequence according to formula
      (IIc)
<220> FEATURE:
<221> NAME/KEY: variation
<222> LOCATION: (26)..(26)
<223> OTHER INFORMATION: /replace="guanine" /replace="adenine"
      /replace="thymine" /replace="uracile" /replace="cytosine"
      /replace=""
<220> FEATURE:
<221> NAME/KEY: misc_feature
<222> LOCATION: (26)..(26)
<223> OTHER INFORMATION: n is a, c, g, t or u

<400> SEQUENCE: 53
hhhhhvgyyy yhhthrvvrc bvhhhn     26

<210> SEQ ID NO 54
<211> LENGTH: 26
<212> TYPE: DNA
<213> ORGANISM: Artificial Sequence
<220> FEATURE:
<223> OTHER INFORMATION: histon stem loop sequence according to formula
      (IIc)

<400> SEQUENCE: 54
hhmmmrgyyy ttttmagrrc sachhh     26

<210> SEQ ID NO 55
<211> LENGTH: 26
<212> TYPE: DNA
<213> ORGANISM: Artificial Sequence
<220> FEATURE:
<223> OTHER INFORMATION: histon stem loop sequence according to formula
      (IIc)

<400> SEQUENCE: 55
hmmhmrgyyy ttttmagrrc sachhh     26

<210> SEQ ID NO 56
<211> LENGTH: 26
<212> TYPE: DNA
<213> ORGANISM: Artificial Sequence
<220> FEATURE:
<223> OTHER INFORMATION: histon stem loop sequence according to formula
      (IIc)

<400> SEQUENCE: 56
mmmmmrgyyy yyytmrrrrc smymmw     26

```
<210> SEQ ID NO 57
<211> LENGTH: 26
<212> TYPE: DNA
<213> ORGANISM: Artificial Sequence
<220> FEATURE:
<223> OTHER INFORMATION: histon stem loop sequence according to formula
      (IIc)

<400> SEQUENCE: 57

mmammggcyc ttttcagrgc cacmmw                                          26


<210> SEQ ID NO 58
<211> LENGTH: 26
<212> TYPE: DNA
<213> ORGANISM: Artificial Sequence
<220> FEATURE:
<223> OTHER INFORMATION: histon stem loop sequence according to formula
      (IIc)

<400> SEQUENCE: 58

acaacggccc ttttcagggc caccaa                                          26


<210> SEQ ID NO 59
<211> LENGTH: 26
<212> TYPE: DNA
<213> ORGANISM: Artificial Sequence
<220> FEATURE:
<223> OTHER INFORMATION: histon stem loop sequence according to formula
      (IIe)
<220> FEATURE:
<221> NAME/KEY: variation
<222> LOCATION: (1)..(5)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: variation
<222> LOCATION: (8)..(10)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (8)..(10)
<223> OTHER INFORMATION: n is a, c, g, t or u
<220> FEATURE:
<221> NAME/KEY: variation
<222> LOCATION: (12)..(13)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (12)..(13)
<223> OTHER INFORMATION: n is a, c, g, t or u
<220> FEATURE:
<221> NAME/KEY: variation
<222> LOCATION: (17)..(19)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (17)..(19)
<223> OTHER INFORMATION: n is a, c, g, t or u
<220> FEATURE:
<221> NAME/KEY: variation
<222> LOCATION: (22)..(22)
<223> OTHER INFORMATION: /replace="guanine" /replace="adenine"
      /replace="thymine" /replace="uracile"  /replace="cytosine"
      /replace=""
```

<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: variation
<222> LOCATION: (24)..(26)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (24)..(26)
<223> OTHER INFORMATION: n is a, c, g, t or u

<400> SEQUENCE: 59
nnnnndgnnn bnnthvnnnc hnhnnn 26

<210> SEQ ID NO 60
<211> LENGTH: 26
<212> TYPE: DNA
<213> ORGANISM: Artificial Sequence
<220> FEATURE:
<223> OTHER INFORMATION: histon stem loop sequence according to formula
(IIe)
<220> FEATURE:
<221> NAME/KEY: variation
<222> LOCATION: (1)..(2)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: variation
<222> LOCATION: (8)..(10)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(10)
<223> OTHER INFORMATION: n is a, c, g, t or u
<220> FEATURE:
<221> NAME/KEY: variation
<222> LOCATION: (18)..(19)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (18)..(19)
<223> OTHER INFORMATION: n is a, c, g, t or u

<400> SEQUENCE: 60
nnhhhrgnnn yhbthrdnnc ydhhhh 26

<210> SEQ ID NO 61
<211> LENGTH: 26
<212> TYPE: DNA
<213> ORGANISM: Artificial Sequence
<220> FEATURE:
<223> OTHER INFORMATION: histon stem loop sequence according to formula
(IIe)
<220> FEATURE:
<221> NAME/KEY: variation
<222> LOCATION: (1)..(1)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (1)..(1)

<223> OTHER INFORMATION: n is a, c, g, t or u
<220> FEATURE:
<221> NAME/KEY: variation
<222> LOCATION: (8)..(8)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: variation
<222> LOCATION: (19)..(19)
<223> OTHER INFORMATION: /replace="guanine" /replace="adenine"
/replace="thymine" /replace="uracile" /replace="cytosine"
/replace=""
<220> FEATURE:
<221> NAME/KEY: misc_feature
<222> LOCATION: (19)..(19)
<223> OTHER INFORMATION: n is a, c, g, t or u

<400> SEQUENCE: 61
nhhhhrgndb yhythrdhnc yrhhhh 26

<210> SEQ ID NO 62
<211> LENGTH: 26
<212> TYPE: DNA
<213> ORGANISM: Artificial Sequence
<220> FEATURE:
<223> OTHER INFORMATION: histon stem loop sequence according to formula
(IIe)

<400> SEQUENCE: 62
mhwmmrgyky ywytwrrmrc yrymmm 26

<210> SEQ ID NO 63
<211> LENGTH: 26
<212> TYPE: DNA
<213> ORGANISM: Artificial Sequence
<220> FEATURE:
<223> OTHER INFORMATION: histon stem loop sequence according to formula
(IIe)

<400> SEQUENCE: 63
mhwamggcty twytwarmgc cacmmm 26

<210> SEQ ID NO 64
<211> LENGTH: 26
<212> TYPE: DNA
<213> ORGANISM: Artificial Sequence
<220> FEATURE:
<223> OTHER INFORMATION: histon stem loop sequence according to formula
(IIe)

<400> SEQUENCE: 64
acaaaggctt ttttaagagc caccaa 26

<210> SEQ ID NO 65
<211> LENGTH: 26
<212> TYPE: DNA
<213> ORGANISM: Artificial Sequence
<220> FEATURE:
<223> OTHER INFORMATION: histon stem loop sequence according to formula
(IIf)
<220> FEATURE:
<221> NAME/KEY: variation
<222> LOCATION: (26)..(26)
<223> OTHER INFORMATION: /replace="guanine" /replace="adenine"
/replace="thymine" /replace="uracile" /replace="cytosine"
/replace=""

<220> FEATURE:
<221> NAME/KEY: misc_feature
<222> LOCATION: (26)..(26)
<223> OTHER INFORMATION: n is a, c, g, t or u

<400> SEQUENCE: 65
hhhhmvgyyy tyhthryrrc bvmhhn 26

<210> SEQ ID NO 66
<211> LENGTH: 26
<212> TYPE: DNA
<213> ORGANISM: Artificial Sequence
<220> FEATURE:
<223> OTHER INFORMATION: histon stem loop sequence according to formula (IIf)

<400> SEQUENCE: 66
mmmmmsgyyc ttytmagrrc smchhh 26

<210> SEQ ID NO 67
<211> LENGTH: 26
<212> TYPE: DNA
<213> ORGANISM: Artificial Sequence
<220> FEATURE:
<223> OTHER INFORMATION: histon stem loop sequence according to formula (IIf)

<400> SEQUENCE: 67
mmmmmsgyyc ttttmagrrc sachmh 26

<210> SEQ ID NO 68
<211> LENGTH: 26
<212> TYPE: DNA
<213> ORGANISM: Artificial Sequence
<220> FEATURE:
<223> OTHER INFORMATION: histon stem loop sequence according to formula (IIf)

<400> SEQUENCE: 68
mmmmmsgyyy yyytmrrrrc smmmmw 26

<210> SEQ ID NO 69
<211> LENGTH: 26
<212> TYPE: DNA
<213> ORGANISM: Artificial Sequence
<220> FEATURE:
<223> OTHER INFORMATION: histon stem loop sequence according to formula (IIf)

<400> SEQUENCE: 69
mmmmmggcyc ttttcagrgc cacmmw 26

<210> SEQ ID NO 70
<211> LENGTH: 26
<212> TYPE: DNA
<213> ORGANISM: Artificial Sequence
<220> FEATURE:
<223> OTHER INFORMATION: histon stem loop sequence according to formula (IIf)

<400> SEQUENCE: 70
acaacggccc ttttcagggc caccaa 26

<210> SEQ ID NO 71
<211> LENGTH: 26
<212> TYPE: DNA
<213> ORGANISM: Artificial Sequence

```
<220> FEATURE:
<223> OTHER INFORMATION: histon stem loop sequence according to formula
      (IIg)
<220> FEATURE:
<221> NAME/KEY: variation
<222> LOCATION: (24)..(25)
<223> OTHER INFORMATION: /replace="guanine" /replace="adenine"
      /replace="thymine" /replace="uracile"  /replace="cytosine"
      /replace=""
<220> FEATURE:
<221> NAME/KEY: misc_feature
<222> LOCATION: (24)..(25)
<223> OTHER INFORMATION: n is a, c, g, t or u

<400> SEQUENCE: 71

hhvamggyyc ttythagrrc cvhnnm                                          26


<210> SEQ ID NO 72
<211> LENGTH: 26
<212> TYPE: DNA
<213> ORGANISM: Artificial Sequence
<220> FEATURE:
<223> OTHER INFORMATION: histon stem loop sequence according to formula
      (IIg)

<400> SEQUENCE: 72

hhaamggcyc ttytmagrgc cvchhm                                          26


<210> SEQ ID NO 73
<211> LENGTH: 26
<212> TYPE: DNA
<213> ORGANISM: Artificial Sequence
<220> FEATURE:
<223> OTHER INFORMATION: histon stem loop sequence according to formula
      (IIg)

<400> SEQUENCE: 73

mhaamggctc ttttmagrgc cmcymm                                          26


<210> SEQ ID NO 74
<211> LENGTH: 26
<212> TYPE: DNA
<213> ORGANISM: Artificial Sequence
<220> FEATURE:
<223> OTHER INFORMATION: histon stem loop sequence according to formula
      (IIg)

<400> SEQUENCE: 74

mmmmmrgyyy ykytmasrrc bmmymm                                          26


<210> SEQ ID NO 75
<211> LENGTH: 26
<212> TYPE: DNA
<213> ORGANISM: Artificial Sequence
<220> FEATURE:
<223> OTHER INFORMATION: histon stem loop sequence according to formula
      (IIg)

<400> SEQUENCE: 75

mcaamggctc ttttmagagc caccmm                                          26


<210> SEQ ID NO 76
<211> LENGTH: 26
<212> TYPE: DNA
<213> ORGANISM: Artificial Sequence
<220> FEATURE:
<223> OTHER INFORMATION: histon stem loop sequence according to formula
      (IIg)
```

<400> SEQUENCE: 76
acaaaggctc ttttcagagc caccca 26

<210> SEQ ID NO 77
<211> LENGTH: 26
<212> TYPE: DNA
<213> ORGANISM: Artificial Sequence
<220> FEATURE:
<223> OTHER INFORMATION: histon stem loop sequence according to formula (IIh)
<220> FEATURE:
<221> NAME/KEY: variation
<222> LOCATION: (1)..(1)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: variation
<222> LOCATION: (25)..(25)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (25)..(25)
<223> OTHER INFORMATION: n is a, c, g, t or u

<400> SEQUENCE: 77
nhaahkgcyc trythagrrc cvhbnh 26

<210> SEQ ID NO 78
<211> LENGTH: 26
<212> TYPE: DNA
<213> ORGANISM: Artificial Sequence
<220> FEATURE:
<223> OTHER INFORMATION: histon stem loop sequence according to formula (IIh)
<220> FEATURE:
<221> NAME/KEY: variation
<222> LOCATION: (25)..(25)
<223> OTHER INFORMATION: /replace="guanine" /replace="adenine" /replace="thymine" /replace="uracile" /replace="cytosine" /replace=""
<220> FEATURE:
<221> NAME/KEY: misc_feature
<222> LOCATION: (25)..(25)
<223> OTHER INFORMATION: n is a, c, g, t or u

<400> SEQUENCE: 78
hhaamggcyc tttthagrgc cvmynm 26

<210> SEQ ID NO 79
<211> LENGTH: 26
<212> TYPE: DNA
<213> ORGANISM: Artificial Sequence
<220> FEATURE:
<223> OTHER INFORMATION: histon stem loop sequence according to formula (IIh)

<400> SEQUENCE: 79
hmaaaggcyc tttthagrgc crmyhm 26

<210> SEQ ID NO 80
<211> LENGTH: 26
<212> TYPE: DNA
<213> ORGANISM: Artificial Sequence
<220> FEATURE:

<223> OTHER INFORMATION: histon stem loop sequence according to formula
(IIh)

<400> SEQUENCE: 80
mmaamkghyc tkytmasrrc crmyym 26

<210> SEQ ID NO 81
<211> LENGTH: 26
<212> TYPE: DNA
<213> ORGANISM: Artificial Sequence
<220> FEATURE:
<223> OTHER INFORMATION: histon stem loop sequence according to formula
(IIh)

<400> SEQUENCE: 81
mmaamggcyc ttttmagrgc crmyym 26

<210> SEQ ID NO 82
<211> LENGTH: 26
<212> TYPE: DNA
<213> ORGANISM: Artificial Sequence
<220> FEATURE:
<223> OTHER INFORMATION: histon stem loop sequence according to formula
(IIh)

<400> SEQUENCE: 82
ccaaaggctc ttttcagagc caccca 26

<210> SEQ ID NO 83
<211> LENGTH: 1747
<212> TYPE: DNA
<213> ORGANISM: Artificial Sequence
<220> FEATURE:
<223> OTHER INFORMATION: ppLuc(GC) - ag

<400> SEQUENCE: 83
gggagaaagc uugaggaugg aggacgccaa gaacaucaag aagggcccgg cgcccuucua 60
cccgcuggag gacgggaccg ccggcgagca gcuccacaag gccaugaagc gguacgcccu 120
ggugccgggc acgaucgccu ucaccgacgc ccacaucgag gucgacauca ccuacgcgga 180
guacuucgag augagcgugc gccuggccga ggccaugaag cgguacggcc ugaacaccaa 240
ccaccggauc guggugugcu cggagaacag ccugcaguuc uucaugccgg ugcugggcgc 300
ccucuucauc ggcguggccg ucgccccggc gaacgacauc uacaacgagc gggagcugcu 360
gaacagcaug ggaucagcc agccgaccgu gguguucgug agcaagaagg gccugcagaa 420
gauccugaac gugcagaaga agcugcccau cauccagaag aucaucauca uggacagcaa 480
gaccgacuac cagggcuucc agucgaugua cacguucgug accagccacc ucccgccggg 540
cuucaacgag uacgacuucg ucccggagag cuucgaccgg gacaagacca ucgcccugau 600
caugaacagc agcggcagca ccggccugcc gaagggggug gcccugccgc accggaccgc 660
cugcgugcgc uucucgcacg cccgggaccc caucuucggc aaccagauca ucccggacac 720
cgccauccug agcguggugc cguuccacca cggcuucggc auguucacga cccugggcua 780
ccucaucugc ggcuuccggg ugguccugau guaccgguuc gaggaggagc uguuccugcg 840
gagccugcag gacuacaaga uccagagcgc gcugcucgug ccgacccugu ucagcuucuu 900
cgccaagagc acccugaucg acaaguacga ccugucgaac cugcacgaga ucgccagcgg 960
gggcgccccg cugagcaagg aggugggcga ggccguggcc aagcgguucc accucccggg 1020
cauccgccag ggcuacggcc ugaccgagac cacgagcgcg auccugauca cccccgaggg 1080

-continued

```
ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcggugu ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auagauc                                                             1747
```

<210> SEQ ID NO 84
<211> LENGTH: 1806
<212> TYPE: DNA
<213> ORGANISM: Artificial Sequence
<220> FEATURE:
<223> OTHER INFORMATION: ppLuc(GC) - ag - A64

<400> SEQUENCE: 84

```
gggagaaagc uugaggaugg aggacgccaa gaacaucaag aagggcccgg cgcccuucua     60

cccgcuggag gacgggaccg ccggcgagca gcuccacaag gccaugaagc gguacgcccu    120

ggugccgggc acgaucgccu ucaccgacgc ccacaucgag gucgacauca ccuacgcgga    180

guacuucgag augagcgugc gccuggccga ggccaugaag cgguacggcc ugaacaccaa    240

ccaccggauc guggugugcu cggagaacag ccugcaguuc uucaugccgg ugcugggcgc    300

ccucuucauc ggcguggccg ucgccccggc gaacgacauc uacaacgagc gggagcugcu    360

gaacagcaug ggaucagcc agccgaccgu gguguucgug agcaagaagg gccugcagaa    420

gauccugaac gugcagaaga agcugcccau cauccagaag aucaucauca uggacagcaa    480

gaccgacuac cagggcuucc agucgaugua cacguucgug accagccacc ucccgccggg    540

cuucaacgag uacgacuucg ucccggagag cuucgaccgg gacaagacca ucgcccugau    600

caugaacagc agcggcagca ccggccugcc gaagggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780

ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960

gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380
```

-continued

```
gagcauccug cuccagcacc ccaacaucuu cgacgccggc guggccgggc ugccggacga   1440

cgacgccggc gagcugccgg ccgcggugu ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaa                                                               1806


<210> SEQ ID NO 85
<211> LENGTH: 1772
<212> TYPE: DNA
<213> ORGANISM: Artificial Sequence
<220> FEATURE:
<223> OTHER INFORMATION: ppLuc(GC) - ag - histoneSL

<400> SEQUENCE: 85

gggagaaagc uugaggaugg aggacgccaa gaacaucaag aagggcccgg cgcccuucua     60

cccgcuggag gacgggaccg ccggcgagca gcuccacaag gccaugaagc gguacgcccu    120

ggugccgggc acgaucgccu ucaccgacgc ccacaucgag gucgacauca ccuacgcgga    180

guacuucgag augagcgugc gccuggccga ggccaugaag cgguacggcc ugaacaccaa    240

ccaccggauc guggugugcu cggagaacag ccugcaguuc uucaugccgg ugcugggcgc    300

ccucuucauc ggcguggccg ucgccccggc gaacgacauc uacaacgagc gggagcugcu    360

gaacagcaug ggaucagcc agccgaccgu gguguucgug agcaagaagg gccugcagaa    420

gauccugaac gugcagaaga agcugcccau cauccagaag aucaucauca uggacagcaa    480

gaccgacuac cagggcuucc agucgaugua cacguucgug accagccacc ucccgccggg    540

cuucaacgag uacgacuucg ucccggagag cuucgaccgg gacaagacca ucgcccugau    600

caugaacagc agcggcagca ccggccugcc gaaggggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780

ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960

gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcggugu ggugcuggag cacggcaaga ccaugacgga   1500

gaaggagauc gucgacuacg uggccagcca ggugaccacc gccaagaagc ugcggggcgg   1560
```

```
cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auagaucuca aaggcucuuu ucagagccac ca                                 1772


<210> SEQ ID NO 86
<211> LENGTH: 1835
<212> TYPE: DNA
<213> ORGANISM: Artificial Sequence
<220> FEATURE:
<223> OTHER INFORMATION: ppLuc(GC) - ag - A64 - histoneSL

<400> SEQUENCE: 86

gggagaaagc uugaggaugg aggacgccaa gaacaucaag aagggcccgg cgcccuucua     60

cccgcuggag gacgggaccg ccggcgagca gcuccacaag gccaugaagc gguacgcccu    120

ggugccgggc acgaucgccu ucaccgacgc ccacaucgag gucgacauca ccuacgcgga    180

guacuucgag augagcgugc gccuggccga ggccaugaag cgguacggcc ugaacaccaa    240

ccaccggauc guggugugcu cggagaacag ccugcaguuc uucaugccgg ugcugggcgc    300

ccucuucauc ggcguggccg ucgccccggc gaacgacauc uacaacgagc gggagcugcu    360

gaacagcaug ggaucagcc agccgaccgu gguguucgug agcaagaagg gccugcagaa    420

gauccugaac gugcagaaga agcugcccau cauccagaag aucaucauca uggacagcaa    480

gaccgacuac cagggcuucc agucgaugua cacguucgug accagccacc ucccgccggg    540

cuucaacgag uacgacuucg ucccggagag cuucgaccgg gacaagacca ucgcccugau    600

caugaacagc agcggcagca ccggccugcc gaagggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780

ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960

gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcggugu ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaaugca ucaaaggcuc uuuucagagc cacca                              1835
```

<210> SEQ ID NO 87
<211> LENGTH: 1869
<212> TYPE: DNA
<213> ORGANISM: Artificial Sequence
<220> FEATURE:
<223> OTHER INFORMATION: ppLuc(GC) - ag - A120

<400> SEQUENCE: 87
gggagaaagc uugaggaugg aggacgccaa gaacaucaag aagggcccgg cgcccuucua 60
cccgcuggag gacgggaccg ccggcgagca gcuccacaag gccaugaagc gguacgcccu 120
ggugccgggc acgaucgccu ucaccgacgc ccacaucgag gucgacauca ccuacgcgga 180
guacuucgag augagcgugc gccuggccga ggccaugaag cgguacggcc ugaacaccaa 240
ccaccggauc guggugugcu cggagaacag ccugcaguuc uucaugccgg ugcugggcgc 300
ccucuucauc ggcguggccg ucgccccggc gaacgacauc uacaacgagc gggagcugcu 360
gaacagcaug ggaucagcc agccgaccgu gguguucgug agcaagaagg gccugcagaa 420
gauccugaac gugcagaaga agcugcccau cauccagaag aucaucauca uggacagcaa 480
gaccgacuac cagggcuucc agucgaugua cacguucgug accagccacc ucccgccggg 540
cuucaacgag uacgacuucg ucccggagag cuucgaccgg gacaagacca ucgcccugau 600
caugaacagc agcggcagca ccggccugcc gaagggggug gcccugccgc accggaccgc 660
cugcgugcgc uucucgcacg cccgggaccc caucuucggc aaccagauca ucccggacac 720
cgccauccug agcguggugc cguuccacca cggcuucggc auguucacga cccugggcua 780
ccucaucugc ggcuuccggg ugguccugau guaccgguuc gaggaggagc uguuccugcg 840
gagccugcag gacuacaaga uccagagcgc gcugcucgug ccgacccugu ucagcuucuu 900
cgccaagagc acccugaucg acaaguacga ccugucgaac cugcacgaga ucgccagcgg 960
gggcgccccg cugagcaagg aggugggcga ggccguggcc aagcgguucc accucccggg 1020
cauccgccag ggcuacggcc ugaccgagac cacgagcgcg auccugauca cccccgaggg 1080
ggacgacaag ccgggcgccg ugggcaaggu gguccccguuc uucgaggcca agguggugga 1140
ccuggacacc ggcaagaccc ugggcgugaa ccagcggggc gagcugugcg ugcgggggcc 1200
gaugaucaug agcggcuacg ugaacaaccc ggaggccacc aacgcccuca ucgacaagga 1260
cggcuggcug cacagcggcg acaucgccua cugggacgag gacgagcacu ucuucaucgu 1320
cgaccggcug aagucgcuga ucaaguacaa gggcuaccag guggcgccgg ccgagcugga 1380
gagcauccug cuccagcacc ccaacaucuu cgacgccggc guggccgggc ugccggacga 1440
cgacgccggc gagcugccgg ccgcggugu gguggcuggag cacggcaaga ccaugacgga 1500
gaaggagauc gucgacuacg uggccagcca ggugaccacc gccaagaagc ugcggggcgg 1560
cgugguguuc guggacgagg ucccgaaggg ccugaccggg aagcucgacg cccggaagau 1620
ccgcgagauc cugaucaagg ccaagaaggg cggcaagauc gccguguaag acuaguuaua 1680
agacugacua gcccgauggg ccucccaacg ggcccuccuc cccuccuugc accgagauua 1740
auagaucuaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaa 1869

<210> SEQ ID NO 88
<211> LENGTH: 1858
<212> TYPE: DNA

```
<213> ORGANISM: Artificial Sequence
<220> FEATURE:
<223> OTHER INFORMATION: ppLuc(GC) - ag - A64 - ag

<400> SEQUENCE: 88

gggagaaagc uugaggaugg aggacgccaa gaacaucaag aagggcccgg cgcccuucua      60

cccgcuggag gacgggaccg ccggcgagca gcuccacaag gccaugaagc gguacgcccu     120

ggugccgggc acgaucgccu ucaccgacgc ccacaucgag gucgacauca ccuacgcgga     180

guacuucgag augagcgugc gccuggccga ggccaugaag cgguacggcc ugaacaccaa     240

ccaccggauc guggugugcu cggagaacag ccugcaguuc uucaugccgg ugcugggcgc     300

ccucuucauc ggcguggccg ucgccccggc gaacgacauc uacaacgagc gggagcugcu     360

gaacagcaug ggaucagcc agccgaccgu gguguucgug agcaagaagg gccugcagaa     420

gauccugaac gugcagaaga agcugcccau cauccagaag aucaucauca uggacagcaa     480

gaccgacuac cagggcuucc agucgaugua cacguucgug accagccacc ucccgccggg     540

cuucaacgag uacgacuucg ucccggagag cuucgaccgg gacaagacca ucgcccugau     600

caugaacagc agcggcagca ccggccugcc gaagggggug gcccugccgc accggaccgc     660

cugcgugcgc uucucgcacg cccgggaccc caucuucggc aaccagauca ucccggacac     720

cgccauccug agcguggugc cguuccacca cggcuucggc auguucacga cccugggcua     780

ccucaucugc ggcuuccggg ugguccugau guaccgguuc gaggaggagc uguuccugcg     840

gagccugcag gacuacaaga uccagagcgc gcugcucgug ccgacccugu ucagcuucuu     900

cgccaagagc acccugaucg acaaguacga ccugucgaac cugcacgaga ucgccagcgg     960

gggcgccccg cugagcaagg aggugggcga ggccguggcc aagcgguucc accucccggg    1020

cauccgccag ggcuacggcc ugaccgagac cacgagcgcg auccugauca cccccgaggg    1080

ggacgacaag ccgggcgccg ugggcaaggu gguccccguuc uucgaggcca agguggugga    1140

ccuggacacc ggcaagaccc ugggcgugaa ccagcggggc gagcugugcg ugcgggggcc    1200

gaugaucaug agcggcuacg ugaacaaccc ggaggccacc aacgcccuca ucgacaagga    1260

cggcuggcug cacagcggcg acaucgccua cugggacgag gacgagcacu ucuucaucgu    1320

cgaccggcug aagucgcuga ucaaguacaa gggcuaccag guggcgccgg ccgagcugga    1380

gagcauccug cuccagcacc ccaacaucuu cgacgccggc guggccgggc ugccggacga    1440

cgacgccggc gagcugccgg ccgcggugu ggugcuggag cacggcaaga ccaugacgga    1500

gaaggagauc gucgacuacg uggccagcca ggugaccacc gccaagaagc ugcggggcgg    1560

cgugguguuc guggacgagg ucccgaaggg ccugaccggg aagcucgacg cccggaagau    1620

ccgcgagauc cugaucaagg ccaagaaggg cggcaagauc gccguguaag acuaguuaua    1680

agacugacua gcccgauggg ccucccaacg ggcccuccuc cccuccuugc accgagauua    1740

auaaaaaaaa aaaaaaaaaa aaaaaaaaaa aaaaaaaaaa aaaaaaaaaa aaaaaaaaaa    1800

aaaaaaugca uccugcccga ugggccuccc aacgggcccu ccuccccucc uugcaccg      1858


<210> SEQ ID NO 89
<211> LENGTH: 1894
<212> TYPE: DNA
<213> ORGANISM: Artificial Sequence
<220> FEATURE:
<223> OTHER INFORMATION: ppLuc(GC) - ag - A64 - aCPSL

<400> SEQUENCE: 89

gggagaaagc uugaggaugg aggacgccaa gaacaucaag aagggcccgg cgcccuucua      60
```

-continued cccgcuggag gacgggaccg ccggcgagca gcuccacaag gccaugaagc gguacgcccu 120
ggugccgggc acgaucgccu ucaccgacgc ccacaucgag gucgacauca ccuacgcgga 180
guacuucgag augagcgugc gccuggccga ggccaugaag cgguacggcc ugaacaccaa 240
ccaccggauc guggugugcu cggagaacag ccugcaguuc uucaugccgg ugcugggcgc 300
ccucuucauc ggcguggccg ucgccccggc gaacgacauc uacaacgagc gggagcugcu 360
gaacagcaug ggcaucagcc agccgaccgu gguguucgug agcaagaagg gccugcagaa 420
gauccugaac gugcagaaga agcugcccau cauccagaag aucaucauca uggacagcaa 480
gaccgacuac cagggcuucc agucgaugua cacguucgug accagccacc ucccgccggg 540
cuucaacgag uacgacuucg ucccggagag cuucgaccgg gacaagacca ucgcccugau 600
caugaacagc agcggcagca ccggccugcc gaagggggug gcccugccgc accggaccgc 660
cugcgugcgc uucucgcacg cccgggaccc caucuucggc aaccagauca ucccggacac 720
cgccauccug agcguggugc cguuccacca cggcuucggc auguucacga cccugggcua 780
ccucaucugc ggcuuccggg ugguccugau guaccgguuc gaggaggagc uguuccugcg 840
gagccugcag gacuacaaga uccagagcgc gcugcucgug ccgacccugu ucagcuucuu 900
cgccaagagc acccugaucg acaaguacga ccugucgaac cugcacgaga ucgccagcgg 960
gggcgccccg cugagcaagg aggugggcga ggccguggcc aagcgguucc accucccggg 1020
cauccgccag ggcuacggcc ugaccgagac cacgagcgcg auccugauca cccccgaggg 1080
ggacgacaag ccgggcgccg ugggcaaggu gguccccguuc uucgaggcca agguggugga 1140
ccuggacacc ggcaagaccc ugggcgugaa ccagcggggc gagcugugcg ugcgggggcc 1200
gaugaucaug agcggcuacg ugaacaaccc ggaggccacc aacgcccuca ucgacaagga 1260
cggcuggcug cacagcggcg acaucgccua cugggacgag gacgagcacu ucuucaucgu 1320
cgaccggcug aagucgcuga ucaaguacaa gggcuaccag guggcgccgg ccgagcugga 1380
gagcauccug cuccagcacc ccaacaucuu cgacgccggc guggccgggc ugccggacga 1440
cgacgccggc gagcugccgg ccgcggugu ggugcuggag cacggcaaga ccaugacgga 1500
gaaggagauc gucgacuacg uggccagcca ggugaccacc gccaagaagc ugcggggcgg 1560
cgugguguuc guggacgagg ucccgaaggg ccugaccggg aagcucgacg cccggaagau 1620
ccgcgagauc cugaucaagg ccaagaaggg cggcaagauc gccguguaag acuaguuaua 1680
agacugacua gcccgauggg ccucccaacg ggcccuccuc cccuccuugc accgagauua 1740
auaaaaaaaa aaaaaaaaaa aaaaaaaaaa aaaaaaaaaa aaaaaaaaaa aaaaaaaaaa 1800
aaaaaaugca ucaauuccua cacgugaggc gcugugauuc ccuaucccccc uucauucccu 1860 auacauuagc acagcgccau ugcauguagg aauu 1894

<210> SEQ ID NO 90
<211> LENGTH: 1909
<212> TYPE: DNA
<213> ORGANISM: Artificial Sequence
<220> FEATURE:
<223> OTHER INFORMATION: ppLuc(GC) - ag - A64 - PolioCL

<400> SEQUENCE: 90
gggagaaagc uugaggaugg aggacgccaa gaacaucaag aagggcccgg cgcccuucua 60
cccgcuggag gacgggaccg ccggcgagca gcuccacaag gccaugaagc gguacgcccu 120
ggugccgggc acgaucgccu ucaccgacgc ccacaucgag gucgacauca ccuacgcgga 180

-continued

```
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug ggaucagcc agccgaccgu gguguucgug agcaagaagg gccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccugcc gaagggggug gcccugccgc accggaccgc    660
cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu gguccccguuc uucgaggcca agguggugga   1140
ccuggacacc ggcaagaccc ugggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcggugu ggugcuggag cacggcaaga ccaugacgga   1500
gaaggagauc gucgacuacg uggccagcca ggugaccacc gccaagaagc ugcggggcgg   1560
cgugguguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggcccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca ucaauucuaa aacagcucug ggguuguacc caccccagag gcccacgugg   1860
cggcuaguac uccgguauug cgguacccuu guacgccugu uuuagaauu               1909
```

<210> SEQ ID NO 91
<211> LENGTH: 1841
<212> TYPE: DNA
<213> ORGANISM: Artificial Sequence
<220> FEATURE:
<223> OTHER INFORMATION: ppLuc(GC) - ag - A64 - G30

<400> SEQUENCE: 91

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
```

gaacagcaug gggaucagcc agccgaccgu gguguucgug agcaagaagg gccugcagaa 420
gauccugaac gugcagaaga agcugcccau cauccagaag aucaucauca uggacagcaa 480
gaccgacuac cagggcuucc agucgaugua cacguucgug accagccacc ucccgccggg 540
cuucaacgag uacgacuucg ucccggagag cuucgaccgg gacaagacca ucgcccugau 600
caugaacagc agcggcagca ccggccugcc gaagggggug gcccugccgc accggaccgc 660
cugcgugcgc uucucgcacg cccgggaccc caucuucggc aaccagauca ucccggacac 720
cgccauccug agcguggugc cguuccacca cggcuucggc auguucacga cccugggcua 780
ccucaucugc ggcuuccggg ugguccugau guaccgguuc gaggaggagc uguuccugcg 840
gagccugcag gacuacaaga uccagagcgc gcugcucgug ccgacccugu ucagcuucuu 900
cgccaagagc acccugaucg acaaguacga ccugucgaac cugcacgaga ucgccagcgg 960
gggcgccccg cugagcaagg aggugggcga ggccguggcc aagcgguucc accucccggg 1020
cauccgccag ggcuacggcc ugaccgagac cacgagcgcg auccugauca cccccgaggg 1080
ggacgacaag ccgggcgccg ugggcaaggu ggucccguuc uucgaggcca agguggugga 1140
ccuggacacc ggcaagaccc ugggcgugaa ccagcggggc gagcugugcg ugcgggggcc 1200
gaugaucaug agcggcuacg ugaacaaccc ggaggccacc aacgcccuca ucgacaagga 1260
cggcuggcug cacagcggcg acaucgccua cugggacgag gacgagcacu ucuucaucgu 1320
cgaccggcug aagucgcuga ucaaguacaa gggcuaccag guggcgccgg ccgagcugga 1380
gagcauccug cuccagcacc ccaacaucuu cgacgccggc guggccgggc ugccggacga 1440
cgacgccggc gagcugccgg ccgcggugg ggugcuggag cacggcaaga ccaugacgga 1500
gaaggagauc gucgacuacg uggccagcca ggugaccacc gccaagaagc ugcggggcgg 1560
cgugguguuc guggacgagg ucccgaaggg ccugaccggg aagcucgacg cccggaagau 1620
ccgcgagauc cugaucaagg ccaagaaggg cggcaagauc gccguguaag acuaguuaua 1680
agacugacua gcccgauggg ccucccaacg ggcccuccuc cccuccuugc accgagauua 1740
auaaaaaaaa aaaaaaaaaa aaaaaaaaaa aaaaaaaaaa aaaaaaaaaa aaaaaaaaaa 1800
aaaaaaugca uggggggggg gggggggggg gggggggggg g 1841

<210> SEQ ID NO 92
<211> LENGTH: 1841
<212> TYPE: DNA
<213> ORGANISM: Artificial Sequence
<220> FEATURE:
<223> OTHER INFORMATION: ppLuc(GC) - ag - A64 - U30

<400> SEQUENCE: 92
gggagaaagc uugaggaugg aggacgccaa gaacaucaag aagggcccgg cgcccuucua 60
cccgcuggag gacgggaccg ccggcgagca gcuccacaag gccaugaagc gguacgcccu 120
ggugccgggc acgaucgccu ucaccgacgc ccacaucgag gucgacauca ccuacgcgga 180
guacuucgag augagcgugc gccuggccga ggccaugaag cgguacggcc ugaacaccaa 240
ccaccggauc guggugugcu cggagaacag ccugcaguuc uucaugccgg ugcugggcgc 300
ccucuucauc ggcguggccg ucgccccggc gaacgacauc uacaacgagc gggagcugcu 360
gaacagcaug gggaucagcc agccgaccgu gguguucgug agcaagaagg gccugcagaa 420
gauccugaac gugcagaaga agcugcccau cauccagaag aucaucauca uggacagcaa 480
gaccgacuac cagggcuucc agucgaugua cacguucgug accagccacc ucccgccggg 540

-continued

```
cuucaacgag uacgacuucg ucccggagag cuucgaccgg gacaagacca ucgcccugau    600

caugaacagc agcggcagca ccggccugcc gaagggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780

ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960

gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcggugga ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaaugca uuuuuuuuuu uuuuuuuuuu uuuuuuuuuu u                       1841
```

<210> SEQ ID NO 93
<211> LENGTH: 1857
<212> TYPE: DNA
<213> ORGANISM: Artificial Sequence
<220> FEATURE:
<223> OTHER INFORMATION: ppLuc(GC) - ag - A64 - SL

<400> SEQUENCE: 93

```
gggagaaagc uugaggaugg aggacgccaa gaacaucaag aagggcccgg cgcccuucua     60

cccgcuggag gacgggaccg ccggcgagca gcuccacaag gccaugaagc gguacgcccu    120

ggugccgggc acgaucgccu ucaccgacgc ccacaucgag gucgacauca ccuacgcgga    180

guacuucgag augagcgugc gccuggccga ggccaugaag cgguacggcc ugaacaccaa    240

ccaccggauc guggugugcu cggagaacag ccugcaguuc uucaugccgg ugcugggcgc    300

ccucuucauc ggcguggccg ucgccccggc gaacgacauc uacaacgagc gggagcugcu    360

gaacagcaug gggaucagcc agccgaccgu gguguucgug agcaagaagg gccugcagaa    420

gauccugaac gugcagaaga agcugcccau cauccagaag aucaucauca uggacagcaa    480

gaccgacuac cagggcuucc agucgaugua cacguucgug accagccacc ucccgccggg    540

cuucaacgag uacgacuucg ucccggagag cuucgaccgg gacaagacca ucgcccugau    600

caugaacagc agcggcagca ccggccugcc gaagggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780
```

```
ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960

gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu ggucccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgcccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcgguggu ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaaugca uuauggcggc cguguccacc acggauauca ccguggugga cgcggcc      1857
```

<210> SEQ ID NO 94
<211> LENGTH: 1838
<212> TYPE: DNA
<213> ORGANISM: Artificial Sequence
<220> FEATURE:
<223> OTHER INFORMATION: ppLuc(GC) - ag - A64 - N32

<400> SEQUENCE: 94

```
gggagaaagc uugaggaugg aggacgccaa gaacaucaag aagggcccgg cgcccuucua     60

cccgcuggag gacgggaccg ccggcgagca gcuccacaag gccaugaagc gguacgcccu    120

ggugccgggc acgaucgccu ucaccgacgc ccacaucgag gucgacauca ccuacgcgga    180

guacuucgag augagcgugc gccuggccga ggccaugaag cgguacggcc ugaacaccaa    240

ccaccggauc gugguguguc cggagaacag ccugcaguuc uucaugccgg ugcugggcgc    300

ccucuucauc ggcguggccg ucgccccggc gaacgacauc uacaacgagc gggagcugcu    360

gaacagcaug ggaucagcc agccgaccgu gguguucgug agcaagaagg gccugcagaa    420

gauccugaac gugcagaaga agcugcccau cauccagaag aucaucauca uggacagcaa    480

gaccgacuac cagggcuucc agucgaugua cacguucgug accagccacc ucccgccggg    540

cuucaacgag uacgacuucg ucccggagag cuucgaccgg gacaagacca ucgcccugau    600

caugaacagc agcggcagca ccggccugcc gaaggggggug gcccugccgc accggaccgc    660

cugcgugcgc uucucgcacg cccgggaccc caucuucggc aaccagauca ucccggacac    720

cgccauccug agcguggugc cguuccacca cggcuucggc auguucacga cccugggcua    780

ccucaucugc ggcuuccggg ugguccugau guaccgguuc gaggaggagc uguuccugcg    840

gagccugcag gacuacaaga uccagagcgc gcugcucgug ccgacccugu ucagcuucuu    900

cgccaagagc acccugaucg acaaguacga ccugucgaac cugcacgaga ucgccagcgg    960
```

-continued

```
gggcgccccg cugagcaagg aggugggcga ggccguggcc aagcgguucc accucccggg   1020

cauccgccag ggcuacggcc ugaccgagac cacgagcgcg auccugauca cccccgaggg   1080

ggacgacaag ccgggcgccg ugggcaaggu gguccccguuc uucgaggcca agguggugga   1140

ccuggacacc ggcaagaccc ugggcgugaa ccagcggggc gagcugugcg ugcgggggcc   1200

gaugaucaug agcggcuacg ugaacaaccc ggaggccacc aacgccccuca ucgacaagga   1260

cggcuggcug cacagcggcg acaucgccua cugggacgag gacgagcacu ucuucaucgu   1320

cgaccggcug aagucgcuga ucaaguacaa gggcuaccag guggcgccgg ccgagcugga   1380

gagcauccug cuccagcacc ccaacaucuu cgacgccggc guggccgggc ugccggacga   1440

cgacgccggc gagcugccgg ccgcggugguu ggugcuggag cacggcaaga ccaugacgga   1500

gaaggagauc gucgacuacg uggccagcca ggugaccacc gccaagaagc ugcggggcgg   1560

cgugguguuc guggacgagg ucccgaaggg ccugaccggg aagcucgacg cccggaagau   1620

ccgcgagauc cugaucaagg ccaagaaggg cggcaagauc gccguguaag acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaaugca ucccccucua gacaauugga auuccaua                             1838
```

```
<210> SEQ ID NO 95
<211> LENGTH: 15
<212> TYPE: RNA
<213> ORGANISM: Artificial
<220> FEATURE:
<223> OTHER INFORMATION: Description of sequence: generic stabilizing
      sequence of the formula (C/U)CCANxCCC(U/A)PyxUC(C/U)CC
<220> FEATURE:
<221> NAME/KEY: variation
<222> LOCATION: (1)..(1)
<223> OTHER INFORMATION: /replace="cytosine" /replace="uracile"
<220> FEATURE:
<221> NAME/KEY: misc_feature
<222> LOCATION: (1)..(1)
<223> OTHER INFORMATION: nucleic acid = cytosine or uracil
<220> FEATURE:
<221> NAME/KEY: misc_feature
<222> LOCATION: (5)..(5)
<223> OTHER INFORMATION: Nx = a, g, c or u or any other nucleic acid
<220> FEATURE:
<221> NAME/KEY: variation
<222> LOCATION: (5)..(5)
<223> OTHER INFORMATION: /replace="cytosine" /replace="uracile"
      /replace="guanosine" /replace="adenosine", or any other nucle
      ic acid
<220> FEATURE:
<221> NAME/KEY: repeat_unit
<222> LOCATION: (5)..(5)
<223> OTHER INFORMATION: x = any number
<220> FEATURE:
<221> NAME/KEY: misc_feature
<222> LOCATION: (9)..(9)
<223> OTHER INFORMATION: nucleic acid = uracil or adenosine
<220> FEATURE:
<221> NAME/KEY: variation
<222> LOCATION: (9)..(9)
<223> OTHER INFORMATION: /replace="uracile" /replace="adonosine"
<220> FEATURE:
<221> NAME/KEY: misc_feature
<222> LOCATION: (10)..(10)
<223> OTHER INFORMATION: Py = pyrimidine
<220> FEATURE:
<221> NAME/KEY: repeat_unit
<222> LOCATION: (10)..(10)
<223> OTHER INFORMATION: x = any number
<220> FEATURE:
<221> NAME/KEY: variation
<222> LOCATION: (10)..(10)
```

-continued

```
<223> OTHER INFORMATION: /replace="pyrimidine"
<220> FEATURE:
<221> NAME/KEY: misc_feature
<222> LOCATION: (13)..(13)
<223> OTHER INFORMATION: nucleic acid = cytosine or uracil
<220> FEATURE:
<221> NAME/KEY: variation
<222> LOCATION: (13)..(13)
<223> OTHER INFORMATION: /replace="cytosine" /replace="uracile"

<400> SEQUENCE: 95

nccancccnn ucncc                                                 15
```

NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED PROTEIN

This application is a continuation of U.S. application Ser. No. 13/321,474, filed Apr. 26, 2012, which is a national phase application under 35 U.S.C. §371 of International Application No. PCT/EP2011/004077, filed Aug. 12, 2011, which claims benefit of International Application No. PCT/EP2010/004998, filed Aug. 13, 2010. The entire text of each of the above referenced disclosures is specifically incorporated herein by reference.

The present application describes a coding nucleic acid sequence, particularly a messenger RNA (mRNA), comprising or coding for a histone stem-loop and a poly(A) sequence or a polyadenylation signal and the use thereof for increasing the expression of an encoded protein. It also discloses its use for the preparation of a pharmaceutical composition, especially a vaccine, e.g. for use in the treatment of tumours and cancer diseases, cardiovascular diseases, infectious diseases, autoimmune diseases or genetic diseases, or in gene therapy. The present invention further describes an in vitro transcription method, in vitro methods for increasing the expression of a protein using the nucleic acid comprising or coding for a histone stem-loop and a poly(A) sequence or a polyadenylation signal and an ex vivo and in vivo method.

Apart from cardiovascular diseases and infectious diseases, the occurrence of tumours and cancer diseases is one of the most frequent causes of death in modern society and is in most cases associated with considerable costs in terms of therapy and subsequent rehabilitation measures. The treatment of tumours and cancer diseases is greatly dependent, for example, on the type of tumour that occurs, on the age, the distribution of cancer cells in the patient to be treated, etc. Cancer therapy is nowadays conventionally carried out by the use of radiation therapy or chemotherapy in addition to invasive operations. However, such conventional therapies typically place extraordinary stress on the immune system and can be used in some cases to only a limited extent. In addition, most of these conventional therapies require long intervals between the individual treatments to allow for regeneration of the immune system.

Therefore, supplementary strategies have been investigated in recent years in addition to such "conventional treatments" to avoid or at least reduce the impact on the immune system by such treatments. One such supplementary treatment in particular includes gene therapeutic approaches or genetic vaccination, which already have been found to be highly promising for treatment or for supporting such conventional therapies.

Gene therapy and genetic vaccination are methods of molecular medicine which already have been proven in the therapy and prevention of diseases and generally exhibit a considerable effect on daily medical practice, in particular on the treatment of diseases as mentioned above. Gene therapy is also used in further fields of medicine, e.g. in the case of genetic diseases, that is to say (inherited) diseases, that are caused by a defined gene defect and are inherited according to Mendel's laws. The most well known representatives of such genetic diseases include inter alia mucoviscidosis (cystic fibrosis) and sickle cell anaemia. Both methods, gene therapy and genetic vaccination, are based on the introduction of nucleic acids into the patient's cells or tissue and subsequent processing of the information coded for by the nucleic acid that has been introduced into the cells or tissue, that is to say the (protein) expression of the desired polypeptides.

In gene therapy approaches, typically DNA is used even though RNA is also known in recent developments. Importantly, in all these gene therapy approaches mRNA functions as messenger for the sequence information of the encoded protein, irrespectively if DNA, viral RNA or mRNA is used.

In general RNA is considered an unstable molecule: RNases are ubiquitous and notoriously difficult to inactivate. Furthermore, RNA is also chemically more labile than DNA. Thus, it is perhaps surprising that the "default state" of an mRNA in a eukaryotic cell is characterized by a relative stability and specific signals are required to accelerate the decay of individual mRNAs. The main reason for this finding appears to be that mRNA decay within cells is catalyzed almost exclusively by exonucleases. However, the ends of eukaryotic mRNAs are protected against these enzymes by specific terminal structures and their associated proteins: a m7GpppN CAP at the 5' end and typically a poly(A) sequence at the 3' end. Removal of these two terminal modifications is thus considered rate limiting for mRNA decay. Although a stabilizing element has been characterized in the 3' UTR of the alpha-globin mRNA, RNA sequences affecting turnover of eukaryotic mRNAs typically act as a promoter of decay usually by accelerating deadenylation (reviewed in Meyer, S., C. Temme, et al. (2004), Crit Rev Biochem Mol Biol 39(4): 197-216.).

As mentioned above, the 5' ends of eukaryotic mRNAs are typically modified posttranscriptionally to carry a methylated CAP structure, e.g. m7GpppN. Aside from roles in RNA splicing, stabilization, and transport, the CAP structure significantly enhances the recruitment of the 40S ribosomal subunit to the 5' end of the mRNA during translation initiation. The latter function requires recognition of the CAP structure by the eukaryotic initiation factor complex elF4F. The poly(A) sequence additionally stimulates translation via increased 40S subunit recruitment to mRNAs, an effect that requires the intervention of poly(A) binding protein (PABP). PABP, in turn, was recently demonstrated to interact physically with elF4G, which is part of the CAP-bound elF4F complex. Thus, a closed loop model of translation initiation on capped, polyadenylated mRNAs was postulated (Michel, Y. M., D. Poncet, et al. (2000), J Biol Chem 275(41): 32268-76.).

Nearly all eukaryotic mRNAs end with such a poly(A) sequence that is added to their 3' end by the ubiquitous cleavage/polyadenylation machinery. The presence of a poly (A) sequence at the 3' end is one of the most recognizable features of eukaryotic mRNAs. After cleavage, most pre-mRNAs, with the exception of replication-dependent histone transcripts, acquire a polyadenylated tail. In this context, 3' end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and depends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90.).

The only known exception to this rule are the replication-dependent histone mRNAs which end with a histone stem-loop instead of a poly(A) sequence. Exemplary histone stem-loop sequences are described in Lopez et al. (Dávila López, M., & Samuelsson, T. (2008), RNA (New York, N.Y.), 14(1), 1-10. doi:10.1261/rna.782308.).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the U7 snRNP through base pairing of the U7 snRNA with the HDE.

Due to the requirement to package newly synthesized DNA into chromatin, histone synthesis is regulated in concert with the cell cycle. Increased synthesis of histone proteins during S phase is achieved by transcriptional activation of histone genes as well as posttranscriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell-cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), *Molecular and Cellular Biology,* 14(3), 1709-1720 and Williams, A. S., & Marzluff, W. F., (1995), *Nucleic Acids Research,* 23(4), 654-662.).

Even though histone genes are generally classified as either “replication-dependent”, giving rise to mRNA ending in a histone stem-loop, or “replacement-type”, giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during *Xenopus oogenesis* using Luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha Globin, taking advantage of the fact that the globin gene contains introns as opposed to the intron-less histone genes. For this purpose constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070; Pandey, N. B., & Marzluff, W. F. (1987). Molecular and Cellular Biology, 7(12), 4557-4559; Pandey, N. B., et al. (1990). Nucleic Acids Research, 18(11), 3161-3170).

In another approach Lüscher et al. investigated the cell-cycle dependent regulation of a recombinant histone H4 gene. Constructs were generated in which the H4 coding sequence was followed by a histone stem-loop signal and a polyadenylation signal, the two processing signals incidentally separated by a galactokinase coding sequence (Lüscher, B. et al., (1985). Proc. Natl. Acad. Sci. USA, 82(13), 4389-4393).

Additionally, Stauber et al. identified the minimal sequence required to confer cell-cycle regulation on histone H4 mRNA levels. For these investigations constructs were used, comprising a coding sequence for the selection marker Xanthine:guanine phosphoribosyl transferase (GPT) preceding a histone stem-loop signal followed by a polyadenylation signal (Stauber, C. et al., (1986). EMBO J, 5(12), 3297-3303).

Examining histone pre-mRNA processing Wagner et al. identified factors required for cleavage of histone pre-mRNAs using a reporter construct placing EGFP between a histone stem-loop signal and a polyadenylation signal, such that EGFP was expressed only in case histone pre-mRNA processing was disrupted (Wagner, E. J. et al., (2007). Mol Cell 28(4), 692-9).

To be noted, translation of polyadenylated mRNA usually requires the 3' poly(A) sequence to be brought into proximity of the 5' CAP. This is mediated through protein-protein interaction between the poly(A) binding protein and eukaryotic initiation factor eIF4G. With respect to replication-dependent histone mRNAs, an analogous mechanism has been uncovered. In this context, Gallie et al. show that the histone stem-loop is functionally similar to a poly(A) sequence in that it enhances translational efficiency and is co-dependent on a 5'-CAP in order to establish an efficient level of translation. They showed that the histone stem-loop is sufficient and necessary to increase the translation of a reporter mRNA in transfected Chinese hamster ovary cells but must be positioned at the 3'-terminus in order to function optimally. Therefore, similar to the poly(A) tail on other mRNAs, the 3' end of these histone mRNAs appears to be essential for translation in vivo and is functionally analogous to a poly(A) tail (Gallie, D. R., Lewis, N. J., & Marzluff, W. F. (1996), Nucleic Acids Research, 24(10), 1954-1962).

Additionally, it could be shown that SLBP is bound to the cytoplasmic histone mRNA and is required for its translation. Even though SLBP does not interact directly with eIF4G, the domain required for translation of histone mRNA interacts with the recently identified protein SLIP1. In a further step, SLIP1 interacts with eIF4G and allows to circularize histone mRNA and to support efficient translation of histone mRNA by a mechanism similar to the translation of polyadenylated mRNAs.

As mentioned above, gene therapy approaches normally use DNA to transfer the coding information into the cell which is then transcribed into mRNA, carrying the naturally occurring elements of an mRNA, particularly the 5'-CAP structure and the 3' poly(A) sequence to ensure expression of the encoded therapeutic protein.

However, in many cases expression systems based on the introduction of such nucleic acids into the patient's cells or tissue and the subsequent expression of the desired polypeptides coded for by these nucleic acids do not exhibit the desired, or even the required, level of expression which may allow for an efficient therapy, irrespective as to whether DNA or RNA is used.

In the prior art, different attempts have hitherto been made to increase the yield of the expression of an encoded protein, in particular by use of improved expression systems, both in vitro and/or in vivo. Methods for increasing expression described generally in the prior art are conventionally based on the use of expression vectors or cassettes containing specific promoters and corresponding regulation elements. As these expression vectors or cassettes are typically limited to particular cell systems, these expression systems have to be adapted for use in different cell systems. Such adapted expression vectors or cassettes are then usually transfected into the cells and typically treated in dependence of the specific cell line. Therefore, preference is given primarily to those nucleic acid molecules which are able to express the encoded proteins in a target cell by systems inherent in the cell, independent of promoters and regulation elements which are specific for particular cell types. In this context, there can be distinguished between mRNA stabilizing elements and elements which increase translation efficiency of the mRNA.

mRNAs which are optimized in their coding sequence and which are in general suitable for such a purpose are described in application WO 02/098443 (CureVac GmbH). For example, WO 02/098443 describes mRNAs that are stabilised in general form and optimised for translation in their coding regions. WO 02/098443 further discloses a method for determining sequence modifications. WO 02/098443 additionally describes possibilities for substituting adenine and uracil nucleotides in mRNA sequences in order to increase the guanine/cytosine (G/C) content of the sequences. According to WO 02/098443, such substitutions and adaptations for increasing the G/C content can be used for gene therapeutic applications but also genetic vaccines in the treatment of cancer or infectious diseases. In this context, WO 02/098443 generally mentions sequences as a base sequence for such modifications, in which the modified mRNA codes for at least one biologically active peptide or polypeptide, which is translated in the patient to be treated, for example, either not at all or inadequately or with faults. Alternatively, WO 02/098443 proposes mRNAs coding for antigens e.g. tumour antigens or viral antigens as a base sequence for such modifications.

In a further approach to increase the expression of an encoded protein the application WO 2007/036366 describes the positive effect of long poly(A) sequences (particularly longer than 120 bp) and the combination of at least two 3' untranslated regions of the beta globin gene on mRNA stability and translational activity.

However, even though all these latter prior art documents already try to provide quite efficient tools for gene therapy approaches and additionally improved mRNA stability and translational activity, there still remains the problem of a generally lower stability of RNA-based applications versus DNA vaccines and DNA based gene therapeutic approaches. Accordingly, there still exists a need in the art to provide improved tools for gene therapy approaches and genetic vaccination or as a supplementary therapy for conventional treatments as discussed above, which allow for better provision of encoded proteins in vivo, e.g. via a further improved mRNA stability and/or translational activity, preferably for gene therapy.

The object underlying the present invention is, therefore, to provide additional and/or alternative methods to increase expression of an encoded protein, preferably via further stabilization of the mRNA and/or an increase of the translational efficiency of such an mRNA with respect to such nucleic acids known from the prior art for the use in therapeutic applications (e.g. gene therapy and genetic vaccination).

This object is solved by the subject matter of the attached claims. Particularly, the object underlying the present invention is solved according to a first embodiment by an inventive nucleic acid sequence comprising or coding for a) a coding region, preferably encoding a peptide or protein;
b) at least one histone stem-loop, and
c) optionally a poly(A) sequence or a polyadenylation signal, preferably for increasing the expression level of an encoded protein, wherein the encoded protein is preferably no histone protein, no reporter protein (e.g. Luciferase, GFP, EGFP, β-Galactosidase, particularly EGFP) and no marker or selection protein (e.g. alpha-Globin, Galactokinase and Xanthine:guanine phosphoribosyl transferase (GPT)).

In this context it is particularly preferred that the inventive nucleic acid according to the first embodiment of the present invention is produced at least partially by DNA or RNA synthesis or is an isolated nucleic acid.

The present invention is based on the surprising finding of the present inventors, that the combination of a poly(A) sequence or polyadenylation signal and at least one histone stem-loop, even though both representing alternative mechanisms in nature, acts synergistically as this combination increases the protein expression manifold above the level observed with either of the individual elements. The synergistic effect of the combination of poly(A) and at least one histone stem-loop is seen irrespective of the order of poly(A) and histone stem-loop and irrespective of the length of the poly(A) sequence.

Therefore it is particularly preferred that the inventive nucleic acid molecule comprises or codes for a) a coding region, preferably encoding a peptide or protein; b) at least one histone stem-loop, and c) a poly(A) sequence or polyadenylation sequence; preferably for increasing the expression level of an encoded protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

In a further alternative aspect of the first embodiment of the present invention the inventive nucleic acid comprises no histone downstream element (HDE).

In this context it is particularly preferred that the inventive nucleic acid comprises or codes for in 5'- to 3'-direction:

a) a coding region, preferably encoding a peptide or protein;
b) at least one histone stem-loop, optionally without a histone downstream element 3' to the histone stem-loop
c) a poly(A) sequence or a polyadenylation signal.

The term "histone downstream element (HDE) refers to a purine-rich polynucleotide stretch of about 15 to 20 nucleotides 3' of naturally occurring stem-loops, which represents the binding site for the U7 snRNA involved in processing of histone pre-mRNA into mature histone mRNA. For example in sea urchins the HDE is CAAGAAAGA (Dominski, Z. and W. F. Marzluff (2007), Gene 396(2): 373-90).

Furthermore it is preferable that the inventive nucleic acid according to the first embodiment of the present invention does not comprise an intron.

In another particular preferred embodiment, the inventive nucleic acid sequence according to the first embodiment of the present invention comprises or codes for from 5' to 3':

a) a coding region, preferably encoding a peptide or protein;

c) a poly(A) sequence; and b) at least one histone stem-loop.

The inventive nucleic acid sequence according to the first embodiment of the present invention comprise any suitable nucleic acid, selected e.g. from any (single-stranded or double-stranded) DNA, preferably, without being limited thereto, e.g. genomic DNA, single-stranded DNA molecules, double-stranded DNA molecules, or may be selected e.g. from any PNA (peptide nucleic acid) or may be selected e.g. from any (single-stranded or double-stranded) RNA, preferably a messenger RNA (mRNA); etc. The inventive nucleic acid molecule may also comprise a viral RNA (vRNA). However, the inventive nucleic acid sequence may not be a viral RNA or may not contain a viral RNA. More specifically, the inventive nucleic acid sequence may not contain viral sequence elements, e.g. viral enhancers or viral promotors (e.g. no inactivated viral promoter or sequence elements, more specifically not inactivated by replacement strategies), or other viral sequence elements, or viral or retroviral nucleic acid sequences. More specifically, the inventive nucleic acid sequence may not be a retroviral or viral vector or a modified retroviral or viral vector.

In any case, the inventive nucleic acid sequence may or may not contain a enhancer and/or promoter sequence, which may be modified or not or which may be activated or not. The enhancer and or promoter may be plant expressible or not expressible, and/or in eucaryotes expressible or not expressible and/or in prokaryotes expressible or not expressible. The inventive nucleic acid molecule may contain a sequence encoding a (self-splicing) ribozyme or not.

Preferably, the inventive nucleic acid molecule is an RNA.

In particular aspects of the first embodiment of the present invention, the inventive nucleic acid is a nucleic acid sequence comprised in a nucleic acid suitable for in vitro transcription, particularly in an appropriate in vitro transcription vector (e.g. a plasmid or a linear nucleic acid sequence comprising specific promoters for in vitro transcription such as T3, T7 or Sp6 promoters).

In further particular preferred aspects of the first embodiment of the present invention, the inventive nucleic acid is comprised in a nucleic acid suitable for transcription and/or translation in an expression system (e.g. in an expression vector or plasmid), particularly a prokaryotic (e.g. bacteria like *E. coli*) or eukaryotic (e.g. mammalian cells like CHO cells, yeast cells or insect cells or whole organisms like plants or animals) expression system.

The term "expression system" means a system (cell culture or whole organisms) which is suitable for production of peptides, proteins or RNA particularly mRNA.

The inventive nucleic acid sequence according to the first embodiment of the present invention comprises or codes for at least one histone stem-loop. In the context of the present invention, such a histone stem-loop is typically derived from histone genes and comprises an intramolecular base pairing of two neighbored entirely or partially reverse complementary sequences, thereby forming a stem-loop. A stem-loop can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem loop elements stem1 and stem2. The stem loop is formed when these two neighbored entirely or partially reverse complementary sequences, e.g. stem loop elements stem1 and stem2, form base-pairs with each other, leading to a double stranded nucleic acid sequence comprising an unpaired loop at its terminal ending formed by the short sequence located between stem loop elements stem1 and stem2 on the consecutive sequence. The unpaired loop thereby typically represents a region of the nucleic acid which is not capable of base pairing with either of these stem loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem loop elements is determined by the length, the number of mismatches or bulges it contains (a small number of mismatches is typically tolerable, especially in a long double strand), and the base composition of the paired region. In the context of the present invention, optimal loop length is 3-10 bases, more preferably 3 to 8, 3 to 7, 3 to 6 or even more preferably 4 to 5 bases, and most preferably 4 bases.

According to the present invention the histon stem loop sequence according to component (b) of claim 1 may not derived from a mouse histon protein. More specifically, the histon stem loop sequence may not be derived from mouse histon gene H2A614. Also, the nucleic acid of the invention may neither contain a mouse histon stem loop sequence nor contain mouse histon gene H2A614. Further, the inventive nucleic acid sequence may not contain a stem-loop processing signal, more specifically, a mouse histon processing signal and, most specifically, may not contain mouse stem loop processing signal H2kA614. Also, if the inventive nucleic acid molecule may contain at least one mammalian histon gene. However, the at least one mammalian histon gene may not be Seq. ID No. 7 of WO 01/12824.

According to one preferred aspect of the first inventive embodiment, the inventive nucleic acid sequence comprises or codes for at least one histone stem-loop sequence, preferably according to at least one of the following formulae (I) or (II):

formula (I) (stem-loop sequence without stem bordering elements):

$$\underbrace{[N_{0-2}GN_{3-5}]}_{\text{stem1}}\ \underbrace{[N_{0-4}(U/T)N_{0-4}]}_{\text{loop}}\ \underbrace{[N_{3-5}CN_{0-2}]}_{\text{stem2}}$$

formula (II) (stem-loop sequence with stem bordering elements):

$$\underbrace{N_{1-6}}_{\text{stem1 bordering element}}\ \underbrace{[N_{0-2}GN_{3-5}]}_{\text{stem1}}\ \underbrace{[N_{0-4}(U/T)N_{0-4}]}_{\text{loop}}\ \underbrace{[N_{3-5}CN_{0-2}]}_{\text{stem2}}\ \underbrace{N_{1-6}}_{\text{stem2 bordering element}}$$

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;

wherein $N_{0-2}$, is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$, is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleotide guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

In the above context, a wobble base pairing is typically a non-Watson-Crick base pairing between two nucleotides. The four main wobble base pairs in the present context, which may be used, are guanosine-uridine, inosine-uridine, inosine-adenosine, inosine-cytidine (G-U/T, I-U/T, I-A and I-C) and adenosine-cytidine (A-C).

Accordingly, in the context of the present invention, a wobble base is a base, which forms a wobble base pair with a further base as described above. Therefore non-Watson-Crick base pairing, e.g. wobble base pairing, may occur in the stem of the histone stem-loop structure according to the present invention.

In the above context a partially reverse complementary sequence comprises maximally 2, preferably only one mismatch in the stem-structure of the stem-loop sequence formed by base pairing of stem1 and stem2. In other words, stem1 and stem2 are preferably capable of (full) base pairing with each other throughout the entire sequence of stem1 and stem2 (100% of possible correct Watson-Crick or non-Watson-Crick base pairings), thereby forming a reverse complementary sequence, wherein each base has its correct Watson-Crick or non-Watson-Crick base pendant as a complementary binding partner. Alternatively, stem1 and stem2 are preferably capable of partial base pairing with each other throughout the entire sequence of stem1 and stem2, wherein at least about 70%, 75%, 80%, 85%, 90%, or 95% of the 100% possible correct Watson-Crick or non-Watson-Crick base pairings are occupied with the correct Watson-Crick or non-Watson-Crick base pairings and at most about 30%, 25%, 20%, 15%, 10%, or 5% of the remaining bases are unpaired.

According to a preferred aspect of the first inventive embodiment, the at least one histone stem-loop sequence (with stem bordering elements) of the inventive nucleic acid sequence as defined herein comprises a length of about 15 to about 45 nucleotides, preferably a length of about 15 to about 40 nucleotides, preferably a length of about 15 to about 35 nucleotides, preferably a length of about 15 to about 30 nucleotides and even more preferably a length of about 20 to about 30 and most preferably a length of about 24 to about 28 nucleotides.

According to a further preferred aspect of the first inventive embodiment, the at least one histone stem-loop sequence (without stem bordering elements) of the inventive nucleic acid sequence as defined herein comprises a length of about 10 to about 30 nucleotides, preferably a length of about 10 to about 20 nucleotides, preferably a length of about 12 to about 20 nucleotides, preferably a length of about 14 to about 20 nucleotides and even more preferably a length of about 16 to about 17 and most preferably a length of about 16 nucleotides.

According to a further preferred aspect of the first inventive embodiment, the inventive nucleic acid sequence according to the first embodiment of the present invention may comprise or code for at least one histone stem-loop sequence according to at least one of the following specific formula (Ia) or (IIa):

formula (Ia) (stem-loop sequence without stem bordering elements):

$$\underbrace{[N_{0-1}GN_{3-5}]}_{\text{stem1}}\ \underbrace{[N_{1-3}(U/T)N_{0-2}]}_{\text{loop}}\ \underbrace{[N_{3-5}CN_{0-1}]}_{\text{stem2}}$$

formula (IIa) (stem-loop sequence with stem bordering elements):

$$\underbrace{N_{2-5}}_{\substack{\text{stem1}\\\text{bordering element}}}\ \underbrace{[N_{0-1}GN_{3-5}]}_{\text{stem1}}\ \underbrace{[N_{1-3}(U/T)N_{0-2}]}_{\text{loop}}\ \underbrace{[N_{3-5}CN_{0-1}]}_{\text{stem2}}\ \underbrace{N_{2-5}}_{\substack{\text{stem2}\\\text{bordering element}}}$$

wherein:

N, C, G, T and U are as defined above.

According to a further more particularly preferred aspect of the first embodiment, the inventive nucleic acid sequence may comprise or code for at least one histone stem-loop sequence according to at least one of the following specific formulae (Ib) or (IIb):

formula (Ib) (stem-loop sequence without stem bordering elements):

$$\underbrace{[N_1GN_4]}_{\text{stem1}}\ \underbrace{[N_2(U/T)N_1]}_{\text{loop}}\ \underbrace{[N_4CN_1]}_{\text{stem2}}$$

formula (IIb) (stem-loop sequence with stem bordering elements):

$$\underbrace{N_{4-5}}_{\substack{\text{stem1}\\\text{bordering element}}}\ \underbrace{[N_1GN_4]}_{\text{stem1}}\ \underbrace{[N_2(U/T)N_1]}_{\text{loop}}\ \underbrace{[N_4CN_1]}_{\text{stem2}}\ \underbrace{N_{4-5}}_{\substack{\text{stem2}\\\text{bordering element}}}$$

wherein:

N, C, G, T and U are as defined above.

According to an even more preferred aspect of the first inventive embodiment, the inventive nucleic acid sequence according to the first embodiment of the present invention may comprise or code for at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1:

formula (Ic): (metazoan and protozoan histone stem-loop consensus sequence without stem bordering elements):

```
 N U
N   N
 N-N
 N-N
 N-N
 N-N
 G-C
```

-continued

```
 N-N
(stem-loop structure)
```

(SEQ ID NO: 1)

```
NGNNNNNNUNNNNNCN
(linear sequence)
```

formula (IIc): (metazoan and protozoan histone stem-loop consensus sequence with stem bordering elements):

```
     N U
    N   N
     N-N
     N-N
     N-N
     N-N
     G-C
N*N*NNNN-NNNN*N*N*
(stem looping structure)
```

(SEQ ID NO: 2)

```
N*N*NNNNGNNNNNNUNNNNNCNNNN*N*N*
(linear sequence)
```

formula (Id): (without stem bordering elements)

```
 N U
N   N
 N-N
 N-N
 N-N
 N-N
 C-G
 N-N (stem-loop structure)
```

(SEQ ID NO: 3)

```
NCNNNNNNUNNNNNGN
(linear sequence)
```

formula (IId): (with stem bordering elements)

```
 N U
N   N
 N-N
 N-N
 N-N
 N-N
 C-G
N*N*NNNN-NNNN*N*N* (stem-loop structure)
```

(SEQ ID NO: 4)

```
N*N*NNNNCNNNNNNUNNNNNGNNNN*N*N*
(linear sequence)
```

formula (Ie): (protozoan histone stem-loop consensus sequence without stem bordering elements)

```
 N U
N   N
 N-N
 N-N
 N-N
 N-N
 G-C
 D-H (stem-loop structure)
```

(SEQ ID NO: 5)
DGNNNNNNUNNNNNCH
(linear sequence)

formula (IIe): (protozoan histone stem-loop consensus sequence with stem bordering elements)

```
 N U
N   N
 N-N
 N-N
 N-N
 N-N
 G-C
N*N*NNND-HNNN*N*N* (stem-loop structure)
```

(SEQ ID NO: 6)
N*N*NNNDGNNNNNNUNNNNNCHNNN*N*N*
(linear sequence)

formula (If): (metazoan histone stem-loop consensus sequence without stem bordering elements)

```
 N U
N   N
 Y-V
 Y-N
 B-D
 N-N
 G-C
 N-N (stem-loop structure)
```

(SEQ ID NO: 7)
NGNBYYNNUNVNDNCN
(linear sequence)

formula (IIf): (metazoan histone stem-loop consensus sequence with stem bordering elements)

-continued

```
 N U
N   N
 Y-V
 Y-N
 B-D
 N-N
 G-C
N*N*NNNN-NNNN*N*N* (stem-loop structure)
```

(SEQ ID NO: 8)
N*N*NNNNGNBYYNNUNVNDNCNNNN*N*N*
(linear sequence)

formula (Ig): (vertebrate histone stem-loop consensus sequence without stem bordering elements)

```
 N U
D   H
 Y-A
 Y-B
 Y-R
 H-D
 G-C
 N-N (stem-loop structure)
```

(SEQ ID NO: 9)
NGHYYYDNUHABRDCN
(linear sequence)

formula (IIg): (vertebrate histone stem-loop consensus sequence with stem bordering elements)

```
 N U
D   H
 Y-A
 Y-B
 Y-R
 H-D
 G-C
N*N*HNNN-NNNN*N*H* (stem-loop structure)
```

(SEQ ID NO: 10)
N*N*HNNNGHYYYDNUHABRDCNNNN*N*H*
(linear sequence)

formula (Ih): (human histone stem-loop consensus sequence (*Homo sapiens*) without stem bordering elements)

```
 Y U
D   H
 U-A
 C-S
 Y-R
```

```
                H-R

                G-C

                D-C     (stem-loop structure)

                                        (SEQ ID NO: 11)
           DGHYCUDYUHASRRCC
           (linear sequence)
```

formula (IIh): (human histone stem-loop consensus sequence (*Homo sapiens*) with stem bordering elements)

```
           Y     U

           D     H

           U  -  A

           C  -  S

           Y  -  R

           H  -  R

           G  -  C

      N*H*AAHD-CVHB*N*H*  (stem loop structure)

                                        (SEQ ID NO: 12)
      N*H*AAHDGHYCUDYUHASRRCCVHB*N*H*
      (linear sequence)
```

wherein in each of above formulae (Ic) to (Ih) or (IIc) to (IIh):

N, C, G, A, T and U are as defined above;
each U may be replaced by T;
each (highly) conserved G or C in the stem elements 1 and 2 may be replaced by its complementary nucleotide base C or G, provided that its complementary nucleotide in the corresponding stem is replaced by its complementary nucleotide in parallel; and/or G, A, T, U, C, R, Y, M, K, S, W, H, B, V, D, and N are nucleotide bases as defined in the following Table:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context it is particularly preferred that the histone stem-loop sequence according to at least one of the formulae (I) or (Ia) to (Ih) or (II) or (IIa) to (IIh) of the present invention is selected from a naturally occurring histone stem loop sequence, more particularly preferred from protozoan or metazoan histone stem-loop sequences, and even more particularly preferred from vertebrate and mostly preferred from mammalian histone stem-loop sequences especially from human histone stem-loop sequences.

According to a particularly preferred aspect of the first embodiment, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa (FIG. 1), protozoa (FIG. 2), metazoa (FIG. 3), vertebrates (FIG. 4) and humans (FIG. 5) as shown in FIG. 1-5. In this context it is particularly preferred that at least 80%, preferably at least 85%, or most preferably at least 90% of all nucleotides correspond to the most frequently occurring nucleotide of naturally occurring histone stem-loop sequences.

In a further particular aspect of the first embodiment, the histone stem-loop sequence according to at least one of the specific formulae (I) or (Ia) to (Ih) of the present invention is selected from following histone stem-loop sequences (without stem-bordering elements) representing histone stem-loop sequences as generated according to Example 1:

```
VGYYYYHHTHRVVRCB
(SEQ ID NO: 13 according to formula (Ic))

SGYYYTTYTMARRRCS
(SEQ ID NO: 14 according to formula (Ic))

SGYYCTTTTMAGRRCS
(SEQ ID NO: 15 according to formula (Ic))

DGNNNBNNTHVNNNCH
(SEQ ID NO: 16 according to formula (Ie))

RGNNNYHBTHRDNNCY
(SEQ ID NO: 17 according to formula (Ie))

RGNDBYHYTHRDHNCY
(SEQ ID NO: 18 according to formula (Ie))

VGYYYTYHTHRVRRCB
(SEQ ID NO: 19 according to formula (If)

SGYYCTTYTMAGRRCS
(SEQ ID NO: 20 according to formula (If))

SGYYCTTTTMAGRRCS
(SEQ ID NO: 21 according to formula (If))

GGYYCTTYTHAGRRCC
(SEQ ID NO: 22 according to formula (Ig))

GGCYCTTYTMAGRGCC
(SEQ ID NO: 23 according to formula (Ig))

GGCTCTTTTMAGRGCC
(SEQ ID NO: 24 according to formula (Ig))

DGHYCTDYTHASRRCC
(SEQ ID NO: 25 according to formula (Ih))

GGCYCTTTTHAGRGCC
(SEQ ID NO: 26 according to formula (Ih))

GGCYCTTTTMAGRGCC
(SEQ ID NO: 27 according to formula (Ih))
```

Furthermore in this context following histone stem-loop sequences (with stem bordering elements) as generated according to Example 1 according to one of specific formulae (II) or (IIa) to (IIh) are particularly preferred:

H*H*HHVVGYYYYHHTHRVVRCBVHH*N*N*
(SEQ ID NO: 28 according to formula (IIc))

M*H*MHMSGYYYTTYTMARRRCSMCH*H*H*
(SEQ ID NO: 29 according to formula (IIc))

M*M*MMMSGYYCTTTTMAGRRCSACH*M*H*
(SEQ ID NO: 30 according to formula (IIc))

N*N*NNNDGNNNBNNTHVNNNCHNHN*N*N*
(SEQ ID NO: 31 according to formula (IIe))

N*N*HHNRGNNNYHBTHRDNNCYDHH*N*N*
(SEQ ID NO: 32 according to formula (IIe))

N*H*HHVRGNDBYHYTHRDHNCYRHH*H*H*
(SEQ ID NO: 33 according to formula (IIe))

H*H*MHMVGYYYTYHTHRVRRCBVMH*H*N*
(SEQ ID NO: 34 according to formula (IIf)

M*M*MMMSGYYCTTYTMAGRRCSMCH*H*H*
(SEQ ID NO: 35 according to formula (IIf)

M*M*MMMSGYYCTTTTMAGRRCSACH*M*H*
(SEQ ID NO: 36 according to formula (IIf)

H*H*MAMGGYYCTTYTHAGRRCCVHN*N*M*
(SEQ ID NO: 37 according to formula (IIg))

H*H*AAMGGCYCTTYTMAGRGCCVCH*H*M*
(SEQ ID NO: 38 according to formula (IIg))

M*M*AAMGGCTCTTTTMAGRGCCMCY*M*M*
(SEQ ID NO: 39 according to formula (IIg))

N*H*AAHDGHYCTDYTHASRRCCVHB*N*H*
(SEQ ID NO: 40 according to formula (IIh))

H*H*AAMGGCYCTTTTHAGRGCCVMY*N*M*
(SEQ ID NO: 41 according to formula (IIh))

H*M*AAAGGCYCTTTTMAGRGCCRMY*H*M*
(SEQ ID NO: 42 according to formula (IIh))

According to a further preferred aspect of the first inventive embodiment, the inventive nucleic acid sequence comprises or codes for at least one histone stem-loop sequence showing at least about 80%, preferably at least about 85%, more preferably at least about 90%, or even more preferably at least about 95%, sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

The inventive nucleic acid sequence according to the first embodiment of the present invention may optionally comprise or code for a poly(A) sequence. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to.

Preferably, the nucleic acid according of the present invention does not contain one or two or at least one or all but one or all of the components of the group consisting of: a sequence encoding a ribozyme (preferably a self-splicing ribozyme), a viral nucleic acid sequence, a histone stem-loop processing signal, in particular a histon-stem loop processing sequence derived from mouse histon H2A614 gene, a Neo gene, an inactivated promoter sequence and an inactivated enhancer sequence. Even more preferably, the nucleic acid according to the invention does not contain a ribozyme, preferably a self-splicing ribozyme, and one of the group consisting of: a Neo gene, an inactivated promotor sequence, an inactivated enhancer sequence, a histon stem-loop processing signal, in particular a histon-stem loop processing sequence derived from mouse histon H2A614 gene. Accordingly, the nucleic acid may in a preferred mode neither contain a ribozyme, preferably a self-splicing ribozyme, nor a Neo gene or, alternatively, neither a ribozyme, preferably a self-splicing ribozyme, nor any resistance gene (e.g. usually applied for selection). In an other preferred mode, the nucleic acid of the invention may neither contain a a ribozyme, preferably a self-splicing ribozyme nor a histon stem-loop processing signal, in particular a histon-stem loop processing sequence derived from mouse histon H2A614 gene Alternatively, according to the first embodiment of the present invention, the inventive nucleic sequence optionally comprises a polyadenylation signal which is defined herein as a signal which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context a consensus polyadenylation signal is preferred comprising the NNUANA consensus sequence. In a particular preferred aspect the polyadenylation signal comprises one of the following sequences: AAUAAA or AUUAAA.

The inventive nucleic acid sequence according to the first embodiment of the present invention furthermore encode a protein or a peptide, which may be selected, without being restricted thereto, e.g. from therapeutically active proteins or peptides, including adjuvant proteins, from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the inventive nucleic acid may be transported into a cell (e.g. an expression host cell or a somatic cell), a tissue or an organism and the protein may be expressed subsequently in this cell, tissue or organism.

The coding region of the inventive nucleic acid according to the first embodiment of the present invention may occur as a mono-, di-, or even multicistronic nucleic acid, i.e. a nucleic acid which carries the coding sequences of one, two or more proteins or peptides. Such coding sequences in di-, or even multicistronic nucleic acids may be separated by at least one internal ribosome entry site (IRES) sequence, e.g. as defined herein or by signal peptides which induce the cleavage of the resulting polypeptide which comprises several proteins or peptides.

In particular preferred aspects of the first embodiment of the present invention the encoded peptides or proteins are selected from human, viral, bacterial, protozoan proteins or peptides.

In the context of the present invention, therapeutically active proteins, encoded by the inventive nucleic acid molecule may be selected, without being restricted thereto, from proteins which have an effect on healing, prevent prophylactically or treat therapeutically a disease, preferably as defined herein, or are proteins of which an individual is in need of. Such proteins may be selected from any naturally or synthetically designed occurring recombinant or isolated protein known to a skilled person from the prior art. Without being restricted thereto therapeutically active proteins may comprise proteins, capable of stimulating or inhibiting the signal transduction in the cell, e.g. cytokines, lymphokines, monokines, growth factors, receptors, signal transduction molecules, transcription factors, etc; anticoagulants; antithrombins; antiallergic proteins; apoptotic factors or apoptosis related proteins, therapeutic active enzymes and any protein connected with any acquired disease or any hereditary disease.

Preferably, a therapeutically active protein, which may be encoded by the inventive nucleic acid molecule, may also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. More preferably, the adjuvant protein is selected from human adjuvant proteins or from pathogenic adjuvant proteins, selected from the group consisting of, without being limited thereto, bacterial proteins, protozoan proteins, viral proteins, or fungal proteins, animal proteins, in particular from bacterial adjuvant proteins. In addition, nucleic acids encoding human proteins involved in adjuvant effects (e.g. ligands of pattern recognition receptors, pattern recognition receptors, proteins of the signal transduction pathways, transcription factors or cytokines) may be used as well.

The inventive nucleic acid molecule may alternatively encode an antigen. According to the present invention, the term “antigen” refers to a substance which is recognized by the immune system and is capable of triggering an antigen-specific immune response, e.g. by formation of antibodies or antigen-specific T-cells as part of an adaptive immune response.

In this context an antigenic epitope, fragment or peptide of a protein means particularly B cell and T cell epitopes which may be recognized by B cells, antibodies or T cells respectively.

In the context of the present invention, antigens, which may be encoded by the inventive nucleic acid molecule, typically comprise any antigen, antigenic epitope, antigenic fragment or antigenic peptide, falling under the above definition, more preferably protein and peptide antigens, e.g. tumour antigens, allergenic antigens or allergens, auto-immune self-antigens, pathogenic antigens, etc.

In particular antigens as encoded by the inventive nucleic acid molecule may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens or allergens) are typically antigens, which cause an allergy in a human and may be derived from either a human or other sources. Additionally, antigens as encoded by the inventive nucleic acid molecule may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc.

One class of antigens, which may be encoded by the inventive nucleic acid molecule comprises tumour antigens. “Tumour antigens” are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as “tumour antigens”, however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal “healthy” cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies.

According to another alternative, one further class of antigens, which may be encoded by the inventive nucleic acid molecule, comprises allergenic antigens. Such allergenic antigens may be selected from antigens derived from different sources, e.g. from animals, plants, fungi, bacteria, etc. Allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are antigens, which may be encoded by the inventive nucleic acid molecule as defined herein, i.e. protein or peptide antigens and their fragments or epitopes, or nucleic acids and their fragments, particularly nucleic acids and their fragments, encoding such protein or peptide antigens and their fragments or epitopes.

According to a further alternative, the inventive nucleic acid molecule may encode an antibody or an antibody fragment. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term “antibody” is used in its broadest sense and specifically covers monoclonal and polyclonal antibodies (including agonist, antagonist, and blocking or neutralizing antibodies) and antibody species with polyepitopic specificity. According to the invention, the term “antibody” typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$.

In the context of the present invention, antibodies as encoded by the inventive nucleic acid molecule may preferably comprise full-length antibodies, i.e. antibodies composed of the full heavy and full light chains, as described above. However, derivatives of antibodies such as antibody fragments, variants or adducts may also be encoded by the inventive nucleic acid molecule. Antibody fragments are preferably selected from Fab, Fab', $F(ab')_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In the present context it is preferable that the different chains of the antibody or antibody fragment are encoded by a multicistronic nucleic acid molecule. Alternatively, the different strains of the antibody or antibody fragment are encoded by several monocistronic nucleic acid(s) (sequences).

According to the first embodiment of the present invention, the inventive nucleic acid sequence comprises a coding region, preferably encoding a peptide or protein. Preferably, the encoded protein is no histone protein. In the context of the present invention such a histone protein is typically a strongly alkaline protein found in eukaryotic cell nuclei, which package and order the DNA into structural units called nucleosomes. Histone proteins are the chief protein components of chromatin, act as spools around which DNA winds, and play a role in gene regulation. Without histones, the unwound DNA in chromosomes would be very long (a length to width ratio of more than 10 million to one in human DNA). For example, each human cell has about 1.8 meters of DNA, but wound on the histones it has about 90 millimeters of chromatin, which, when duplicated and condensed during mitosis, result in about 120 micrometers of chromosomes. More preferably, in the context of the present invention such a histone protein is typically defined as a highly conserved protein selected from one of the following five major classes of histones: H1/H5, H2A, H2B, H3, and H4", preferably selected from mammalian histone, more preferably from human histones or histone proteins. Such histones or histone proteins are typically organised into two super-classes defined as core histones, comprising histones H2A, H2B, H3 and H4, and linker histones, comprising histones H1 and H5.

In this context, linker histones, preferably excluded from the scope of protection of the pending invention, preferably mammalian linker histones, more preferably human linker histones, are typically selected from H1, including H1F, particularly including H1F0, H1FNT, H1FOO, H1FX, and H1H1, particularly including HIST1H1A, HIST1H1B, HIST1H1C, HIST1H1D, HIST1H1E, HIST1H1T; and Furthermore, core histones, preferably excluded from the scope of protection of the pending invention, preferably mammalian core histones, more preferably human core histones, are typically selected from H2A, including H2AF, particularly including H2AFB1, H2AFB2, H2AFB3, H2AFJ, H2AFV, H2AFX, H2AFY, H2AFY2, H2AFZ, and H2A1, particularly including HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, and H2A2, particularly including HIST2H2AA3, HIST2H2AC; H2B, including H2BF, particularly including H2BFM, H2BFO, H2BFS, H2BFWT H2B1, particularly including HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, and H2B2, particularly including HIST2H2BE; H3, including H3A1, particularly including HIST1H3A, HIST1H3B, HIST1H3C, HIST1H3D, HIST1H3E, HIST1H3F, HIST1H3G, HIST1H3H, HIST1H3I, HIST1H3J, and H3A2, particularly including HIST2H3C, and H3A3, particularly including HIST3H3; H4, including H41, particularly including HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, and H44, particularly including HIST4H4, and H5.

According to the first embodiment of the present invention, the inventive nucleic acid sequence comprises a coding region, preferably encoding a peptide or protein. Preferably, the encoded protein is no reporter protein (e.g. Luciferase, Green Fluorescent Protein (GFP), Enhanced Green Fluorescent Protein (EGFP), (β-Galactosidase) and no marker or selection protein (e.g. alpha-Globin, Galactokinase and Xanthine:guanine phosphoribosyl transferase (GPT)). Preferably, the nucleic acid sequence of the invention does not contain a (bacterial) Neo gene sequence (Neomycin resistance gene).

The inventive nucleic acid as define above, comprises or codes for a) a coding region, preferably encoding a peptide or protein; b) at least one histone stem-loop, and c) optionally a poly(A) sequence or polyadenylation signal; preferably for increasing the expression level of an encoded protein, wherein the encoded protein is preferably no histone protein, no reporter protein and/or no marker or selection protein, as defined above. The elements b) to c) of the inventive nucleic acid may occur in the inventive nucleic acid in any order, i.e. the elements a), b) and c) may occur in the order a), b) and c) or a), c) and b) from 5' to 3' direction in the inventive nucleic acid sequence, wherein further elements as described herein, may also be contained, such as a 5'-CAP structure, a poly(C) sequence, stabilization sequences, IRES sequences, etc. Each of the elements a) to c) of the inventive nucleic acid, particularly a) in di- or multicistronic constructs and/or each of the elements b) and c), more preferably element b) may also be repeated at least once, preferably twice or more in the inventive nucleic acid.

As an example, the inventive nucleic acid may show its sequence elements a), b) and optionally c) in e.g. the following order:

5'—coding region—histone stem-loop—3'; or

5'—coding region—coding region—histone stem-loop—3'; or

5'—coding region—IRES—coding region—histone stem-loop—3'; or

5'—coding region—histone stem-loop—poly(A) sequence—3'; or

5'—coding region—histone stem-loop—polyadenylation signal—3'; or

5'—coding region—coding region—histone stem-loop—polyadenylation signal—3'; or

5'—coding region—histone stem-loop—histone stem-loop—3'; or

5'—coding region—histone stem-loop—histone stem-loop—poly(A) sequence—3'; or

5'—coding region—histone stem-loop—histone stem-loop—polyadenylation signal—3'; or 5'—coding region—histone stem-loop—poly(A) sequence—histone stem-loop—3'; or 5'—coding region—poly(A) sequence—histone stem-loop—3'; or 5'—coding region—poly(A) sequence—histone stem-loop—histone stem-loop—3'; etc.

In this context it is particularly preferred that the inventive nucleic acid molecule comprises or codes for a) a coding region, preferably encoding a peptide or protein; b) at least one histone stem-loop, and c) a poly(A) sequence or polyadenylation sequence; preferably for increasing the expression level of an encoded protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

In a further preferred aspect of the first embodiment the inventive nucleic acid molecule as defined herein may also occur in the form of a modified nucleic acid.

According to one aspect of the first embodiment, the inventive nucleic acid molecule as defined herein may be provided as a "stabilized nucleic acid", preferably as a stabilized RNA, more preferably as a RNA that is essentially resistant to in vivo degradation (e.g. by an exo- or endo-nuclease).

In this context, the inventive nucleic acid molecule as defined herein may contain nucleotide analogues/modifications e.g. backbone modifications, sugar modifications or base modifications. A backbone modification in connection with the present invention is a modification in which phosphates of the backbone of the nucleotides contained in inventive nucleic acid molecule as defined herein are chemically modified. A sugar modification in connection with the present invention is a chemical modification of the sugar of the nucleotides of the inventive nucleic acid molecule as defined herein. Furthermore, a base modification in connection with the present invention is a chemical modification of the base moiety of the nucleotides of the nucleic acid molecule of the inventive nucleic acid molecule. In this context nucleotide analogues or modifications are preferably selected from nucleotide analogues which are applicable for transcription and/or translation.

In a particular preferred aspect of the first embodiment of the present invention the herein defined nucleotide analogues/modifications are selected from base modifications which additionally increase the expression of the encoded protein and which are preferably selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to a further aspect, the inventive nucleic acid molecule as defined herein can contain a lipid modification. Such a lipid-modified nucleic acid typically comprises a nucleic acid as defined herein. Such a lipid-modified nucleic acid molecule of the inventive nucleic acid molecule as defined herein typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule. In this context it is particularly preferred that the lipid modification is present at the terminal ends of a linear inventive nucleic acid sequence.

According to another preferred aspect of the first embodiment of the invention, the inventive nucleic acid molecule as defined herein, particularly if provided as an (m)RNA, can therefore be stabilized against degradation by RNases by the addition of a so-called "5' CAP" structure.

According to a further preferred aspect of the first embodiment of the invention, the inventive nucleic acid molecule as defined herein, can be modified by a sequence of at least 10 cytidines, preferably at least 20 cytidines, more preferably at least 30 cytidines (so-called "poly(C) sequence"). Particularly, the inventive nucleic acid molecule may contain or code for a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. This poly(C) sequence is preferably located 3' of the coding region comprised in the inventive nucleic acid according to the first embodiment of the present invention.

According to another preferred aspect of the first embodiment of the invention, the inventive nucleic acid molecule as defined herein, preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-) globin gene, e.g. from *Homo sapiens* or *Xenopus laevis* may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 55), which is contained in the 3'-UTRs of the very stable RNAs which code for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. In this context it is particularly preferred that the 3' UTR sequence of the alpha globin gene is located 3' of the coding sequence comprised in the inventive nucleic acid according to the first embodiment of the present invention.

Substitutions, additions or eliminations of bases are preferably carried out with the inventive nucleic acid molecule as defined herein, using a DNA matrix for preparation of the nucleic acid molecule by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001). In such a process, for preparation of the inventive nucleic acid molecule as defined herein, especially if the nucleic acid is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Nucleic acid molecules used according to the present invention as defined herein may be prepared using any method known in the art, including synthetic methods such as e.g. solid phase synthesis, as well as in vitro methods, such as in vitro transcription reactions or in vivo reactions, such as in vivo propagation of DNA plasmids in bacteria.

Any of the above modifications may be applied to the inventive nucleic acid molecule as defined herein and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

The inventive nucleic acid molecule as defined herein as well as proteins or peptides as encoded by this nucleic acid molecule may comprise fragments or variants of those sequences. Such fragments or variants may typically comprise a sequence having a sequence identity with one of the above mentioned nucleic acids, or with one of the proteins or peptides or sequences, if encoded by the at least one nucleic acid molecule, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

In a further preferred aspect of the first embodiment of the present invention the inventive nucleic acid sequence is associated with a vehicle, transfection or complexation agent for increasing the transfection efficiency of the inventive nucleic acid sequence. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsI, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl di methyl hydroxyethyl ammonium bromide, DOTAP: dioleoyloxy-3-(trimethylammonio)propane, DC-6-14: O,O,-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

It is preferred that the nucleic acid sequence of the invention is provided in either naked form or complexed, e.g. by polycationic compounds of whatever chemical structure, preferably polycationic (poly)peptides or synthetic polycationic compounds. Preferably, the nucleic acid sequence is not provided together with a packaging cell.

According to a further embodiment, the present invention also provides a method for increasing the expression level of an encoded protein/peptide comprising the steps, e.g. a) providing the inventive nucleic acid as defined herein, b) applying or administering the inventive nucleic acid encoding a protein or peptide as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive nucleic acid as defined herein, it is typically applied or administered to a cell-free expression system, a cell (e.g. an expression host cell or a somatic cell), a tissue or an organism, preferably in naked form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, preferably as defined herein.

In this context in vitro is defined herein as transfection or transduction of the inventive nucleic acid into cells in culture outside of an organism; in vivo is defined herein as transfection or transduction of the inventive nucleic acid into cells by application of the inventive nucleic acid to the whole organism or individual and ex vivo is defined herein as transfection or transduction of the inventive nucleic acid into cells outside of an organism or individual and subsequent application of the transfected cells to the organism or individual.

Likewise, according to another embodiment, the present invention also provides the use of the inventive nucleic acid as defined herein, preferably for diagnostic or therapeutic purposes, for increasing the expression level of an encoded protein/peptide, e.g. by applying or administering the inventive nucleic acid encoding a protein or peptide as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive nucleic acid as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, preferably as defined herein.

In yet another embodiment the present invention also relates to an inventive expression system comprising an inventive nucleic acid or expression vector or plasmid according to the first embodiment of the present invention. In this context the expression system may be a cell-free expression system (e.g. an in vitro transcription/translation system), a cellular expression system (e.g. mammalian cells like CHO cells, insect cells, yeast cells, bacterial cells like *E. coli*) or organisms used for expression of peptides or proteins (e.g. plants or animals like cows).

Additionally, according to another embodiment, the present invention also relates to the use of the inventive nucleic acid as defined herein for the preparation of a pharmaceutical composition for increasing the expression level of an encoded protein/peptide, e.g. for treating a disease as defined herein, e.g. applying or administering the inventive nucleic acid as defined herein to a cell (e.g. an expression host cell or a somatic cell), a tissue or an organism, preferably in naked form or complexed form or as a pharmaceutical composition or vaccine as described herein, more preferably using any of the administration modes as described herein.

Accordingly, in a particular preferred embodiment, the present invention also provides a pharmaceutical composition, comprising the inventive nucleic acid as defined herein and optionally a pharmaceutically acceptable carrier and/or vehicle.

As a first ingredient, the inventive pharmaceutical composition comprises the inventive nucleic acid as defined herein.

As a second ingredient the inventive pharmaceutical composition may comprise at least one additional pharmaceutically active component. A pharmaceutically active component in this connection is a compound that has a therapeutic effect to heal, ameliorate or prevent a particular indication or disease as mentioned herein, preferably cancer diseases, autoimmune disease, allergies or infectious diseases, cardiovascular diseases, diseases of the respiratory system, diseases of the digestive system, diseases of the skin, musculoskeletal disorders, disorders of the connective tissue, neoplasms, immune deficiencies, endocrine, nutritional and metabolic diseases, neural diseases, eye diseases, ear diseases and hereditary diseases. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions.

According to a specific aspect, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive nucleic acid sequence as vehicle, transfection or complexation agent.

The inventive pharmaceutical composition can additionally contain one or more auxiliary substances in order to increase its immunogenicity or immunostimulatory capacity, if desired. A synergistic action of the inventive nucleic acid as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) Ok cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

The inventive pharmaceutical composition as defined herein may also be administered orally in any orally acceptable dosage form including, but not limited to, capsules, tablets, aqueous suspensions or solutions.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive nucleic acid as defined herein suspended or dissolved in one or more carriers.

The inventive pharmaceutical composition typically comprises a "safe and effective amount" of the components of the inventive pharmaceutical composition, particularly of the inventive nucleic acid as defined herein. As used herein, a "safe and effective amount" means an amount of the inventive nucleic acid as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred embodiment, the inventive pharmaceutical composition (or the inventive nucleic acid as defined herein) may be provided or used as a vaccine. Typically, such a vaccine is as defined above for pharmaceutical compositions.

Additionally, such a vaccine typically contains the inventive nucleic acid as defined herein, which preferably encodes an antigen as defined above. Alternatively, such a vaccine may contain the inventive nucleic acid as defined herein and additional an antigen, preferably as a protein or peptide or as a nucleic acid encoding an antigen, e.g. as defined herein, or as any antigenic format as defined herein or all possible combinations thereof.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

The present invention furthermore provides several applications and uses of the inventive nucleic acid as defined herein, the inventive pharmaceutical composition, the inventive vaccine, both comprising the inventive nucleic acid as defined herein or of kits comprising same.

According to one specific embodiment, the present invention is directed to the first medical use of the inventive nucleic acid as defined herein as a medicament, preferably as an immunostimulating agent, adjuvant or vaccine or in the field of gene therapy.

According to another embodiment, the present invention is directed to the second medical use of the nucleic acid as defined herein, for the treatment of diseases as defined herein, preferably to the use of inventive nucleic acid as defined herein, of a pharmaceutical composition or vaccine comprising same or of kits comprising same for the preparation of a medicament for the prophylaxis, treatment and/or amelioration of various diseases as defined herein. Preferably, the pharmaceutical composition or a vaccine is used or to be administered to a patient in need thereof for this purpose.

Preferably, diseases as mentioned herein are selected from cancer or tumour diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a defined gene defect and are inherited according to Mendel's laws, cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and any disease which can be influenced by the present invention.

Cancer or tumour diseases as mentioned above preferably include e.g. colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBV-induced B-cell lymphoma), heptatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc.

Additionally, in the above context, infectious diseases are preferably selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), from bacterial infectious diseases such as miscarriage (prostate inflammation), anthrax, appendicitis, borreliosis, botulism, *Camphylobacter, Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and from infectious diseases caused by parasites, protozoa or fungi, such as amoebiasis, bilharziosis, Chagas disease, athlete's foot, yeast fungus spots, scabies, malaria, onchocercosis (river blindness), or fungal diseases, toxoplasmosis, trichomoniasis, trypanosomiasis (sleeping sickness), visceral Leishmaniosis, nappy/diaper dermatitis, schistosomiasis, fish poisoning (Ciguatera), candidosis, cutaneous Leishmaniosis, lambliasis (giardiasis), or sleeping sickness, or from infectious diseases caused by *Echinococcus*, fish tapeworm, fox tapeworm, canine tapeworm, lice, bovine tapeworm, porcine tapeworm, miniature tapeworm.

Furthermore, in the above context, allergies normally result in a local or systemic inflammatory response to these antigens or allergens and leading to immunity in the body against these allergens. Allergens in this context include e.g. grasses, pollens, molds, drugs, or numerous environmental triggers, etc. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, allergies to insect stings, skin allergies (leading to and including various rashes, such as eczema, hives (urticaria) and (contact) dermatitis), food allergies, allergies to medicine, etc. With regard to the present invention, e.g. an inventive nucleic acid, pharmaceutical composition or vaccine is provided, which encodes or contains an allergen (e.g. from a cat allergen, a dust allergen, a mite antigen, a plant antigen (e.g. a birch antigen) etc.) either as a protein, a nucleic acid encoding that protein allergen in combination with a nucleic acid of the invention as defined above or as an inventive nucleic acid. A pharmaceutical composition of the present invention may shift the (exceeding) immune response to a stronger TH1 response, thereby suppressing or attenuating the undesired IgE response.

Additionally, autoimmune diseases can be broadly divided into systemic and organ-specific or localised autoimmune disorders, depending on the principal clinico-pathologic features of each disease. Autoimmune disease may be divided into the categories of systemic syndromes, including SLE, Sjögren's syndrome, Scleroderma, Rheumatoid Arthritis and polymyositis or local syndromes which may be endocrinologic (DM Type 1, Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus), systemic lupus erythematosus (SLE), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), psoriasis, Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T-Cell Bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to one subunit of T-cell receptors in a non-specific fashion. Another explanation deduces autoimmune diseases from a molecular mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever. The present invention allows therefore provision of a nucleic acid or pharmaceutical composition or vaccine as defined herein encoding or containing e.g. an autoantigen (as protein, mRNA or DNA encoding an autoantigen protein) which typically allows the immune system to be desensitized.

According to an additional embodiment, the present invention is directed to the second medical use of the inventive nucleic acid as defined herein, for the treatment of diseases as defined herein by means of gene therapy.

In a further preferred embodiment, the inventive nucleic acid may be used for the preparation of a pharmaceutical composition or a vaccine, particularly for purposes as defined herein.

The inventive pharmaceutical composition or vaccine may furthermore be used for the treatment of a disease or a disorder as defined herein.

According to a final embodiment, the present invention also provides kits, particularly kits of parts. Such kits, particularly kits of parts, typically comprise as components alone or in combination with further components as defined herein at least one inventive nucleic acid as defined herein, the inventive pharmaceutical composition or vaccine comprising the inventive nucleic acid. The at least one inventive nucleic acid as defined herein, optionally in combination with further components as defined herein, the inventive pharmaceutical composition and/or the inventive vaccine may occur in one or different parts of the kit. As an example, e.g. at least one part of the kit may comprise at least one inventive nucleic acid as defined herein, and at least one further part of the kit at least one other component as defined herein, e.g. at least one other part of the kit may comprise at least one pharmaceutical composition or vaccine or a part thereof, e.g. at least one part of the kit may comprise the inventive nucleic acid as defined herein, at least one further part of the kit at least one other component as defined herein, at least one further part of the kit at least one component of the inventive pharmaceutical composition or vaccine or the inventive pharmaceutical composition or vaccine as a whole, and at least one further part of the kit e.g. at least one antigen, at least one pharmaceutical carrier or vehicle, etc. The kit or kit of parts may furthermore contain technical instructions with information on the administration and dosage of the inventive nucleic acid, the inventive pharmaceutical composition or the inventive vaccine or of any of its components or parts, e.g. if the kit is prepared as a kit of parts.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

BRIEF DESCRIPTION OF THE FIGURES

The following Figures are intended to illustrate the invention further and shall not be construed to limit the present invention thereto.

FIG. 1: shows the histone stem-loop consensus sequence generated from metazoan and protozoan stem loop sequences (as reported by Dávila López, M., & Samuelsson, T. (2008), *RNA* (New York, N.Y.), 14(1), 1-10. doi:10.1261/rna.782308). 4001 histone stem-loop sequences from metazoa and protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 2: shows the histone stem-loop consensus sequence generated from protozoan stem loop sequences (as reported by Dávila López, M., & Samuelsson, T. (2008), *RNA* (New York, N.Y.), 14(1), 1-10. doi:10.1261/rna.782308). 131 histone stem-loop sequences from protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 3: shows the histone stem-loop consensus sequence generated from metazoan stem loop sequences (as reported by Dávila López, M., & Samuelsson, T. (2008), *RNA* (New York, N.Y.), 14(1), 1-10. doi:10.1261/rna.782308). 3870 histone stem-loop sequences from metazoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 4: shows the histone stem-loop consensus sequence generated from vertebrate stem loop sequences (as reported by Dávila López, M., & Samuelsson, T. (2008), *RNA* (New York, N.Y.), 14(1), 1-10. doi:10.1261/rna.782308). 1333 histone stem-loop sequences from vertebrates were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 5: shows the histone stem-loop consensus sequence generated from human (*Homo sapiens*) stem loop sequences (as reported by Dávila López, M., & Samuelsson, T. (2008), *RNA* (New York, N.Y.), 14(1), 1-10. doi:10.1261/rna.782308). 84 histone stem-loop sequences from humans were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIGS. 6 to 17: show mRNAs from in vitro transcription.

Figure 18:
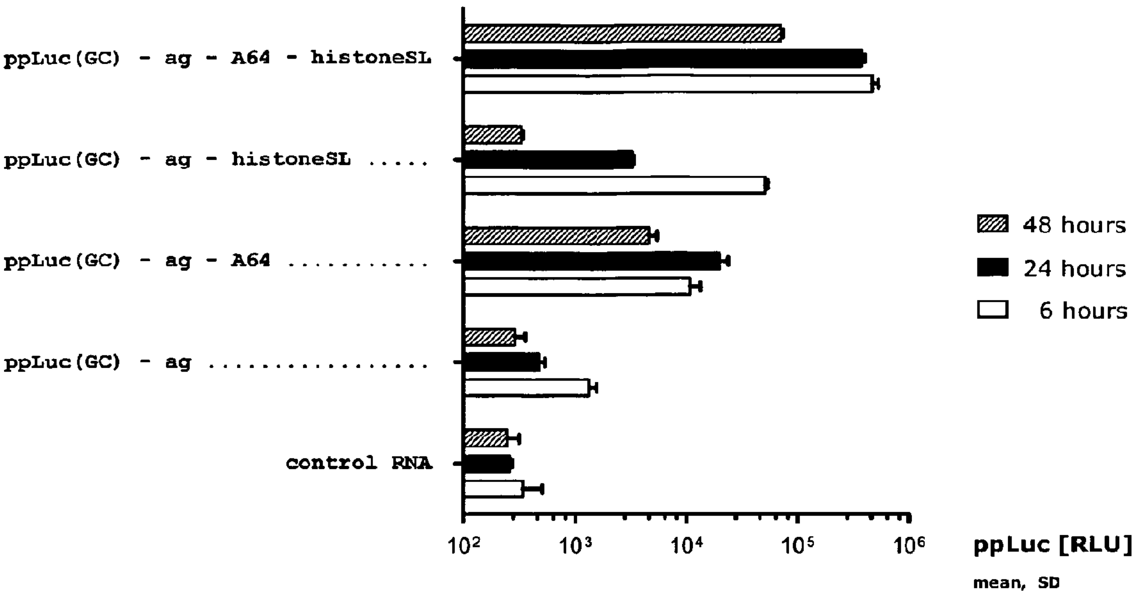

Given are the designation and the sequence of mRNAs obtained by in vitro transcription. The following abbreviations are used:

ppLuc (GC): GC-enriched mRNA sequence coding for *Photinus pyralis* luciferase ag: 3' untranslated region (UTR) of the alpha globin gene A64: poly(A)-sequence with 64 adenylates A120: poly(A)-sequence with 120 adenylates histoneSL: histone stem-loop aCPSL: stem loop which has been selected from a library for its specific binding of the αCP-2KL protein PolioCL: 5' clover leaf from Polio virus genomic RNA G30: poly(G) sequence with 30 guanylates U30: poly(U) sequence with 30 uridylates SL: unspecific/artificial stem-loop N32: unspecific sequence of 32 nucleotides Within the sequences, the following elements are highlighted: ppLuc(GC) ORF (capital letters), ag (bold), histoneSL (underlined), further distinct sequences tested (italic).

FIG. 6: shows the mRNA sequence of ppLuc(GC)-ag (SEQ ID NO: 43).

By linearization of the original vector at the restriction site immediately following the alpha-globin 3'-UTR (ag), mRNA is obtained lacking a poly(A) sequence.

FIG. 7: shows the mRNA sequence of ppLuc(GC)-ag-A64 (SEQ ID NO: 44).

By linearization of the original vector at the restriction site immediately following the A64 poly(A)-sequence, mRNA is obtained ending with an A64 poly(A) sequence.

FIG. 8: shows the mRNA sequence of ppLuc(GC)-ag-histoneSL (SEQ ID NO: 45).

The A64 poly(A) sequence was replaced by a histoneSL. The histone stem-loop sequence used in the examples was obtained from Cakmakci et al. (2008). *Molecular and Cellular Biology,* 28(3), 1182-1194.

FIG. 9: shows the mRNA sequence of ppLuc(GC)-ag-A64-histoneSL (SEQ ID NO: 46).

The histoneSL was appended 3' of A64 poly(A).

FIG. 10: shows the mRNA sequence of ppLuc(GC)-ag-A120 (SEQ ID NO: 47).

The A64 poly(A) sequence was replaced by an A120 poly(A) sequence.

FIG. 11: shows the mRNA sequence of ppLuc(GC)-ag-A64-ag (SEQ ID NO: 48).

A second alpha-globin 3'-UTR was appended 3' of A64 poly(A).

FIG. 12: shows the mRNA sequence of ppLuc(GC)-ag-A64-aCPSL (SEQ ID NO: 49).

A stem loop was appended 3' of A64 poly(A). The stem loop has been selected from a library for its specific binding of the αCP-2KL protein (Thisted et al., (2001), The Journal of Biological Chemistry, 276(20), 17484-17496). αCP-2KL is an isoform of αCP-2, the most strongly expressed αCP protein (alpha-globin mRNA poly(C) binding protein) (Makeyev et al., (2000), Genomics, 67(3), 301-316), a group of RNA binding proteins, which bind to the alpha-globin 3'-UTR (Chkheidze et al., (1999), Molecular and Cellular Biology, 19(7), 4572-4581).

FIG. 13: shows the mRNA sequence of ppLuc(GC)-ag-A64-PolioCL (SEQ ID NO: 50).

The 5' clover leaf from Polio virus genomic RNA was appended 3' of A64 poly(A).

FIG. 14: shows the mRNA sequence of ppLuc(GC)-ag-A64-G30 (SEQ ID NO: 51)

A stretch of 30 guanylates was appended 3' of A64 poly(A).

FIG. 15: shows the mRNA sequence of ppLuc(GC)-ag-A64-U30 (SEQ ID NO: 52)

A stretch of 30 uridylates was appended 3' of A64 poly(A).

FIG. 16: shows the mRNA sequence of ppLuc(GC)-ag-A64-SL (SEQ ID NO: 53)

A stem loop was appended 3' of A64 poly(A). The upper part of the stem and the loop were taken from (Babendure et al., (2006), *RNA* (New York, N.Y.), 12(5), 851-861). The stem loop consists of a 17 base pair long, CG-rich stem and a 6 base long loop.

FIG. 17: shows ppLuc(GC)-ag-A64-N32 (SEQ ID NO: 54)

By linearization of the original vector at an alternative restriction site, mRNA is obtained with 32 additional nucleotides following poly(A).

FIG. 18: shows that the combination of poly(A) and histoneSL increases protein expression from mRNA in a synergistic manner.

The effect of poly(A) sequence, histoneSL, and the combination of poly(A) and histoneSL on luciferase expression from mRNA was examined. Therefore different mRNAs were electroporated into HeLa cells. Luciferase levels were measured at 6, 24, and 48 hours after transfection. Little luciferase is expressed from mRNA having neither poly(A) sequence nor histoneSL. Both a poly(A) sequence or the histoneSL increase the luciferase level. Strikingly however, the combination of poly(A) and histoneSL further strongly increases the luciferase level, manifold above the level observed with either of the individual elements, thus acting synergistically. Data are graphed as mean RLU±SD (relative light units±standard deviation) for triplicate transfections. Specific RLU are summarized in Example 11.2.

Figure 19:
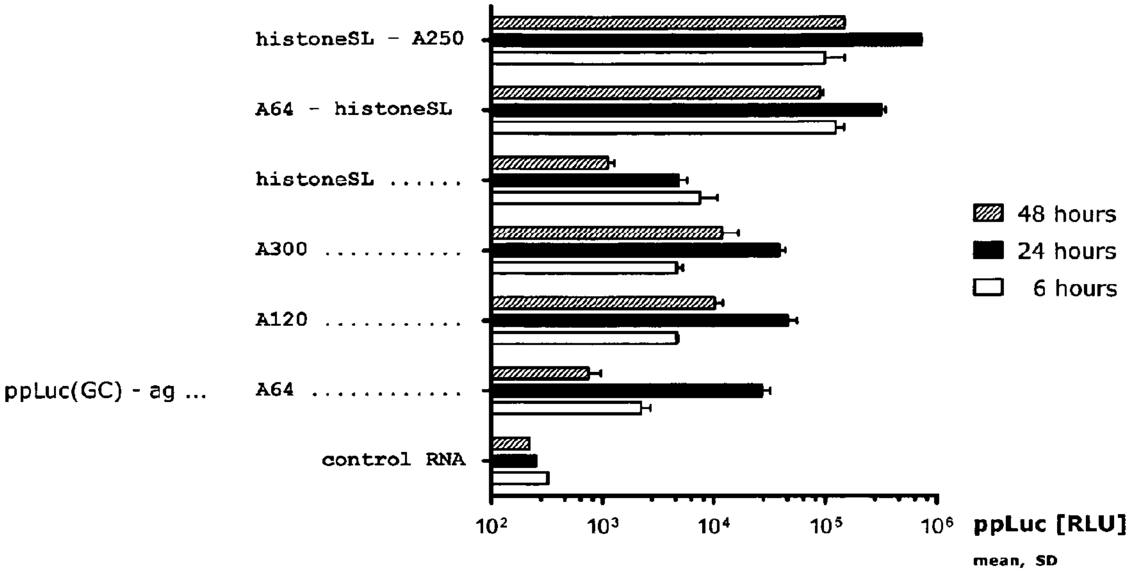

FIG. 19: shows that the combination of poly(A) and histoneSL increases protein expression from mRNA irrespective of their order.

The effect of poly(A) sequence, histoneSL, the combination of poly(A) and histoneSL, and their order on luciferase expression from mRNA was examined. Therefore different mRNAs were lipofected into HeLa cells. Luciferase levels were measured at 6, 24, and 48 hours after the start of transfection. Both an A64 poly(A) sequence or the histoneSL give rise to comparable luciferase levels. Increasing the length of the poly(A) sequence from A64 to A120 or to A300 increases the luciferase level moderately. In contrast, the combination of poly(A) and histoneSL increases the luciferase level much further than lengthening of the poly(A) sequence. The combination of poly(A) and histoneSL acts synergistically as it increases the luciferase level manifold above the level observed with either of the individual elements. The synergistic effect of the combination of poly(A) and histoneSL is seen irrespective of the order of poly(A) and histoneSL and irrespective of the length of poly(A) with A64-histoneSL or histoneSL-A250 mRNA. Data are graphed as mean RLU±SD for triplicate transfections. Specific RLU are summarized in Example 11.3.

Figure 20:
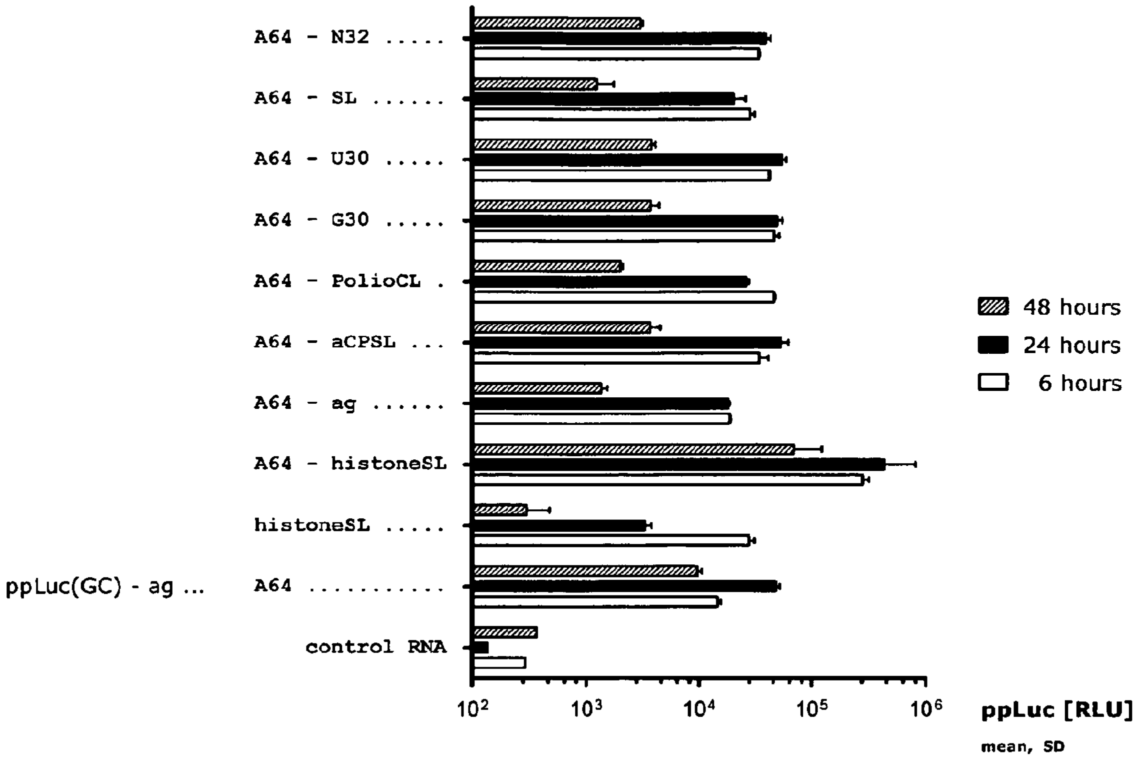

FIG. 20: shows that the rise in protein expression by the combination of poly(A) and histoneSL is specific.

The effect of combining poly(A) and histoneSL or poly (A) and alternative sequences on luciferase expression from mRNA was examined. Therefore different mRNAs were electroporated into HeLa cells. Luciferase levels were measured at 6, 24, and 48 hours after transfection. Both a poly(A) sequence or the histoneSL give rise to comparable luciferase levels. The combination of poly(A) and histoneSL strongly increases the luciferase level, manifold above the level observed with either of the individual elements, thus acting synergistically. In contrast, combining poly(A) with any of the other sequences is without effect on the luciferase level compared to mRNA containing only a poly(A) sequence. Thus, the combination of poly(A) and histoneSL acts specifically and synergistically. Data are graphed as mean RLU±SD for triplicate transfections. Specific RLU are summarized in Example 11.4.

Figure 21:
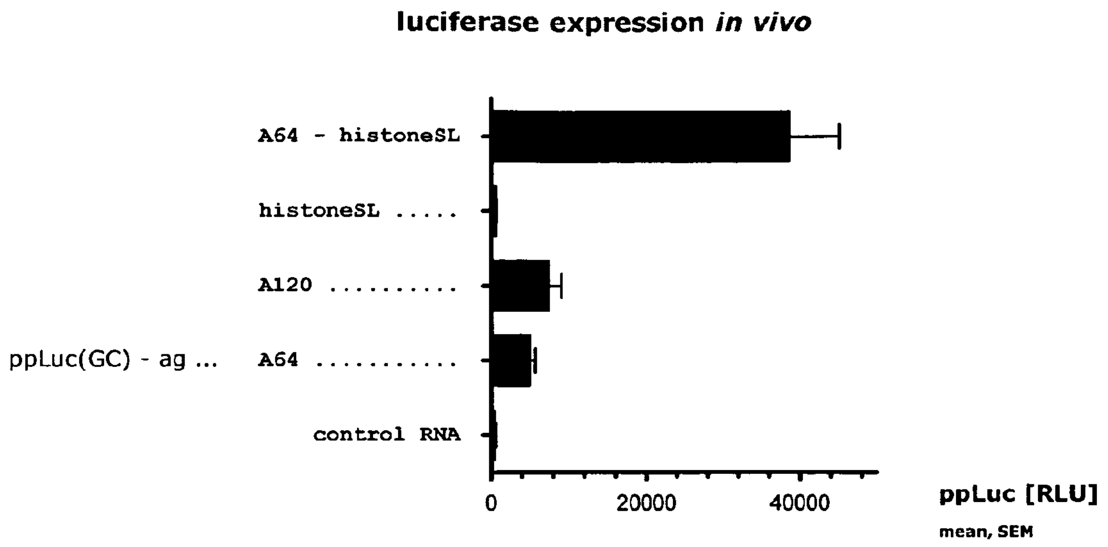

FIG. 21: shows that the combination of poly(A) and histoneSL increases protein expression from mRNA in a synergistic manner in vivo.

The effect of poly(A) sequence, histoneSL, and the combination of poly(A) and histoneSL on luciferase expression from mRNA in vivo was examined. Therefore different mRNAs were injected intradermally into mice. Mice were sacrificed 16 hours after injection and Luciferase levels at the injection sites were measured. Luciferase is expressed from mRNA having either a histoneSL or a poly(A) sequence. Strikingly however, the combination of poly(A) and histoneSL strongly increases the luciferase level, manifold above the level observed with either of the individual elements, thus acting synergistically. Data are graphed as mean RLU±SEM (relative light units±standard error of mean). Specific RLU are summarized in Example 11.5.

Figure 22:
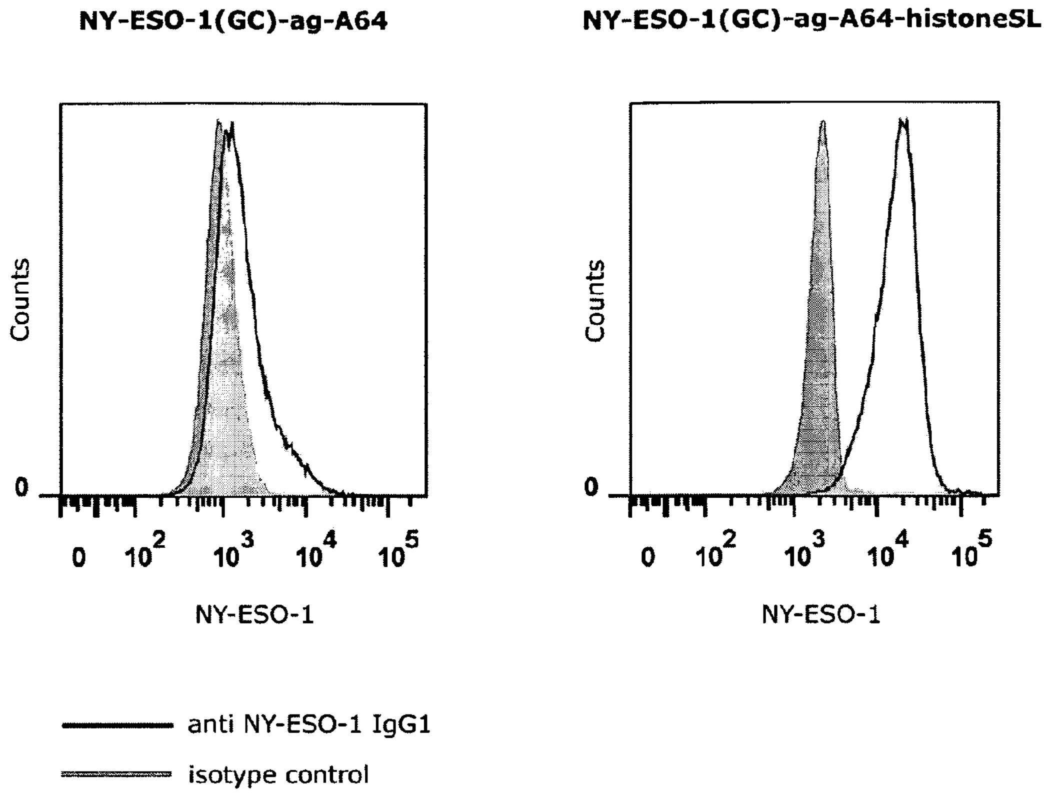

FIG. 22: shows that the combination of poly(A) and histoneSL increases NY-ESO-1 protein expression from mRNA.

The effect of poly(A) sequence and the combination of poly(A) and histoneSL on NY-ESO-1 expression from mRNA was examined. Therefore different mRNAs were electroporated into HeLa cells. NY-ESO-1 levels were measured at 24 hours after transfection by flow cytometry. NY-ESO-1 is expressed from mRNA having only a poly(A) sequence. Strikingly however, the combination of poly(A) and histoneSL strongly increases the NY-ESO-1 level, manifold above the level observed with only a poly(A) sequence. Data are graphed as counts against fluorescence intensity. Median fluorescence intensities (MFI) are summarized in Example 11.6.

Figure 23:
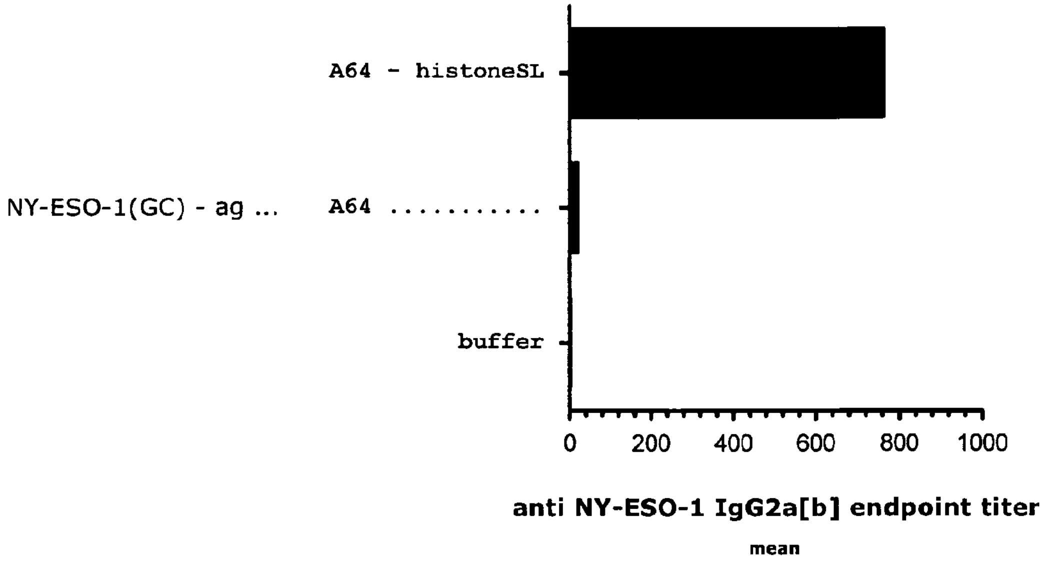

FIG. 23: shows that the combination of poly(A) and histoneSL increases the level of antibodies elicited by vaccination with mRNA.

The effect of poly(A) sequence and the combination of poly(A) and histoneSL on the induction of anti NY-ESO-1 antibodies elicited by vaccination with mRNA was examined. Therefore C57BL/6 mice were vaccinated intradermally with different mRNAs complexed with protamine. The level of NY-ESO-1-specific antibodies in vaccinated and control mice was analyzed by ELISA with serial dilutions of sera. Anti NY-ESO-1 IgG2a[b] is induced by mRNA having only a poly(A) sequence. Strikingly however, the combination of poly (A) and histoneSL strongly increases the anti NY-ESO-1 IgG2a[b] level, manifold above the level observed with only a poly(A) sequence. Data are graphed as mean endpoint titers. Mean endpoint titers are summarized in Example 11.7.

EXAMPLES

The following Examples are intended to illustrate the invention further and shall not be construed to limit the present invention thereto.

1. Generation of Histone-Stem-Loop Consensus Sequences

Prior to the experiments, histone stem-loop consensus sequences were determined on the basis of metazoan and protozoan histone stem-loop sequences. Sequences were taken from the supplement provided by Lopez et al. (Dávila López, M., & Samuelsson, T. (2008), RNA (New York, N.Y.), 14(1), 1-10. doi:10.1261/rna.782308), who identified a large number of natural histone stem-loop sequences by searching genomic sequences and expressed sequence tags. First, all sequences from metazoa and protozoa (4001 sequences), or all sequences from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. In addition, more restrictive consensus sequences were also obtained, increasingly emphasizing conserved nucleotides 2. Preparation of DNA-Templates A vector for in vitro transcription was constructed containing a T7 promoter followed by a GC-enriched sequence coding for *Photinus pyralis* luciferase (ppLuc (GC)), the center part of the 3' untranslated region (UTR) of alpha-globin (ag), and a poly(A) sequence. The poly(A) sequence was immediately followed by a restriction site used for linearization of the vector before in vitro transcription in order to obtain mRNA ending in an A64 poly(A) sequence. mRNA obtained from this vector accordingly by in vitro transcription is designated as "ppLuc(GC)-ag-A64".

Linearization of this vector at alternative restriction sites before in vitro transcription allowed to obtain mRNA either extended by additional nucleotides 3' of A64 or lacking A64. In addition, the original vector was modified to include alternative sequences. In summary, the following mRNAs were obtained from these vectors by in vitro transcription (mRNA sequences are given in FIGS. 6 to 17):

ppLuc(GC)-ag (SEQ ID NO: 43)
ppLuc(GC)-ag-A64 (SEQ ID NO: 44)
ppLuc(GC)-ag-histoneSL (SEQ ID NO: 45)
ppLuc(GC)-ag-A64-histoneSL (SEQ ID NO: 46)
ppLuc(GC)-ag-A120 (SEQ ID NO: 47)
ppLuc(GC)-ag-A64-ag (SEQ ID NO: 48)
ppLuc(GC)-ag-A64-aCPSL (SEQ ID NO: 49)
ppLuc(GC)-ag-A64-PolioCL (SEQ ID NO: 50)
ppLuc(GC)-ag-A64-G30 (SEQ ID NO: 51)
ppLuc(GC)-ag-A64-U30 (SEQ ID NO: 52)
ppLuc(GC)-ag-A64-SL (SEQ ID NO: 53)
ppLuc(GC)-ag-A64-N32 (SEQ ID NO: 54)

3. In Vitro Transcription

The DNA-template according to Example 2 was linearized and transcribed in vitro using T7-Polymerase. The DNA-template was then digested by DNase-treatment. All mRNA-transcripts contained a 5'-CAP structure obtained by adding an excess of N7-Methyl-Guanosine-5'-Triphosphate-5'-Guanosine to the transcription reaction. mRNA thus obtained was purified and resuspended in water.

4. Enzymatic Adenylation of mRNA

Two mRNAs were enzymatically adenylated:

ppLuc(GC)-ag-A64 and ppLuc(GC)-ag-histoneSL.

To this end, RNA was incubated with *E. coli* Poly(A)-polymerase and ATP (Poly(A) Polymerase Tailing Kit, Epicentre, Madison, USA) following the manufacturer's instructions. mRNA with extended poly(A) sequence was purified and resuspended in water. The length of the poly(A) sequence was determined via agarose gel electrophoresis. Starting mRNAs were extended by approximately 250 adenylates, the mRNAs obtained are designated as ppLuc(GC)-ag-A300 and ppLuc(GC)-ag-histoneSL-A250, respectively.

5. Luciferase Expression by mRNA Electroporation

HeLa cells were trypsinized and washed in OPTI-MEM®. $1\times10^5$ cells in 200 μl of OPTI-MEM® each were electroporated with 0.5 μg of ppLuc-encoding mRNA. As a control, mRNA not coding for ppLuc was electroporated separately. Electroporated cells were seeded in 24-well plates in 1 ml of RPMI 1640 medium. 6, 24, or 48 hours after transfection, medium was aspirated and cells were lysed in 200 μl of lysis buffer (25 mM Tris, pH 7.5 (HCl), 2 mM EDTA, 10% glycerol, 1% TRITON™ X-100, 2 mM DTT, 1 mM PMSF). Lysates were stored at −20° C. until ppLuc activity was measured.

6. Luciferase Expression by mRNA Lipofection

HeLa cells were seeded in 96 well plates at a density of $2\times10^4$ cells per well. The following day, cells were washed in OPTI-MEM® and then transfected with 0.25 μg of LIPOFECTIN®-complexed ppLuc-encoding mRNA in 150 μl of OPTI-MEM®. As a control, mRNA not coding for ppLuc was lipofected separately. In some wells, OPTI-MEM® was aspirated and cells were lysed in 200 μl of lysis buffer 6 hours after the start of transfection. In the remaining wells, OPTI-MEM® was exchanged for RPMI 1640 medium at that time. In these wells, medium was aspirated and cells were lysed in 200 μl of lysis buffer 24 or 48 hours after the start of transfection. Lysates were stored at −20° C. until ppLuc activity was measured.

7. Luciferase Measurement ppLuc activity was measured as relative light units (RLU) in a BioTek SYNERGY™ HT plate reader at 5 seconds measuring time using 50 μl of lysate and 200 μl of luciferin buffer (25 mM Glycylglycin, pH 7.8 (NaOH), 1.5 mM $MgSO_4$, 2 mM ATP, 75 μM luciferin). Specific RLU were calculated by subtracting RLU of the control RNA from total RLU.

8. Luciferase Expression by Intradermal mRNA Injection (Luciferase Expression In Vivo)

Mice were anaesthetized with a mixture of ROMPUN™ and KETAVET™. Each ppLuc-encoding mRNA was injected intradermally (0.5 μg of mRNA in 50 μl per injection). As a control, mRNA not coding for ppLuc was injected separately. 16 hours after injection, mice were sacrificed and tissue collected. Tissue samples were flash frozen in liquid nitrogen and lysed in a tissue lyser (Qiagen) in 800 μl of lysis buffer (25 mM Tris, pH 7.5 (HCl), 2 mM EDTA, 10% glycerol, 1% TRITON™ X-100, 2 mM DTT, 1 mM PMSF). Subsequently samples were centrifuged at 13500 rpm at 4° C. for 10 minutes. Lysates were stored at −80° C. until ppLuc activity was measured (see 7. luciferase measurement).

9. NY-ESO-1 Expression by mRNA Electroporation

HeLa cells were trypsinized and washed in opti-MEM. $2\times10^5$ cells in 200 μl of opti-MEM were electroporated with 10 μg of NY-ESO-1-encoding mRNA. Cells from three electroporations were combined and seeded in a 6-well plate in 2 ml of RPMI 1640 medium. 24 hours after transfection, cells were harvested and transferred into a 96 well V-bottom plate (2 wells per mRNA). Cells were washed with phosphate buffered saline (PBS) and permeabilized with 200 μl per well of CYTOFIX™/CYTOPERM™ (Becton Dickinson (BD)). After 15 minutes, cells were washed with PERMWASH™ (BD). Then, cells were incubated for 1 hour at room temperature with either mouse anti-NY-ESO-1 IgG1 or an isotype control (20 μg/ml). Cells were washed twice with PERMWASH™ again. Next, cells were incubated for 1 hour at 4° C. with a 1:500 dilution of Alexa-647 coupled goat-anti-mouse IgG. Finally, cells were washed twice with PERMWASH™. Cells were resuspended in 200 μl of buffer (PBS, 2% FCS, 2 mM EDTA, 0.01% sodium azide). NY-ESO-1 expression was quantified by flow cytometry as median fluorescence intensity (MFI).

10. Induction of Anti NY-ESO-1 Antibodies by Vaccination with mRNA

C57BL/6 mice were vaccinated intradermally with NY-ESO-1-encoding mRNA complexed with protamine (5 times in 14 days). Control mice were treated with buffer. The level of NY-ESO-1-specific antibodies in vaccinated and control mice was analyzed 8 days after the last vaccination by ELISA: 96 well ELISA plates (Nunc) were coated with 100 μl per well of 10 μg/ml recombinant NY-ESO-1 protein for 16 hours at 4° C. Plates were washed two times with wash buffer (PBS, 0.05% TweenTWEEN®-20). To block unspecific binding, plates were then incubated for 2 hours at 37° C. with blocking buffer (PBS, 0.05% TweenTWEEN®-20, 1% BSA). After blocking, 100 μl per well of serially diluted mouse sera were added and incubated for 4 hours at room temperature. Plates were then washed three times with wash buffer. Next, 100 μl per well of biotinylated rat anti-mouse IgG2a[b] detection antibody (BD Biosciences) diluted 1:600 in blocking buffer was allowed to bind for 1 hour at room temperature. Plates were washed again three times with wash buffer, followed by incubation for 30 minutes at room temperature with 100 μl per well of horseradish peroxidase-coupled streptavidin. After four washes with wash buffer, 100 μl per well of 3,3',5,5'-tetramethylbenzidine (Thermo Scientific) was added. Upon the resulting change in color 100 μl per well of 20% sulfuric acid was added. Absorbance was measured at 405 nm.

11. Results 11.1 Histone Stem-Loop Sequences:

In order to characterize histone stem-loop sequences, sequences from metazoa and protozoa (4001 sequences), or from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. Within the consensus sequence of metazoa and protozoa combined, 3 nucleotides are conserved, a T/U in the loop and a G and a C in the stem, forming a base pair. Structurally, typically a 6 base-pair stem and a loop of 4 nucleotides is formed. However, deviating structures are common: Of 84 human histone stem-loops, two contain a stem of only 5 nucleotides comprising 4 base-pairs and one mismatch. Another human histone stem-loop contains a stem of only 5 base-pairs. Four more human histone stem-loops contain a 6 nucleotide long stem, but include one mismatch at three different positions, respectively. Furthermore, four human histone stem-loops contain one wobble base-pair at two different positions, respectively. Concerning the loop, a length of 4 nucleotides seems not to be strictly required, as a loop of 5 nucleotides has been identified in *D. discoideum*.

In addition to the consensus sequences representing all nucleotides present in the sequences analyzed, more restrictive consensus sequences were also obtained, increasingly emphasizing conserved nucleotides. In summary, the following sequences were obtained:

(Cons): represents all nucleotides present (99%): represents at least 99% of all nucleotides present (95%): represents at least 95% of all nucleotides present (90%): represents at least 90% of all nucleotides present The results of the analysis of histone stem-loop sequences are summarized in the following Tables 1 to 5 (see also FIGS. 1 to 5):

TABLE 1

Metzoan and protozoan histone stem-loop consensus sequence: (based on an alignment of 4001 metazoan and protozoan histone stem-loop sequences) (see also FIG. 1)

| | | | | | | | | | | | | | |
|---|---|---|---|---|---|---|---|---|---|---|---|---|---|
| | | | | | | < | < | < | < | < | < | • | • |
| # A | 2224 | 1586 | 3075 | 2872 | 1284 | 184 | 0 | 13 | 12 | 9 | 1 | 47 | 59 |
| # T | 172 | 188 | 47 | 205 | 19 | 6 | 0 | 569 | 1620 | 199 | 3947 | 3830 | 3704 |
| # C | 1557 | 2211 | 875 | 918 | 2675 | 270 | 0 | 3394 | 2342 | 3783 | 51 | 119 | 227 |
| # G | 25 | 16 | 4 | 6 | 23 | 3541 | 4001 | 25 | 27 | 10 | 2 | 5 | 11 |
| Cons | N* | N* | N | N | N | N | G | N | N | N | N | N | N |
| 99% | H* | H* | H | H | V | V | G | Y | Y | Y | Y | H | H |
| 95% | M* | H* | M | H | M | S | G | Y | Y | Y | T | T | Y |
| 90% | M* | M* | M | M | M | S | G | Y | Y | C | T | T | T |
| | • | • | > | > | > | > | > | > | | | | | |
| # A | 0 | 675 | 3818 | 195 | 1596 | 523 | 0 | 14 | 3727 | 61 | 771 | 2012 | 2499 |
| # T | 4001 | 182 | 1 | 21 | 15 | 11 | 0 | 179 | 8 | 64 | 557 | 201 | 690 |
| # C | 0 | 3140 | 7 | 50 | 31 | 16 | 4001 | 3543 | 154 | 3870 | 2636 | 1744 | 674 |
| # G | 0 | 4 | 175 | 3735 | 2359 | 3451 | 0 | 265 | 112 | 4 | 37 | 43 | 138 |
| Cons | T | N | N | N | N | N | C | N | N | N | N* | N* | N* |
| 99% | T | H | R | V | V | R | C | B | V | H | H* | N* | N* |
| 95% | T | M | A | R | R | R | C | S | M | C | H* | H* | H* |
| 90% | T | M | A | G | R | R | C | S | A | C | H* | M* | H* |

TABLE 2

Protozoan histone stem-loop consensus sequence: (based on an alignment of 131 protozoan histone stem-loop sequences) (see also FIG. 2)

| | | | | | | | | | | | | | | | | | | | | | | | | | | |
|---|---|---|---|---|---|---|---|---|---|---|---|---|---|---|---|---|---|---|---|---|---|---|---|---|---|---|
| | | | | | | < | < | < | < | < | < | • | • | • | • | > | > | > | > | > | > | | | | | |
| # A | 52 | 32 | 71 | 82 | 76 | 13 | 0 | 12 | 12 | 9 | 1 | 46 | 3 | 0 | 75 | 82 | 53 | 79 | 20 | 0 | 4 | 94 | 17 | 35 | 74 | 56 |
| # T | 20 | 32 | 37 | 21 | 8 | 3 | 0 | 21 | 85 | 58 | 86 | 70 | 65 | 131 | 28 | 1 | 17 | 13 | 10 | 0 | 15 | 7 | 31 | 32 | 20 | 28 |
| # C | 45 | 59 | 20 | 25 | 38 | 0 | 0 | 86 | 8 | 54 | 42 | 13 | 58 | 0 | 27 | 2 | 6 | 31 | 10 | 131 | 112 | 5 | 82 | 58 | 30 | 40 |
| # G | 14 | 8 | 3 | 3 | 9 | 115 | 131 | 12 | 26 | 10 | 2 | 2 | 5 | 0 | 1 | 46 | 55 | 8 | 91 | 0 | 0 | 25 | 1 | 6 | 7 | 7 |
| Cons | N* | N* | N | N | N | D | G | N | N | N | N | N | N | T | N | N | N | N | N | C | H | N | N | N* | N* | N* |
| 99% | N* | N* | N | N | N | D | G | N | N | N | B | N | N | T | H | V | N | N | N | C | H | N | H | N* | N* | N* |
| 95% | N* | N* | H | H | N | R | G | N | N | N | Y | H | B | T | H | R | D | N | N | C | Y | D | H | H* | N* | N* |
| 90% | N* | H* | H | H | V | R | G | N | D | B | Y | H | Y | T | H | R | D | H | N | C | Y | R | H | H* | H* | H* |

TABLE 3

Metazoan histone stem-loop consensus sequence: (based on an alignment of 3870 (including 1333 vertebrate sequences) metazoan histone stem-loop sequences) (see also FIG. 3)

| | | | | | | | | | | | | | |
|---|---|---|---|---|---|---|---|---|---|---|---|---|---|
| | | | | | | < | < | < | < | < | < | • | • |
| # A | 2172 | 1554 | 3004 | 2790 | 1208 | 171 | 0 | 1 | 0 | 0 | 0 | 1 | 56 |
| # T | 152 | 156 | 10 | 184 | 11 | 3 | 0 | 548 | 1535 | 141 | 3861 | 3760 | 3639 |
| # C | 1512 | 2152 | 855 | 893 | 2637 | 270 | 0 | 3308 | 2334 | 3729 | 9 | 106 | 169 |
| # G | 11 | 8 | 1 | 3 | 14 | 3426 | 3870 | 13 | 1 | 0 | 0 | 3 | 6 |
| Cons | N* | N* | N | N | N | N | G | N | B | Y | Y | N | N |
| 99% | H* | H* | M | H | M | V | G | Y | Y | Y | T | Y | H |
| 95% | M* | M* | M | M | M | S | G | Y | Y | C | T | T | Y |
| 90% | M* | M* | M | M | M | S | G | Y | Y | C | T | T | T |
| | • | • | > | > | > | > | > | > | | | | | |
| # A | 0 | 600 | 3736 | 142 | 1517 | 503 | 0 | 10 | 3633 | 44 | 736 | 1938 | 2443 |
| # T | 3870 | 154 | 0 | 4 | 2 | 1 | 0 | 164 | 1 | 33 | 525 | 181 | 662 |
| # C | 0 | 3113 | 5 | 44 | 0 | 6 | 3870 | 3431 | 149 | 3788 | 2578 | 1714 | 634 |
| # G | 0 | 3 | 129 | 3680 | 2351 | 3360 | 0 | 265 | 87 | 3 | 31 | 36 | 131 |
| Cons | T | N | V | N | D | N | C | N | N | N | N* | N* | N* |
| 99% | T | H | R | V | R | R | C | B | V | M | H* | H* | N* |
| 95% | T | M | A | G | R | R | C | S | M | C | H* | H* | H* |
| 90% | T | M | A | G | R | R | C | S | A | C | H* | M* | H* |

TABLE 4

| Vertebrate histone stem-loop consensus sequence: (based on an alignment of 1333 vertebrate histone stem-loop sequences) (see also FIG. 4) | | | | | | | | | | | | | |
|---|---|---|---|---|---|---|---|---|---|---|---|---|---|
| | | | | | | < | < | < | < | < | < | • | • |
| # A | 661 | 146 | 1315 | 1323 | 920 | 8 | 0 | 1 | 0 | 0 | 0 | 1 | 4 |
| # T | 63 | 121 | 2 | 2 | 6 | 2 | 0 | 39 | 1217 | 2 | 1331 | 1329 | 1207 |
| # C | 601 | 1062 | 16 | 6 | 403 | 1 | 0 | 1293 | 116 | 1331 | 2 | 0 | 121 |
| # G | 8 | 4 | 0 | 2 | 4 | 1322 | 1333 | 0 | 0 | 0 | 0 | 3 | 1 |
| Cons | N* | N* | H | N | N | N | G | H | Y | Y | Y | D | N |
| 99% | H* | H* | M | A | M | G | G | Y | Y | C | T | T | Y |
| 95% | H* | H* | A | A | M | G | G | C | Y | C | T | T | Y |
| 90% | M* | M* | A | A | M | G | G | C | T | C | T | T | T |
| | • | • | > | > | > | > | > | > | | | | | |
| # A | 0 | 441 | 1333 | 0 | 1199 | 21 | 0 | 1 | 1126 | 26 | 81 | 380 | 960 |
| # T | 1333 | 30 | 0 | 1 | 0 | 1 | 0 | 2 | 1 | 22 | 91 | 91 | 12 |
| # C | 0 | 862 | 0 | 2 | 0 | 0 | 1333 | 1328 | 128 | 1284 | 1143 | 834 | 361 |
| # G | 0 | 0 | 0 | 1330 | 134 | 1311 | 0 | 2 | 78 | 1 | 18 | 28 | 0 |
| Cons | T | H | A | B | R | D | C | N | N | N | N* | N* | H* |
| 99% | T | H | A | G | R | R | C | C | V | H | N* | N* | M* |
| 95% | T | M | A | G | R | G | C | C | V | C | H* | H* | M* |
| 90% | T | M | A | G | R | G | C | C | M | C | Y* | M* | M* |

TABLE 5

| *Homo sapiens* histone stem-loop consensus sequence: (based on an alignment of 84 human histone stem-loop sequences) (see also FIG. 5) | | | | | | | | | | | | | | | | | | | | | | | | | | |
|---|---|---|---|---|---|---|---|---|---|---|---|---|---|---|---|---|---|---|---|---|---|---|---|---|---|---|
| | | | | | | < | < | < | < | < | < | • | • | • | • | > | > | > | > | > | > | | | | | |
| # A | 10 | 17 | 84 | 84 | 76 | 1 | 0 | 1 | 0 | 0 | 0 | 1 | 0 | 0 | 12 | 84 | 0 | 65 | 3 | 0 | 0 | 69 | 5 | 0 | 10 | 64 |
| # T | 8 | 6 | 0 | 0 | 2 | 2 | 0 | 1 | 67 | 0 | 84 | 80 | 81 | 84 | 5 | 0 | 0 | 0 | 0 | 0 | 0 | 0 | 4 | 25 | 24 | 3 |
| # C | 62 | 61 | 0 | 0 | 6 | 0 | 0 | 82 | 17 | 84 | 0 | 0 | 3 | 0 | 67 | 0 | 1 | 0 | 0 | 84 | 84 | 5 | 75 | 57 | 44 | 17 |
| # G | 4 | 0 | 0 | 0 | 0 | 81 | 84 | 0 | 0 | 0 | 0 | 3 | 0 | 0 | 0 | 0 | 83 | 19 | 81 | 0 | 0 | 10 | 0 | 2 | 6 | 0 |
| Cons | N* | H* | A | A | H | D | G | H | Y | C | T | D | Y | T | H | A | S | R | R | C | C | V | H | B* | N* | H* |
| 99% | N* | H* | A | A | H | D | G | H | Y | C | T | D | Y | T | H | A | S | R | R | C | C | V | H | B* | N* | H* |
| 95% | H* | H* | A | A | M | G | G | C | Y | C | T | T | T | T | H | A | G | R | G | C | C | V | M | Y* | N* | M* |
| 90% | H* | M* | A | A | A | G | G | C | Y | C | T | T | T | T | M | A | G | R | G | C | C | R | M | Y* | H* | M* |

Wherein the used abbreviations were defined as followed:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | present or not | Base may be present or not |

11.2 The Combination of Poly(A) and HistoneSL Increases Protein Expression from mRNA in a Synergistic Manner.

To investigate the effect of the combination of poly(A) and histoneSL on protein expression from mRNA, mRNAs with different sequences 3' of the alpha-globin 3'-UTR were synthesized: mRNAs either ended just 3' of the 3'-UTR, thus lacking both poly(A) sequence and histoneSL, or contained either an A64 poly(A) sequence or a histoneSL instead, or both A64 poly(A) and histoneSL 3' of the 3'-UTR. Luciferase-encoding mRNAs or control mRNA were electroporated into HeLa cells. Luciferase levels were measured at 6, 24, and 48 hours after transfection (see following Table 6 and FIG. 18).

TABLE 6

| mRNA | RLU at 6 hours | RLU at 24 hours | RLU at 48 hours |
|---|---|---|---|
| ppLuc(GC)-ag-A64-histoneSL | 466553 | 375169 | 70735 |
| ppLuc(GC)-ag-histoneSL | 50947 | 3022 | 84 |
| ppLuc(GC)-ag-A64 | 10471 | 19529 | 4364 |
| ppLuc(GC)-ag | 997 | 217 | 42 |

Little luciferase was expressed from mRNA having neither poly(A) sequence nor histoneSL. Both a poly(A) sequence or the histoneSL increased the luciferase level to a similar extent. Either mRNA gave rise to a luciferase level much higher than did mRNA lacking both poly(A) and histoneSL. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 7).

TABLE 7

| | A64 | histoneSL | RLU at 6 hours | RLU at 24 hours | RLU at 48 hours |
|---|---|---|---|---|---|
| | + | + | 466553 | 375169 | 70735 |
| | − | + | 50947 | 3022 | 84 |
| | + | − | 10471 | 19529 | 4364 |
| Synergy | | | 7.6 | 16.6 | 15.9 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was up to 16.6 times higher than if their effects were purely additive. This result confirms that the combination of poly(A) and histoneSL effects a markedly synergistic increase in protein expression.

11.3 The Combination of Poly(A) and HistoneSL Increases Protein Expression from mRNA Irrespective of Their Order.

The effect of the combination of poly(A) and histoneSL might depend on the length of the poly(A) sequence and the order of poly(A) and histoneSL. Thus, mRNAs with increasing poly(A) sequence length and mRNA with poly(A) and histoneSL in reversed order were synthesized: Two mRNAs contained 3' of the 3'-UTR either an A120 or an A300 poly(A) sequence. One further mRNA contained 3' of the 3'-UTR first a histoneSL followed by an A250 poly(A) sequence. Luciferase-encoding mRNAs or control mRNA were lipofected into HeLa cells. Luciferase levels were measured at 6, 24, and 48 hours after the start of transfection (see following Table 8 and FIG. 19).

TABLE 8

| mRNA | RLU at 6 hours | RLU at 24 hours | RLU at 48 hours |
|---|---|---|---|
| ppLuc(GC)-ag-histoneSL-A250 | 98472 | 734222 | 146479 |
| ppLuc(GC)-ag-A64-histoneSL | 123674 | 317343 | 89579 |
| ppLuc(GC)-ag-histoneSL | 7291 | 4565 | 916 |
| ppLuc(GC)-ag-A300 | 4357 | 38560 | 11829 |
| ppLuc(GC)-ag-A120 | 4371 | 45929 | 10142 |
| ppLuc(GC)-ag-A64 | 1928 | 26781 | 537 |

Both an A64 poly(A) sequence or the histoneSL gave rise to comparable luciferase levels. In agreement with the previous experiment did the combination of A64 and histoneSL strongly increase the luciferase level, manifold above the level observed with either of the individual elements. The magnitude of the rise in luciferase level due to combining poly(A) and histoneSL in the same mRNA demonstrates that they are acting synergistically. The synergy between A64 and histoneSL was quantified as before based on the luciferase levels of A64-histoneSL, A64, and histoneSL mRNA (see following Table 9). The luciferase level from mRNA combining A64 and histoneSL was up to 61.7 times higher than if the effects of poly(A) and histoneSL were purely additive.

TABLE 9

| | A64 | histoneSL | RLU at 6 hours | RLU at 24 hours | RLU at 48 hours |
|---|---|---|---|---|---|
| | + | + | 123674 | 317343 | 89579 |
| | − | + | 7291 | 4565 | 916 |
| | + | − | 1928 | 26781 | 537 |
| Synergy | | | 13.4 | 10.1 | 61.7 |

In contrast, increasing the length of the poly(A) sequence from A64 to A120 or to A300 increased the luciferase level only moderately (see Table 8 and FIG. 19). mRNA with the longest poly(A) sequence, A300, was also compared to mRNA in which a poly(A) sequence of similar length was combined with the histoneSL, histoneSL-A250. In addition to having a long poly(A) sequence, the order of histoneSL and poly(A) is reversed in this mRNA relative to A64-histoneSL mRNA. The combination of A250 and histoneSL strongly increased the luciferase level, manifold above the level observed with either histoneSL or A300. Again, the synergy between A250 and histoneSL was quantified as before comparing RLU from histoneSL-A250 mRNA to RLU from A300 mRNA plus histoneSL mRNA (see following Table 10). The luciferase level from mRNA combining A250 and histoneSL was up to 17.0 times higher than if the effects of poly(A) and histoneSL were purely additive.

TABLE 10

| | histoneSL | A250/A300 | RLU at 6 hours | RLU at 24 hours | RLU at 48 hours |
|---|---|---|---|---|---|
| | + | + | 98472 | 734222 | 146479 |
| | + | − | 7291 | 4565 | 916 |
| | − | + | 4357 | 38560 | 11829 |
| Synergy | | | 8.5 | 17.0 | 11.5 |

In summary, a highly synergistic effect of the combination of histoneSL and poly(A) on protein expression from mRNA has been demonstrated for substantially different lengths of poly(A) and irrespective of the order of poly(A) and histoneSL.

11.4 The Rise in Protein Expression by the Combination of Poly(A) and HistoneSL is Specific To investigate whether the effect of the combination of poly(A) and histoneSL on protein expression from mRNA is specific, mRNAs with alternative sequences in combination with poly(A) were synthesized: These mRNAs contained 3' of A64 one of seven distinct sequences, respectively. Luciferase-encoding mRNAs or control mRNA were electroporated into HeLa cells. Luciferase levels were measured at 6, 24, and 48 hours after transfection (see following Table 11 and FIG. 20).

TABLE 11

| mRNA | RLU at 6 hours | RLU at 24 hours | RLU at 48 hours |
|---|---|---|---|
| ppLuc(GC)-ag-A64-N32 | 33501 | 38979 | 2641 |
| ppLuc(GC)-ag-A64-SL | 28176 | 20364 | 874 |
| ppLuc(GC)-ag-A64-U30 | 41632 | 54676 | 3408 |
| ppLuc(GC)-ag-A64-G30 | 46763 | 49210 | 3382 |
| ppLuc(GC)-ag-A64-PolioCL | 46428 | 26090 | 1655 |
| ppLuc(GC)-ag-A64-aCPSL | 34176 | 53090 | 3338 |
| ppLuc(GC)-ag-A64-ag | 18534 | 18194 | 989 |
| ppLuc(GC)-ag-A64-histoneSL | 282677 | 437543 | 69292 |

TABLE 11-continued

| mRNA | RLU at 6 hours | RLU at 24 hours | RLU at 48 hours |
|---|---|---|---|
| ppLuc(GC)-ag-histoneSL | 27597 | 3171 | 0 |
| ppLuc(GC)-ag-A64 | 14339 | 48414 | 9357 |

Both a poly(A) sequence or the histoneSL gave rise to comparable luciferase levels. Again, the combination of poly(A) and histoneSL strongly increased the luciferase level, manifold above the level observed with either of the individual elements, thus acting synergistically. In contrast, combining poly(A) with any of the alternative sequences was without effect on the luciferase level compared to mRNA containing only a poly(A) sequence. Thus, the combination of poly(A) and histoneSL increases protein expression from mRNA in a synergistic manner, and this effect is specific.

11.5 The Combination of Poly(A) and HistoneSL Increases Protein Expression from mRNA in a Synergistic Manner In Vivo.

To investigate the effect of the combination of poly(A) and histoneSL on protein expression from mRNA in vivo, Luciferase-encoding mRNAs with different sequences 3' of the alpha-globin 3'-UTR or control mRNA were injected intradermally into mice: mRNAs contained either an A64 poly(A) sequence or a histoneSL instead, or both A64 poly(A) and histoneSL 3' of the 3'-UTR. Luciferase levels were measured at 16 hours after injection (see following Table 12 and FIG. 21).

TABLE 12

| mRNA | RLU at 16 hours |
|---|---|
| ppLuc(GC)-ag-A64-histoneSL | 38081 |
| ppLuc(GC)-ag-histoneSL | 137 |
| ppLuc(GC)-ag-A64 | 4607 |

Luciferase was expressed from mRNA having either a histoneSL or a poly(A) sequence. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 13).

TABLE 13

| | A64 | histoneSL | RLU at 16 hours |
|---|---|---|---|
| | + | + | 38081 |
| | − | + | 137 |
| | + | − | 4607 |
| Synergy | | | 8.0 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was 8 times higher than if their effects were purely additive. This result confirms that the combination of poly(A) and histoneSL effects a markedly synergistic increase in protein expression in vivo.

11.6 The Combination of Poly(A) and HistoneSL Increases NY-ESO-1 Protein Expression from mRNA.

To investigate the effect of the combination of poly(A) and histoneSL on protein expression from mRNA, NY-ESO-1-encoding mRNAs with different sequences 3' of the alpha-globin 3'-UTR were synthesized: mRNAs contained either an A64 poly(A) sequence or both A64 poly(A) and histoneSL 3' of the 3'-UTR. NY-ESO-1-encoding mRNAs were electroporated into HeLa cells. NY-ESO-1 levels were measured at 24 hours after transfection by flow cytometry (see following Table 14 and FIG. 22).

TABLE 14

| | MFI at 24 hours | |
|---|---|---|
| mRNA | anti-NY-ESO-1 | isotype control |
| NY-ESO-1(GC)-ag-A64-histoneSL | 15600 | 1831 |
| NY-ESO-1(GC)-ag-A64 | 1294 | 849 |

NY-ESO-1 was expressed from mRNA having only a poly(A) sequence. Strikingly however, the combination of poly(A) and histoneSL strongly increased the NY-ESO-1 level, manifold above the level observed with only a poly(A) sequence.

11.7 The Combination of Poly(A) and HistoneSL Increases the Level of Antibodies Elicited by Vaccination with mRNA.

To investigate the effect of the combination of poly(A) and histoneSL on the induction of antibodies elicited by vaccination with mRNA, C57BL/6 mice were vaccinated intradermally with protamine-complexed, NY-ESO-1-encoding mRNAs with different sequences 3' of the alpha-globin 3'-UTR. mRNAs contained either an A64 poly(A) sequence or both A64 poly(A) and histoneSL 3' of the 3'-UTR. The level of NY-ESO-1-specific antibodies in vaccinated and control mice was analyzed by ELISA with serial dilutions of sera (see following Table 15 and FIG. 23).

TABLE 15

| mRNA | mean IgG2a[b] endpoint titer |
|---|---|
| NY-ESO-1(GC)-ag-A64-histoneSL | 763 |
| NY-ESO-1(GC)-ag-A64 | 20 |

Anti NY-ESO-1 IgG2a[b] was induced by mRNA having only a poly(A) sequence. Strikingly however, the combination of poly(A) and histoneSL strongly increased the anti NY-ESO-1 IgG2a[b] level, manifold above the level observed with only a poly(A) sequence.

The invention claimed is:

1. A method of expressing a therapeutic polypeptide in a patient comprising providing the patient with a composition comprising an isolated nucleic acid molecule comprising:

a) a coding region, encoding the therapeutic polypeptide, wherein the coding region does not code for histone polypeptides, reporter polypeptides selected from enhanced green fluorescent protein (EGFP) and Luciferase and selection polypeptides selected from alpha-Globin, Galactokinase and Xanthine:guanine phosphoribosyl transferase (GPT), b) at least one histone stem-loop, and c) a poly(A) sequence or a polyadenylation signal.

2. The method of claim 1, wherein the nucleic acid does not contain one of the components of the group consisting of: a sequence encoding a ribozyme, a viral nucleic acid sequence, a histone stem-loop processing signal, a Neo gene, an inactivated promoter sequence, and an inactivated enhancer sequence.

3. The method of claim 1, wherein the nucleic acid does not contain a ribozyme, and one of the group consisting of: a Neo gene, an inactivated promotor sequence, an inactivated enhancer sequence, and a histone stem-loop processing signal.

4. The method of claim 1, wherein the nucleic acid is an RNA.

5. The method of claim 4, wherein the RNA comprises a 5' cap structure and a poly(A) sequence of about 25 to about 400 adenosine nucleotides.

6. The method of claim 1, wherein the poly(A) sequence comprises a sequence of about 25 to about 400 adenosine nucleotides.

7. The method of claim 1, wherein the polyadenylation signal comprises the consensus sequence NNUANA, AAUAAA, or AUUAAA.

8. The method of claim 1, wherein the coding region encodes a therapeutic polypeptide selected from groups consisting a cytokine, lymphokine, monokine, growth factor, receptor, signal transduction molecule, transcription factor, anticoagulant; antithrombins, antiallergic protein, apoptotic factor, therapeutic active enzyme and a protein connected with an acquired disease or a hereditary disease.

9. The method of claim 1, wherein the coding region encodes a therapeutic antibody.

10. The method of claim 1, wherein the nucleic acid is monocistronic or bicistronic.

11. The method of claim 1, wherein the composition comprises a pharmaceutically acceptable carrier.

12. The method of claim 1, wherein the patient has a disease selected from the group consisting of a hereditary disease, autoimmune disease, allergy, cancer disease, tumour disease, and infectious disease.

13. The method of claim 1, wherein at least one guanosine, uridine, adenosine, thymidine, or cytidine position of the nucleic acid molecule is substituted with a nucleotide analogue selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, puromycin-5'-triphosphate, and xanthosine-5'-triphosphate.

14. The method of claim 1, wherein the composition is administered by injection.

15. The method of claim 14, wherein the composition is administered by subcutaneous, intravenous or intramuscular injection.

16. The method of claim 1, wherein the nucleic acid molecule further comprises a sequence of at least 10 consecutive cytidines.

17. The method of claim 1, wherein the nucleic acid molecule further comprises a stabilizing sequence.

18. The method of claim 17, wherein the stabilizing sequence comprises a sequence from the alpha globin 3' UTR, positioned 3' relative to the polypeptide coding region of the nucleic acid molecule.

19. The method of claim 1, wherein the composition further comprises a cationic or polycationic compound in complex with the nucleic acid molecule.

20. The method of claim 19, wherein the polycationic compound is a polycationic lipid or polypeptide.

* * * * *